(12) United States Patent
Freire

(10) Patent No.: US 11,351,140 B2
(45) Date of Patent: Jun. 7, 2022

(54) RESOLVIN MIMETIC ANTIBODIES AND USES THEREOF

(71) Applicant: J. Craig Venter Institute, Inc., La Jolla, CA (US)

(72) Inventor: Marcelo Freire, Los Angeles, CA (US)

(73) Assignee: J. Craig Venter Institute, La Jolla, CA (US)

( * ) Notice: Subject to any disclaimer, the term of this patent is extended or adjusted under 35 U.S.C. 154(b) by 174 days.

(21) Appl. No.: 16/611,203

(22) PCT Filed: May 17, 2018

(86) PCT No.: PCT/US2018/033208
§ 371 (c)(1),
(2) Date: Nov. 5, 2019

(87) PCT Pub. No.: WO2018/213592
PCT Pub. Date: Nov. 22, 2018

(65) Prior Publication Data
US 2020/0163922 A1   May 28, 2020

Related U.S. Application Data

(60) Provisional application No. 62/508,572, filed on May 19, 2017.

(51) Int. Cl.
| | | |
|---|---|---|
| C07K 16/28 | (2006.01) |
| A61K 39/395 | (2006.01) |
| A61P 29/00 | (2006.01) |
| A61K 31/202 | (2006.01) |
| A61K 39/00 | (2006.01) |
| C07K 19/00 | (2006.01) |
| C07K 14/705 | (2006.01) |
| A61K 45/06 | (2006.01) |

(52) U.S. Cl.
CPC ............ *A61K 31/202* (2013.01); *A61K 39/00* (2013.01); *A61K 39/3955* (2013.01); *C07K 16/28* (2013.01); *C07K 19/00* (2013.01); *A61K 45/06* (2013.01); *A61K 2039/505* (2013.01); *A61P 29/00* (2018.01); *C07K 14/705* (2013.01); *C07K 2317/56* (2013.01); *C07K 2317/622* (2013.01); *C07K 2317/75* (2013.01)

(58) Field of Classification Search
CPC .......................... C07K 16/28; C07K 2317/75
See application file for complete search history.

(56) References Cited

U.S. PATENT DOCUMENTS

2014/0227294 A1   8/2014   Anderson et al.

OTHER PUBLICATIONS

Freire et al (2017. Journal of Immunology. 198: 718-728).*

(Continued)

*Primary Examiner* — Zachary C Howard
(74) *Attorney, Agent, or Firm* — Knobbe Martens Olson & Bear LLP

(57) ABSTRACT

Provided herein are compositions comprising a resolvin mimetic. Such mimetics may comprise an anti-ERV1 antibody, such as a resolvimab, or biologically-active antibody fragment thereof. Also provided herein are methods for treating or preventing an inflammatory disorder in a subject in need thereof comprising the steps of administering a therapeutically effective amount of at least one resolvin mimetic.

10 Claims, 39 Drawing Sheets

Specification includes a Sequence Listing.

(56) References Cited

OTHER PUBLICATIONS

Sulciner et al (2018. J. Exp. Med. 2018. 215(1): 115-140).*
Salic et al (2016. Atherosclerosis. 250: 158-165).*
Freire, Marcelo "Resolution of Inflammation in Type 2 Diabetes" Doctoral dissertation, Harvard School of Dental Medicine, Apr. 2016.
International Search Report for PCT/US2018/033208 dated Oct. 9, 2018.

* cited by examiner

FIG. 1A
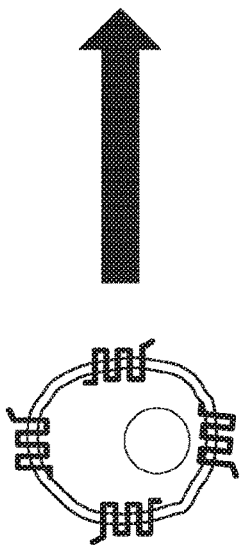
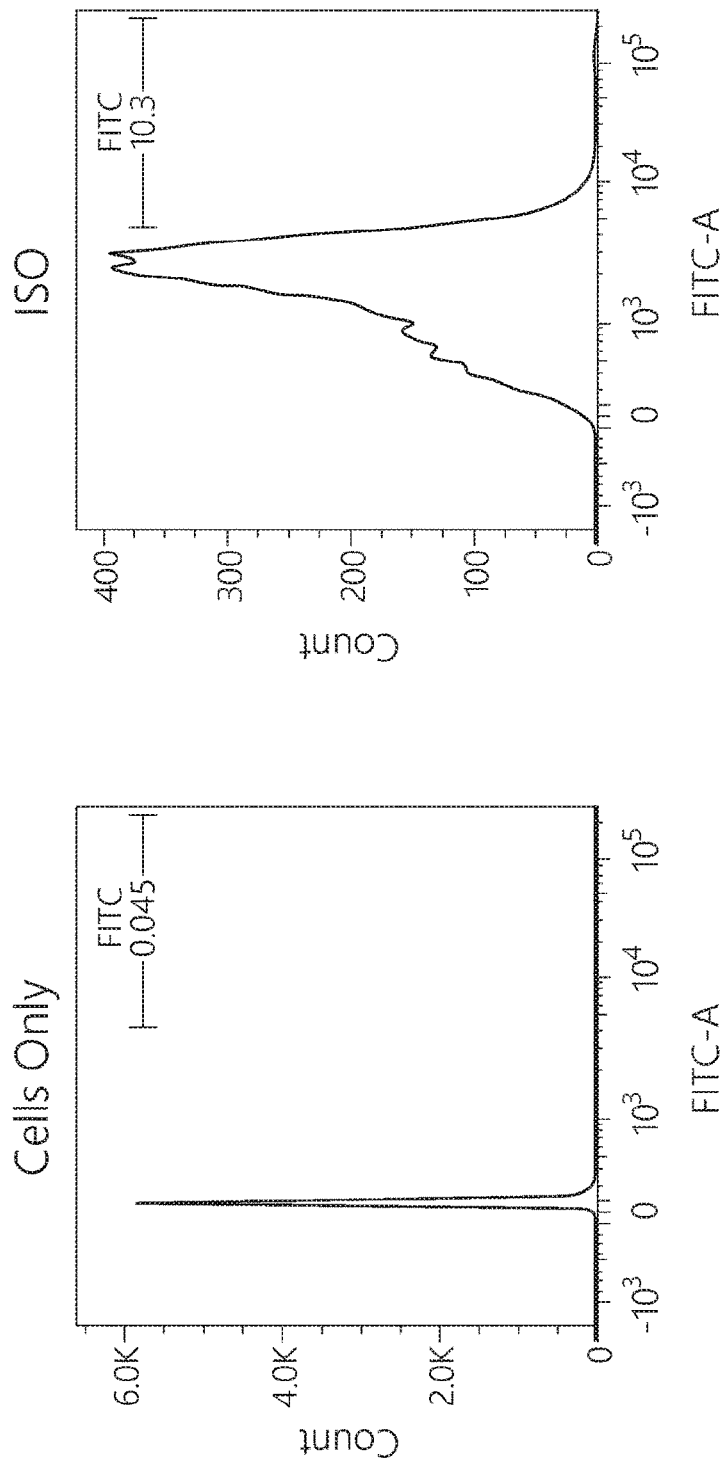

FIG. 1B
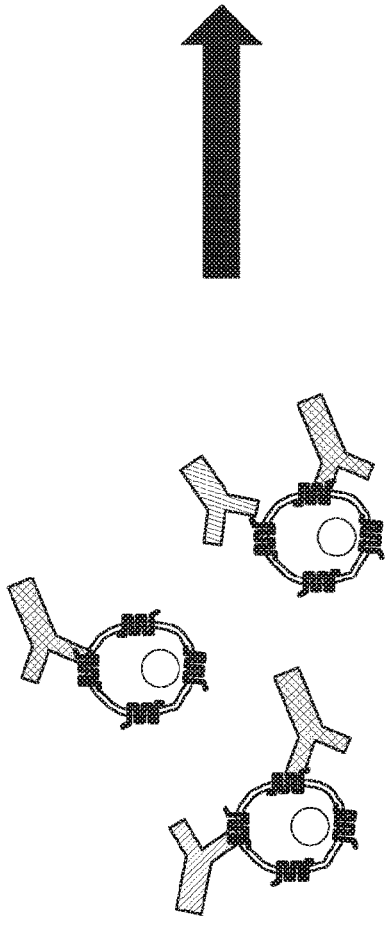
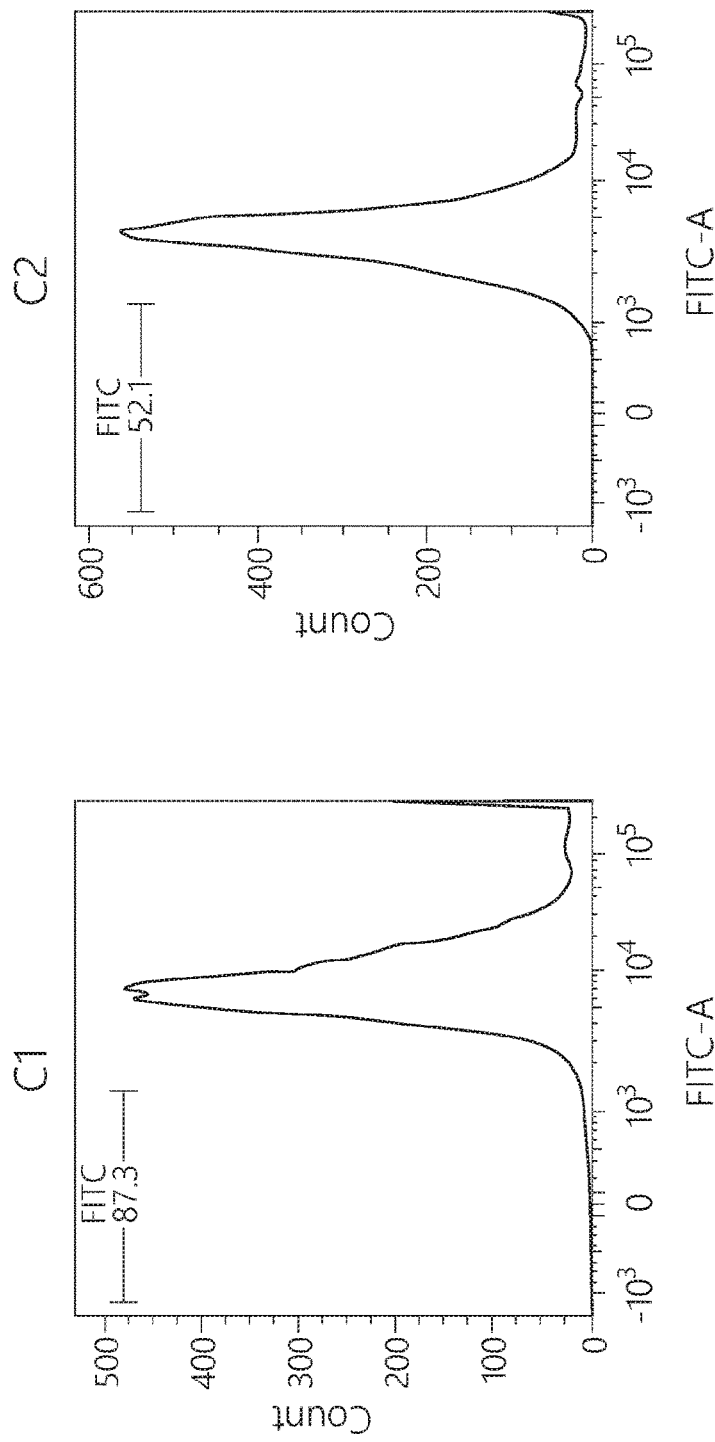

Resolvimab
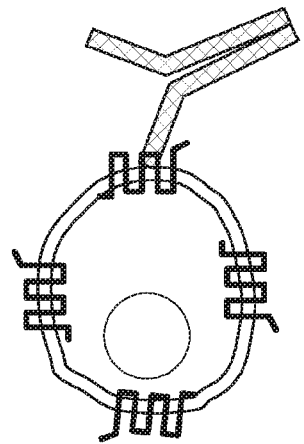
Intracellular Calcium
Inflammation Resolution
FIG. 2A

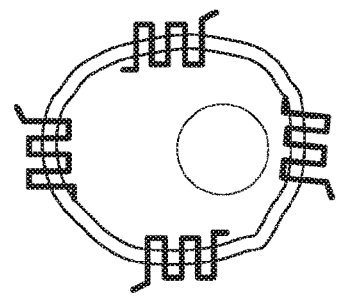
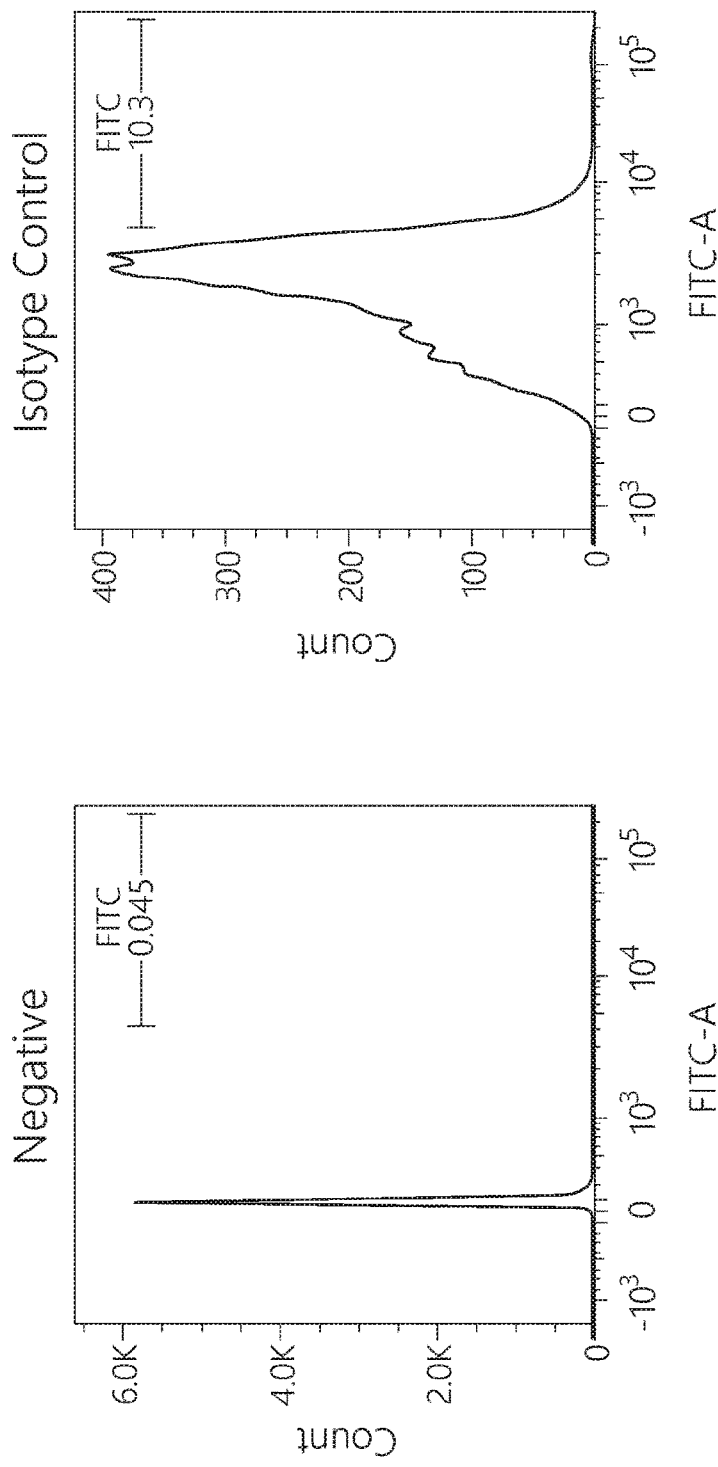
FIG. 5A

| CLONE ID | PARENTAL | ISOTYPING |
|---|---|---|
| C1 | 1G12.G8-2.C3 | IgG1 κ |
| C2 | 5G4.F8-1.G5 | IgG1 κ |
| C3 | 5G4.F8-1B7 | IgG1 κ |
| C4 | 5G4.F8-1.C10 | IgG1 κ/λ |

Intracellular Calcium

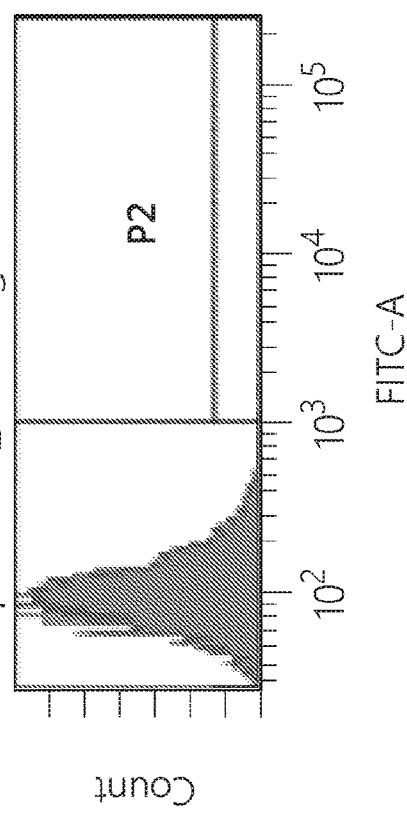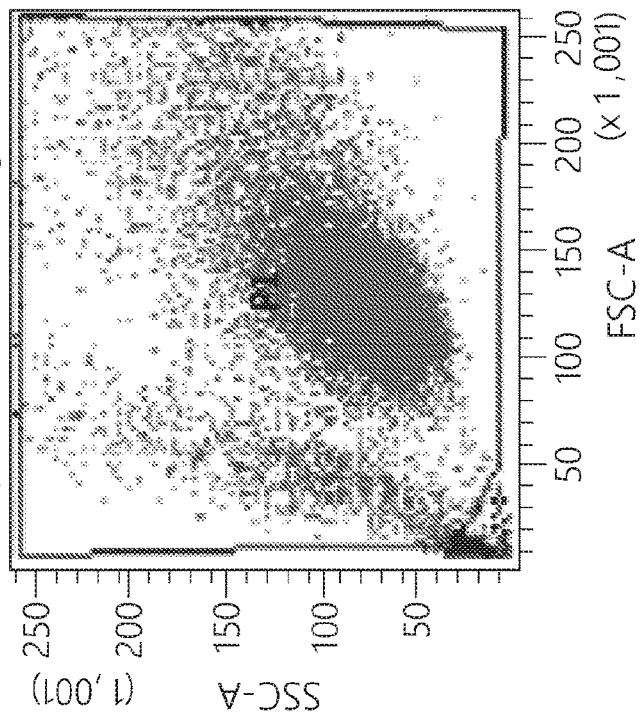
FIG. 12A

Positive Ab Binder
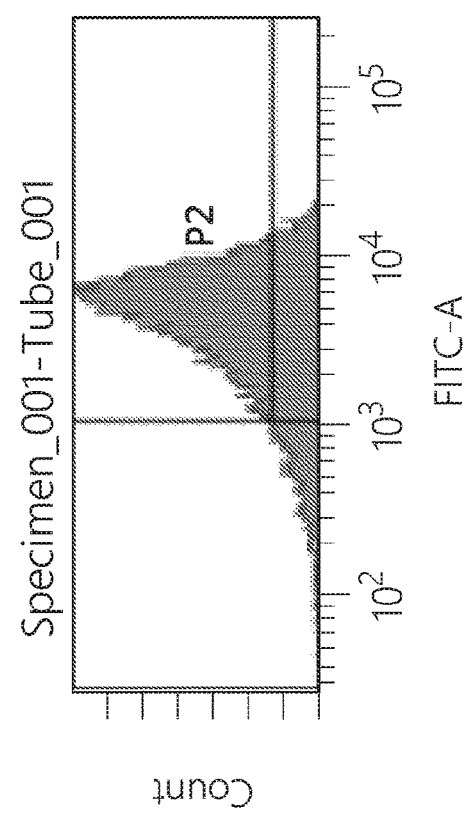
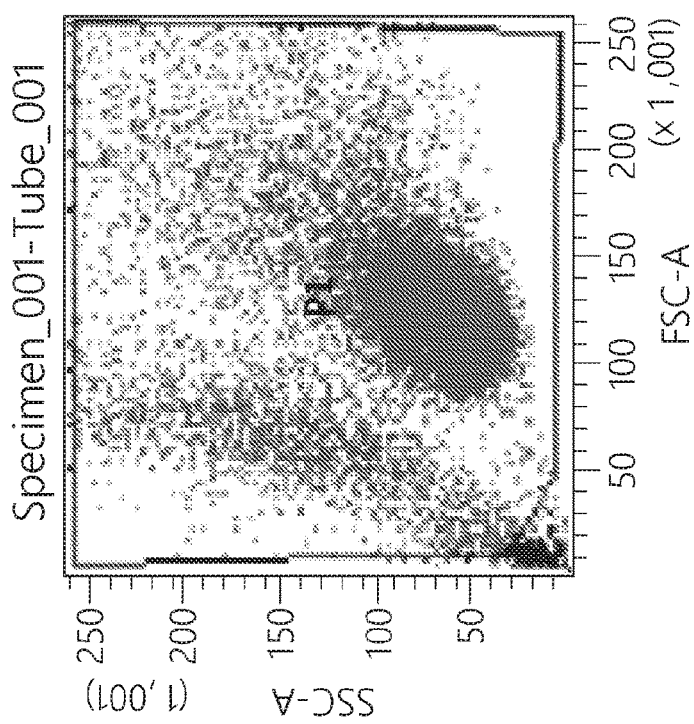
FIG. 12B

| CLONE ID | PARENTAL | ISOTYPING |
|---|---|---|
| C1 | 1G12.G8-2.C3 | IgG1 κ |
| C2 | 5G4.F8-1.G5 | IgG1 κ |
| C3 | 5G4.F8-1B7 | IgG1 κ |
| C4 | 5G4.F8-1.C10 | IgG1 κ/λ |

FIG. 13A

VH Region

>33686_1_1G12_G8-2_C3-VH 345 bp
GAGCTTGTGATGCCTGGGGCTTCAGTGAAGCTGTCCTGCAAGGCTTCTGGCTACACCTTC
ACCAGCTACTGGATGCACTGGGTGAAGCAGAGGCCTGGACAAGGCCTTGAGTGGGTCGCA
GAGATTGATCCTTCTGATAGTTATACTAACTACAATCAAAAGTTCAAGGGCAAGGCCACA
TTGACTGTAGACAAATCCTCCAGCACAGCCTACATGCAGCTCAGCAGCCTGACATCTGAG
GACTCTGCGGTCTATTACTGTGCAAGAGATGGGGATATATTAACTACGGTAGTAGCTAAG
GGGTTTGTTTACTGGGGCCAAGGGACTCTGGTCACTGTCTCTGCA

>33686_2_5G4_F8-1_G5-VH 372 bp
GAGGTTCAGCTGCAGCAGTCTGGGGCTGAGCTTGTGATGCCTGGGGCTTCAGTGAAGCTG
TCCTGCAAGGCTTCTGGCTACACCTTCACCAGCTACTGGATGCACTGGGTGAAGCAGAGG
CCTGGACAAGGCCTTGAGTGGGTCGCAGAGATTGATCCTTCTGATAGTTATACTAACTAC
AATCAAAAGTTCAAGGGCAAGGCCACATTGACTGTAGACAAATCCTCCAGCACAGCCTAC
ATGCAGCTCAGCAGCCTGACATCTGAGGACTCTGCGGTCTATTACTGTGCAAGAGATGGG
GATATATTAACTACGGTAGTAGCTAAGGGGTTTGTTTACTGGGGCCAAGGGACTCTGGTC
ACTGTCTCTGCA

>33686_3_5G4_F8-1_B7-VH 372 bp
GAGGTGCAGCTGCAGCAGTCTGGGGCTGAGCTTGTGATGCCTGGGGCTTCAGTGAAGCTG
TCCTGCAAGGCTTCTGGCTACACCTTCACCAGCTACTGGATGCACTGGGTGAAGCAGAGG
CCTGGACAAGGCCTTGAGTGGGTCGCAGAGATTGATCCTTCTGATAGTTATACTAACTAC
AATCAAAAGTTCAAGGGCAAGGCCACATTGACTGTAGACAAATCCTCCAGCACAGCCTAC
ATGCAGCTCAGCAGCCTGACATCTGAGGACTCTGCGGTCTATTACTGTGCAAGAGATGGG
GATATATTAACTACGGTAGTAGCTAAGGGGTTTGTTTACTGGGGCCAAGGGACTCTGGTC
ACTGTCTCTGCA

>33686_4_5G4_F8-1_C10-VH 372 bp
GAAGTTAAGCTGGAGGAGTCTGGGGCTGAGCTTGTGATGCCTGGGGCTTCAGTGAAGCTG
TCCTGCAAGGCTTCTGGCTACACCTTCACCAGCTACTGGATGCACTGGGTGAAGCAGAGG
CCTGGACAAGGCCTTGAGTGGGTCGCAGAGATTGATCCTTCTGATAGTTATACTAACTAC
AATCAAAAGTTCAAGGGCAAGGCCACATTGACTGTAGACAAATCCTCCAGCACAGCCTAC
ATGCAGCTCAGCAGCCTGACATCTGAGGACTCTGCGGTCTATTACTGTGCAAGAGATGGG
GATATATTAACTACGGTAGTAGCTAAGGGGTTTGTTTACTGGGGCCAAGGGACTCTGGTC

FIG. 14A

VK Region Alignment

>33686_5_1G12_G8-2_C3-VK 312 bp
CTCTCCCTGCCTGTCAGTCTTGGAGATCAAGCCTCCATCTCTTGCAGATCTAGTCAGACC
ATTGTACATAGTAATGGAAACACCTATTTAGAATGGTACCTGCAGAAACCAGGCCAGTCT
CCAAAGCTCCTGATCTACAAAGTTTCCAACCGATTTTCTGGGGTCCCAGACAGGTTCAGT
GGCAGTGGATCAGGGACAGATTTCACACTCAAGATCAGCAGAGTGGAGGCTGAGGATCTG
GGAGTTTATTACTGCTTTCAAGGTTCACATGTTCCGTGGACGTTCGGTGGAGGCACCAAG
CTGGAAATCAAA

>33686_6_5G4_F8-1_G5-VK 312 bp
CTCTCCCTGCCTGTCAGTCTTGGAGATCAAGCCTCCATCTCTTGCAGATCTAGTCAGACC
ATTGTACATAGTAATGGAAACACCTATTTAGAATGGTACCTGCAGAAACCAGGCCAGTCT
CCAAAGCTCCTGATCTACAAAGTTTCCAACCGATTTTCTGGGGTCCCAGACAGGTTCAGT
GGCAGTGGATCAGGGACAGATTTCACACTCAAGATCAGCAGAGTGGAGGCTGAGGATCTG
GGAGTTTATTACTGCTTTCAAGGTTCACATGTTCCGTGGACGTTCGGTGGAGGCACCAAG
CTGGAAATCAAA

>33686_7_5G4_F8-1_B7-VK 312 bp
CTCTCCCTGCCTGTCAGTCTTGGAGATCAAGCCTCCATCTCTTGCAGATCTAGTCAGACC
ATTGTACATAGTAATGGAAACACCTATTTAGAATGGTACCTGCAGAAACCAGGCCAGTCT
CCAAAGCTCCTGATCTACAAAGTTTCCAACCGATTTTCTGGGGTCCCAGACAGGTTCAGT
GGCAGTGGATCAGGGACAGATTTCACACTCAAGATCAGCAGAGTGGAGGCTGAGGATCTG
GGAGTTTATTACTGCTTTCAAGGTTCACATGTTCCGTGGACGTTCGGTGGAGGCACCAAG
CTGGAAATCAAA

>33686_8_5G4_F8-1_C10-VK 312 bp
CTCTCCCTGCCTGTCAGTCTTGGAGATCAAGCCTCCATCTCTTGCAGATCTAGTCAGACC
ATTGTACATAGTAATGGAAACACCTATTTAGAATGGTACCTGCAGAAACCAGGCCAGTCT
CCAAAGCTCCTGATCTACAAAGTTTCCAACCGATTTTCTGGGGTCCCAGACAGGTTCAGT
GGCAGTGGATCAGGGACAGATTTCACACTCAAGATCAGCAGAGTGGAGGCTGAGGATCTG
GGAGTTTATTACTGCTTTCAAGGTTCACATGTTCCGTGGACGTTCGGTGGAGGCACCAAG
CTGGAAATCAAA

FIG. 14B

WT-hERVI - C4 clone
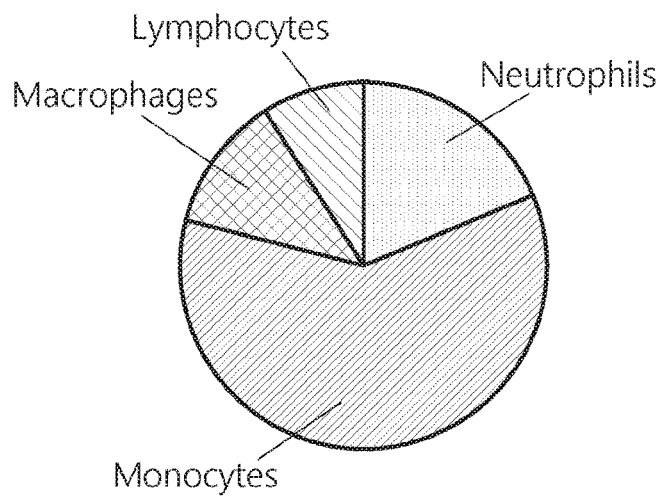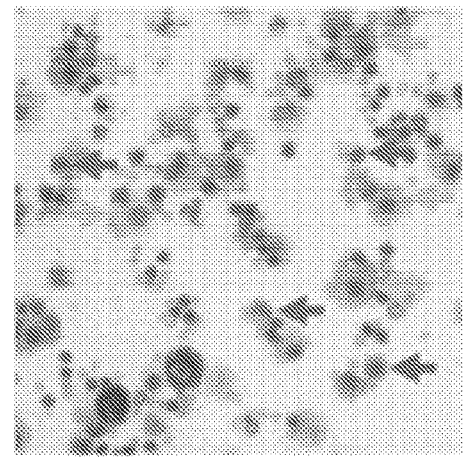
db/db-hERVI - C4 clone
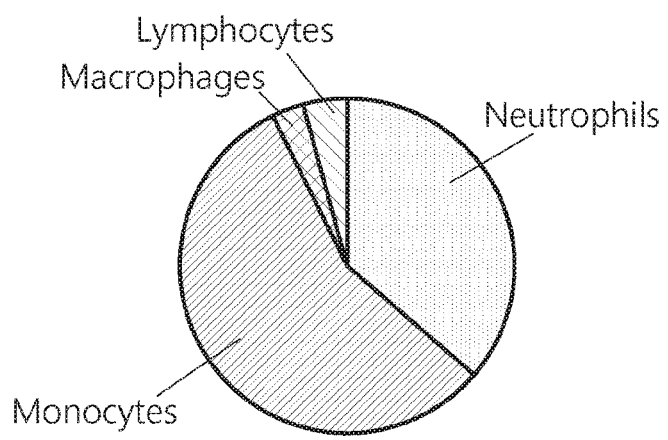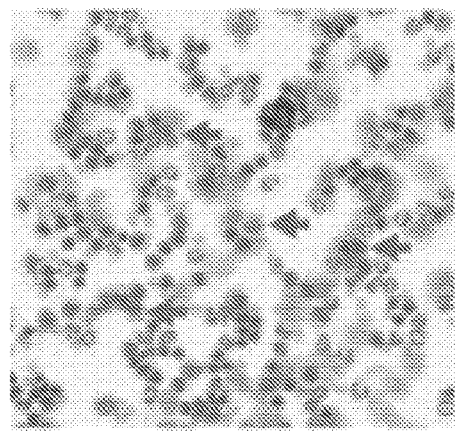
FIG. 16C

RESOLVIN MIMETIC ANTIBODIES AND USES THEREOF

INCORPORATION BY REFERENCE TO ANY PRIORITY APPLICATIONS

This application is a U.S. National Phase Application of PCT International Application Number PCT/US2018/033208, filed on May 17, 2018, designating the United States of America and published in the English language, which is an International Application of and claims the benefit of priority to U.S. Provisional Application No. 62/508,572, filed on May 19, 2017. The disclosures of the above-referenced applications are hereby expressly incorporated by reference in their entireties.

STATEMENT REGARDING FEDERALLY SPONSORED R&D

This invention was made with government support under grant number DE023584 awarded by the National Institutes of Health. The government has certain rights in the invention.

REFERENCE TO SEQUENCE LISTING

A Sequence Listing submitted as an ASCII text file via EFS-Web is hereby incorporated by reference in accordance with 37 CFR § 1.52(e). The name of the ASCII text file for the Sequence Listing is SeqList-JCVEN-005NP.txt, the date of creation of the ASCII text file is Oct. 29, 2019, and the size of the ASCII text file is 13,152 bytes.

BACKGROUND

Field of the Disclosure

The present disclosure relates generally to the field of Inflammation and the treatment thereof. Inflammation is a normal part of the immune system's response to harmful stimuli and is often a temporary process, lasting minutes to a few hours in most cases. However, chronic inflammation—inflammation that persists for weeks to months, or even years—can have devastating effects on the body if left unchecked. The number of cancers with inflammatory links is staggering: bladder, liver, colorectal, esophageal, pancreatic, lung, breast, ovarian, cervical, gall bladder, and oral squamous cell carcinomas are all known to begin with some chronic inflammatory condition that then predisposes cells to neoplastic transformation. In the U.S., lung cancer leads to over 150,000 deaths each year (R. Siegel et al., CA Cancer. J. Clin., 2015, 65:339-344). Type 2 diabetes (T2D) and cardiovascular disease (CVD) also have well-known links with inflammation. According to data collected in 2014 by the International Diabetes Federation, some 387 million people—1 in 12 people in the world—are currently living with diabetes, and that number is expected to rise to nearly 600 million by 2035. Diabetes imposes a large economic burden on individuals and families, national health systems, and countries. Health spending on diabetes accounted for 10.8% of total health expenditure worldwide in 2013 (IDF Diabetes Atlas (6th Edition), 2014). Furthermore, an estimated 85.6 million American adults have at least one type of CVD (e.g., high blood pressure, coronary heart disease, and ischemic stroke), with more than 2.5 million deaths attributed to CVD in the U.S. annually (D. Mozaffarian et al., Circulation, 2015, 131). These data show the enormous toll on the health of individuals worldwide when a chronic inflammatory condition(s) exists.

Background

The difference between whether an inflammatory response is acute or chronic involves the onset of inflammation resolution, or the lack thereof. Until recently, the resolution phase of inflammation was poorly understood and thought to be a passive process, but recent research has elucidated many of the biochemical signaling pathways involved in the return to homeostasis following inflammatory episodes. The local acute inflammatory response is characterized first by the formation of exudate and the infiltration of neutrophils into the site of inflammation. This is followed by the recruitment of monocytes that then differentiate into macrophages. These cells release various endogenous lipid mediators that work together to regulate the initial events of inflammation. Arachidonic acid released from membrane phospholipids by phospholipase A2 can be further metabolized to generate either i) more pro-inflammatory signals (e.g., prostaglandins, thromboxanes, and leukotrienes) or ii) pro-resolution lipid mediators such as lipoxins. Other pro-resolution mediators synthesized during the switch from a pro- to anti-inflammatory response include the eicosapentaenoic acid-derived E-series resolvins, and docosahexaenoic acid-derived D-series resolvins, protectins and maresins (M. Friere and T. Van Dyke, Periodontol 2000, 63(1):149-164 (2013)); Laguna-Fernandez, A. et al., Circulation, doi:10.1161/CIRCULATIONAHA.117.032801 (2018). When this switch in favor of resolution-promoting lipids is compromised, a prolonged inflammatory state often develops, the results of which can include i) fibrosis, with large amounts of tissue destruction and eventual scarring, ii) abscess formation, with dead leukocytes and pathogens as well as general cell debris from macrophage-destroyed cells, and iii) chronic inflammation, with persistence of macrophages in the wound site releasing toxins that lead to widespread tissue destruction.

Current treatment of inflammation and/or chronic inflammatory diseases usually involves administration of medications such as i) non-steroidal anti-inflammatory drugs (NSAIDS) (e.g., aspirin (ASA) and naproxen), ii) glucocorticoids, and/or iii) cytokine blockers (e.g., anti TNF-alpha and IL-1 blockers), which are all designed to inhibit the production of pro-inflammatory chemical mediators. While these medications can be used to dampen the immune response and suppress symptoms of inflammation, they often hinder the ability of pro-resolvin mediators to effectively promote inflammation resolution. Therefore, there remains a need for novel, improved methods for preventing and treating inflammatory diseases. In particular, methods for induction of pro-resolution programs by cells within the sites of inflammation are highly desirable.

SUMMARY

Aspects of the present invention relate, at least in part, to peptide molecules that act as biomimetics of the resolvin class of lipid molecules. In some embodiments, the peptide has or comprises an amino acid sequence selected from the group consisting of SEQ ID NOs: 2, 4, 6, 8, 10, 12, 14, and 16, or biologically active variant thereof, or combinations thereof. Thus, in one aspect of the invention, the peptide or a composition comprising the peptide (e.g., an oral product such as a mouth wash, rinse, gel, or tooth paste) can be used for the treatment, inhibition, or amelioration of inflammation, or inflammatory conditions associated with inflammation, in particular chronic inflammation.

In one aspect, the present invention provides peptide molecules that are antibodies or binding fragments thereof. The antibody can be a monoclonal antibody, chimeric antibody, humanized antibody, polyclonal antibody, or a single-domain antibody. Other embodiments include antibody fragments such as fragment antigen-binding (Fab) fragments, including variable heavy chain (VH) and variable light chain (VK) fragments, single-chain variable region (scFv) fragments, or complementarity determining regions (CDR). In some embodiments, the antibody is a Resolvin mimetic antibody (e.g., a resolvimab). Binding fragments of the Resolvin mimetic antibody are also contemplated. In certain embodiments, the resolvimab or a composition (e.g., an oral product such as a mouth wash, rinse, gel, or tooth paste) comprises a variable heavy chain (VH) sequence encoded by a nucleotide sequence selected from the group consisting of SEQ ID NO: 1, 5, 9, and 13, or a combination thereof. In certain embodiments, the resolvimab or a composition (e.g., an oral product such as a mouth wash, rinse, gel, or tooth paste) comprises a variable light chain (VK) sequence encoded by a nucleotide sequence selected from the group consisting of SEQ ID NO: 3, 7, 11, and 15, or a combination thereof. In certain embodiments, the resolvimab or a composition (e.g., an oral product such as a mouth wash, rinse, gel, or tooth paste) comprises a variable heavy chain (VH) sequence comprising an amino acid sequence selected from the group consisting of SEQ ID NO: 2, 6, 10, and 14, or a biologically active variant thereof, or combination thereof. In certain embodiments, the resolvimab or a composition (e.g., an oral product such as a mouth wash, rinse, gel, or tooth paste) comprises a variable light chain (VK) sequence comprising an amino acid sequence selected from the group consisting of SEQ ID NO: 4, 8, 12, and 16, or a biologically active variant thereof, or combination thereof.

In certain embodiments, the resolvimab or a composition (e.g., an oral product such as a mouth wash, rinse, gel, or tooth paste) comprises a variable heavy chain (VH) sequence having at least 70%, 75%, 80%, 85%, 90%, 91%, 92%, 93%, 94%, 95%, 96%, 97%, 98% or 99% sequence identity to an amino acid sequence selected from the group consisting of SEQ ID NO: 2, 6, 10, and/or 14, or a biologically active variant thereof, or combination thereof. In certain embodiments, the resolvimab or a composition (e.g., an oral product such as a mouth wash, rinse, gel, or tooth paste) comprises a variable light chain (VK) sequence having at least 70%, 75%, 80%, 85%, 90%, 91%, 92%, 93%, 94%, 95%, 96%, 97%, 98% or 99% sequence identity to an amino acid sequence selected from the group consisting of SEQ ID NO: 4, 8, 12, and/or 16, or a biologically active variant thereof, or combination thereof.

In certain embodiments, the resolvimab (e.g., 1G12.G8-2.C3) or a composition (e.g., an oral product such as a mouth wash, rinse, gel, or tooth paste) comprises a variable heavy chain (VH) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 2 and a variable light chain (VK) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 4. In certain embodiments, the resolvimab (e.g., 1G12.G8-2.C3) or composition (e.g., an oral product such as a mouth wash, rinse, gel, or tooth paste) comprises a variable heavy chain (VH) sequence having at least 70%, 75%, 80%, 85%, 90%, 91%, 92%, 93%, 94%, 95%, 96%, 97%, 98% or 99% sequence identity to a nucleotide sequence set forth in SEQ ID NO: 1, which encodes a polypeptide sequence having at least 70%, 75%, 80%, 85%, 90%, 91%, 92%, 93%, 94%, 95%, 96%, 97%, 98% or 99% sequence identity to the amino acid sequence set forth in SEQ ID NO: 2, and a variable light chain (VK) sequence having at least 70%, 75%, 80%, 85%, 90%, 91%, 92%, 93%, 94%, 95%, 96%, 97%, 98% or 99% sequence identity to a nucleotide sequence set forth in SEQ ID NO: 3, which encodes a polypeptide sequence having at least 70%, 75%, 80%, 85%, 90%, 91%, 92%, 93%, 94%, 95%, 96%, 97%, 98% or 99% sequence identity to the amino acid sequence set forth in SEQ ID NO: 4. In certain embodiments, the resolvimab (e.g., 5G4.F8-1.G5) or composition (e.g., an oral product such as a mouth wash, rinse, gel, or tooth paste) comprises a variable heavy chain (VH) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 6 and a variable light chain (VK) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 8. In certain embodiments, the resolvimab (e.g., 5G4.F8-1.G5) or composition (e.g., an oral product such as a mouth wash, rinse, gel, or tooth paste) comprises a variable heavy chain (VH) sequence having at least 70%, 75%, 80%, 85%, 90%, 91%, 92%, 93%, 94%, 95%, 96%, 97%, 98% or 99% sequence identity to a nucleotide sequence set forth in SEQ ID NO: 5, which encodes a polypeptide sequence having at least 70%, 75%, 80%, 85%, 90%, 91%, 92%, 93%, 94%, 95%, 96%, 97%, 98% or 99% sequence identity to an amino acid sequence set forth in SEQ ID NO: 6, and a variable light chain (VK) sequence having at least 70%, 75%, 80%, 85%, 90%, 91%, 92%, 93%, 94%, 95%, 96%, 97%, 98% or 99% sequence identity to a nucleotide sequence set forth in SEQ ID NO: 7, which encodes a polypeptide sequence having at least 70%, 75%, 80%, 85%, 90%, 91%, 92%, 93%, 94%, 95%, 96%, 97%, 98% or 99% sequence identity to an amino acid sequence set forth in SEQ ID NO: 8. In certain embodiments, the resolvimab (e.g., 5G4.F8-1B7) or composition (e.g., an oral product such as a mouth wash, rinse, gel, or tooth paste) comprises a variable heavy chain (VH) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 10 and a variable light chain (VK) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 12. In certain embodiments, the resolvimab (e.g., 5G4.F8-1B7) or composition (e.g., an oral product such as a mouth wash, rinse, gel, or tooth paste) comprises a variable heavy chain (VH) sequence having at least 70%, 75%, 80%, 85%, 90%, 91%, 92%, 93%, 94%, 95%, 96%, 97%, 98% or 99% sequence identity to a nucleotide sequence set forth in SEQ ID NO: 9, which encodes a polypeptide sequence having at least 70%, 75%, 80%, 85%, 90%, 91%, 92%, 93%, 94%, 95%, 96%, 97%, 98% or 99% sequence identity to the amino acid sequence set forth in SEQ ID NO: 10, and a variable light chain (VK) sequence having at least 70%, 75%, 80%, 85%, 90%, 91%, 92%, 93%, 94%, 95%, 96%, 97%, 98% or 99% sequence identity to nucleotide sequence set forth in SEQ ID NO: 11, which encodes a polypeptide sequence having at least 70%, 75%, 80%, 85%, 90%, 91%, 92%, 93%, 94%, 95%, 96%, 97%, 98% or 99% sequence identity to an amino acid sequence set forth in SEQ ID NO: 12. In certain embodiments, the resolvimab (e.g., 5G4.F8-1.C10) or composition (e.g., an oral product such as a mouth wash, rinse, gel, or tooth paste) comprises a variable heavy chain (VH) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 14 and a variable light chain (VK) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 16. In certain embodiments, the resolvimab (e.g., 5G4.F8-1.C10) or composition (e.g., an oral product such as a mouth wash, rinse, gel, or tooth paste) comprises a variable heavy chain (VH) sequence having at least 70%, 75%, 80%, 85%, 90%, 91%, 92%, 93%, 94%, 95%, 96%, 97%, 98% or 99% sequence identity to a nucleotide sequence set forth in SEQ ID NO: 13, which encodes a polypeptide sequence having at least 70%, 75%, 80%, 85%, 90%, 91%, 92%, 93%, 94%, 95%, 96%, 97%, 98% or 99% sequence identity to an amino acid sequence set forth in SEQ ID NO: 14, and a variable light chain (VK) sequence having at least 70%, 75%, 80%, 85%, 90%, 91%, 92%, 93%, 94%, 95%, 96%, 97%, 98% or 99% sequence identity to nucleotide sequence set forth in SEQ ID NO: 15, which encodes a polypeptide sequence having at least 70%, 75%, 80%, 85%, 90%, 91%, 92%, 93%, 94%, 95%, 96%, 97%, 98% or 99% sequence identity to an amino acid sequence set forth in SEQ ID NO: 16. Yet another embodiment (e.g., an oral product such as a mouth wash, rinse, gel, or tooth paste) comprises aptamers, which are designed or are configured to bind a peptide molecule having at least 70%, 75%, 80%, 85%, 90%, 91%, 92%, 93%, 94%, 95%, 96%, 97%, 98% or 99% sequence identity to an amino acid sequence selected from the group consisting of SEQ ID NOs: 2, 4, 6, 8, 10, 12, 14, and 16, or a biologically active variant thereof, or combinations thereof.

In certain embodiments, the resolvimab (e.g., 1G12.G8-2.C3) or composition (e.g., an oral product such as a mouth wash, rinse, gel, or tooth paste), comprises a variable heavy chain (VH) sequence comprising an amino acid sequence set forth in SEQ ID NO: 2 and a variable light chain (VK) sequence comprising an amino acid sequence set forth in SEQ ID NO: 4. In certain embodiments, the resolvimab (e.g., 1G12.G8-2.C3) or composition (e.g., an oral product such as a mouth wash, rinse, gel, or tooth paste) comprises a variable heavy chain (VH) sequence comprising a nucleotide sequence set forth in SEQ ID NO: 1, which encodes a polypeptide sequence set forth in SEQ ID NO: 2, and a variable light chain (VK) sequence comprising nucleotide sequence set forth in SEQ ID NO: 3, which encodes a polypeptide sequence set forth in SEQ ID NO: 4. In certain embodiments, the resolvimab (e.g., 5G4.F8-1.G5) or composition (e.g., an oral product such as a mouth wash, rinse, gel, or tooth paste) comprises a variable heavy chain (VH) sequence comprising an amino acid sequence set forth in SEQ ID NO: 6 and a variable light chain (VK) sequence comprising an amino acid sequence set forth in SEQ ID NO: 8. In certain embodiments, the resolvimab (e.g., 5G4.F8-1.G5) or composition (e.g., an oral product such as a mouth wash, rinse, gel, or tooth paste) comprises a variable heavy chain (VH) sequence comprising a nucleotide sequence set forth in SEQ ID NO: 5, which encodes a polypeptide sequence set forth in SEQ ID NO: 6, and a variable light chain (VK) sequence comprising nucleotide sequence set forth in SEQ ID NO: 7, which encodes a polypeptide sequence set forth in SEQ ID NO: 8. In certain embodiments, the resolvimab (e.g., 5G4.F8-1B7) or composition (e.g., an oral product such as a mouth wash, rinse, gel, or tooth paste) comprises a variable heavy chain (VH) sequence comprising an amino acid sequence set forth in SEQ ID NO: 10 and a variable light chain (VK) sequence comprising an amino acid sequence set forth in SEQ ID NO: 12. In certain embodiments, the resolvimab (e.g., 5G4.F8-1B7) or composition (e.g., an oral product such as a mouth wash, rinse, gel, or tooth paste) comprises a variable heavy chain (VH) sequence comprising a nucleotide sequence set forth in SEQ ID NO: 9, which encodes a polypeptide sequence set forth in SEQ ID NO: 10, and a variable light chain (VK) sequence comprising nucleotide sequence set forth in SEQ ID NO: 11, which encodes a polypeptide sequence set forth in SEQ ID NO: 12. In certain embodiments, the resolvimab (e.g., 5G4.F8-1.C10) or composition (e.g., an oral product such as a mouth wash, rinse, gel, or tooth paste) comprises a variable heavy chain (VH) sequence comprising an amino acid sequence set forth in SEQ ID NO: 14 and a variable light chain (VK) sequence comprising an amino acid sequence set forth in SEQ ID NO: 16. In certain embodiments, the resolvimab (e.g., 5G4.F8-1.C10) or composition (e.g., an oral product such as a mouth wash, rinse, gel, or tooth paste) comprises a variable heavy chain (VH) sequence comprising a nucleotide sequence set forth in SEQ ID NO: 13, which encodes a polypeptide sequence set forth in SEQ ID NO: 14, and a variable light chain (VK) sequence comprising nucleotide sequence set forth in SEQ ID NO: 15, which encodes a polypeptide sequence set forth in SEQ ID NO: 16. Yet another embodiment (e.g., an oral product such as a mouth wash, rinse, gel, or tooth paste) comprises aptamers that are designed or are configured to bind a peptide molecule having an amino acid sequence selected from the group consisting of SEQ ID NOs: 2, 4, 6, 8, 10, 12, 14, and 16, or a biologically active variant thereof, or combinations thereof.

In another aspect, alternatives of the present invention include methods of treating, inhibiting, ameliorating or preventing an inflammatory disorder that would benefit from increased induction of inflammation resolution in a subject in need thereof comprising administering a therapeutically effective amount of a resolvin biomimetic peptide as set forth above (e.g., resolvimab or a fragment thereof) or a composition comprising the resolving biomimetic peptide (e.g., an oral product such as a mouth wash, rinse, gel, or tooth paste) to the subject to thereby treat, inhibit, ameliorate, or prevent the inflammatory disorder.

In some embodiments, the inflammatory disorder, which is inhibited, ameliorated, or treated, is selected from the group consisting of allergic reactions, anaphylactic reactions, arthritis, asthma, atherosclerosis, bone diseases, breast cancer, cancer, cardiovascular diseases, colon cancer, degenerative neurologic disorders, dementia, diabetes mellitus, eye diseases, gastrointestinal disorders, genitourinary disorders, hematologic disorders, hepatobiliary disorders, hypertension, infectious diseases, leukemia/lymphoma, lung cancer, metabolic disorders, neurological disorders, neuromuscular disorders, obesity/eating disorders, parasitic diseases, perinatal disorders, pregnancy, prostate cancer, psychiatric disorders, pulmonary disorders, renal disorders, rheumatic diseases, stroke, wound healing, oral infections, periodontal disease, brain injury, trauma, neuronal inflammation, and/or women's health. Accordingly, some alternatives concern use of resolvimab or a fragment thereof, as set forth above, in a medicament. In some alternatives, the resolvimab or a fragment thereof, as set forth above is used for the purpose of inhibiting, ameliorating, or treating inflammation, anaphylactic reactions, arthritis, asthma, atherosclerosis, bone diseases, breast cancer, cancer, cardiovascular diseases, colon cancer, degenerative neurologic disorders, dementia, diabetes mellitus, eye diseases, gastrointestinal disorders, genitourinary disorders, hematologic disorders, hepatobiliary disorders, hypertension, infectious diseases, leukemia/lymphoma, lung cancer, metabolic disorders, neurological disorders, neuromuscular disorders, obesity/eating disorders, parasitic diseases, perinatal disorders, pregnancy, prostate cancer, psychiatric disorders, pulmonary disorders, renal disorders, rheumatic diseases, stroke, wound healing, oral infections, periodontal disease, brain injury, trauma, neuronal inflammation, and/or women's health.

In certain embodiments, the resolvin biomimetic peptide (e.g., resolvimab or a fragment thereof) or composition comprising the biomimetic peptide is administered topically, for example to the subject's oral cavity. In other embodiments, the resolvin biomimetic peptide (e.g., resolvimab or a fragment thereof) or composition comprising the biomimetic peptide (e.g., an oral product such as a mouth wash, rinse, gel, or tooth paste) is administered enterally, for example orally.

In another aspect, embodiments concern a pharmaceutical composition comprising at least one of the aforementioned resolvin biomimetic peptides (e.g., resolvimab or a fragment thereof), optionally, at least one additional therapeutic agent, and at least one pharmaceutically acceptable carrier or excipient.

In certain embodiments, a pharmaceutical composition further comprises at least one additional therapeutic agent selected from the group consisting of anticancer, chemotherapeutic, analgesics, anesthetics, antimicrobial agents, antibacterial agents, antiviral agents, antifungal agents, antibiotics, anti-inflammatory agents, antioxidants, antiseptic agents, or immunomodulatory agents, and combinations thereof.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A-D depict graphs showing the profile of resolvin mimetic antibody reactivity on $CHO^{ERV-1+}$ cells analyzed by flow cytometry. Secondary antibody (anti-mouse) Fitc-labeled antibodies were incubated with cell-antibody for 30 min at room temperature. Quantification of positive binding was evaluated by flow cytometry. FIG. 1A shows ERV-1 overexpressing cells incubated with cells only and isotype matched control antibodies showing no or minimal signals. FIGS. 1B-D antibody binding to ERV-1/CHO cells of resolvimab clones: C1, C2, C3, C4, and C5.

FIGS. 2A-B depict calcium signaling through antibody-ERV-1 receptor. FIG. 2A is a cartoon depiction of resolvimab binding on downstream intracellular calcium and inflammation resolution. FIG. 2B shows a bar graph depicting the results of a quantitative analysis of intracellular calcium mobilization as a function of resolvin mimetic antibody, C1-C5, stimulation of $CHO^{ERV-1+}$ cells. Data is expressed in delta RFU (resonance fluorescence units).

FIGS. 5A-D depict flow cytometry detection of immune complex formation among ERV-1 receptor and anti-ERV-1 antibodies. CHO-ERV+ cells were cultured for 48 hours for expression until human ERV-1 receptor was positive. FIG. 5A depicts isotype control clone and secondary labeling were negative controls for CHO membrane proteins and non-specific binding. FIGS. 5B-D depict hybridoma supernatant of 27 clones were detected by FITC anti-murine IgG secondary antibodies. Data is expressed as mean fluorescent intensity (n=5, mean±SD).

FIG. 9A shows representative gating of Ly6G cells: cells were gated for double positive CD11b-ERV-1 cells. FIG. 9C shows Cd11b positive cells: cells were gated for M2 monocytes by Arg-1/Egr-2 double positive cells. FIGS. 9B and 9D show quantification of % positive neutrophils or M2 monocytes after specific treatments: resolvin E1, chemerin, anti-ERV-1 Ab, isotype control and resolvimab clones (C1-C4). Values represent mean % positive cells (n=3, mean±SD).

FIG. 10A depicts the expression of double positive ERV1 receptor on human neutrophils. CD11b, and CXCR4 positive and negative, human peripheral blood neutrophils were quantified by flow cytometry. The overlap panel shows the heterogeneity found in type 2 diabetes. FIG. 10B: Murine neutrophil production was induced by peritoneal lavage model after zymosan injection (1 mg/ml). Differential leukocyte count was used to classify cell types from WT and db/db mice. Neutrophils, monocytes, macrophages, and lymphocytes were quantified through microscopy and differential leukocyte count after GIEMSA staining. Confirmation in flow cytometry immunolabeling demonstrated that most cells from peritoneal lavage were positive for CD11b+ Ly6G+. FIG. 10C: Regression analysis of positive co-expression association of CxCR4 high ERV1 high receptors. FIG. 10D: The kinetics of ERV-1 high neutrophils after expression in murine peritoneal lavage. Results are expressed as mean fluorescence intensity (A, n=41; B-D, n-4).

FIGS. 11A-B depict ERV-1 receptor assay development in custom ELISA: Panels show linear and sigmoid standard curves of BCA curve for quantification of custom ELISA designed to identify ERV-1 receptor concentration. FIG. 11C shows ERV-1 receptor expression; ERV-1 immobilized lysates were incubated on cell wells, quantitated by ELISA directed to ERV-1 receptor (wt, neutrophils from wt FVB background; db/db+/+, neutrophils from diabetic mice; CHO ERV-1+, cell line lysate positive for human ERV-15 1 receptor; n=4, mean±SD).

FIGS. 12A-D show aspects of the process of engineering antibody mimetics for the ERV-1 receptor. FIGS. 12A-B depict screening of hybridoma supernatant through human ERV-1 CHO cell lines. CHO-ERV+ cells were cultured for 48 hours for expression until human ERV-1 receptor was positive. Resulting human ERV1 lysates derived from CHO+ cells were immobilized on well plates at 1 mg/ml. Hybridoma supernatant derived from medium collected from 576 clones was hybridized with immobilized antigens. Flow cytometry was used to detect immune complex formation among ERV-1 receptor and anti-ERV-1 antibodies. FIG. 12A depicts an isotype control clone and secondary labeling, providing negative controls for CHO membrane proteins and non-specific binding. FIGS. 12B-C depict hybridoma supernatant of 27 clones detected by FITC/anti-murine IgG secondary antibodies. Data is expressed as mean fluorescence intensity (n=5, mean±SD). FIG. 12D shows combined data expressed as a heatmap.

FIG. 13A-B show ERV1 antibody clones selected for functional studies. FIG. 13A depicts a table of clones and their parental loci listed for in vitro and in vivo functional studies. FIG. 13B depicts isotyping characterization of the clones selected. Multiplex ID for the Immunoglobulin IgG isotype reveals IgG1 as the main subtype of positive binder clones. The figure shows clone Ids, parental hybridoma cells and isotypes. The engineered biomimetic antibodies, resolvimabs, aim to activate ERV-1 receptor function and resolution of inflammation.

FIG. 14A-B show genomic sequencing of ERV-1 biomimetic antibodies. FIG. 14A depicts DNA sequences 1G12_G8-2_C3-VH, 5G4_F8-1_G5-VH, 5G4_F8-1_B7-VH, and 5G4_F8-1_C10-VH of human anti-ERV-1 monoclonal antibodies VH region as described in SEQ ID NOs: 1, 5, 9, and 13, respectively; FIG. 14B depicts DNA sequences 1G12_G8-2_C3-VK, 5G4_F8-1_G5-VK, 5G4_F8-1_B7-VK, and 5G4_F8-1_C10-VK of human anti-ERV-1 monoclonal antibodies VK regions as described in SEQ ID NOs: 3, 7, 11, and 15, respectively.

FIGS. 16A-C show functional activation of inflammation in vivo. Results after induction of inflammation by peritoneal lavage with zyomasan alone or in a combination with the reagents are shown. Total cells were collected at 12 hours on ERV-1 human receptor (h-ERV-1)-positive mice. FIG. 16A shows representative gating of Ly6G cells for double positive CD11b-ERV-1 labeling. FIG. 16B shows the reduction in the total number of neutrophils from diabetic mice from h-ERV-1 ratio to wild type h_ERV-1 mice when treated with resolvin E1, chemerin, anti-ERV-1 Ab, isotype control and resolvimab clones (C1-C4). Values represent mean % positive cells (n=4, mean±SD). FIG. 16C shows quantification of the percentage of each identified cell type after treatment of WT and diabetic mice, alongside GIEMSA stained micrographs demonstrating anti-inflammatory functions of the monoclonal antibody.

DETAILED DESCRIPTION

Figure 1C:
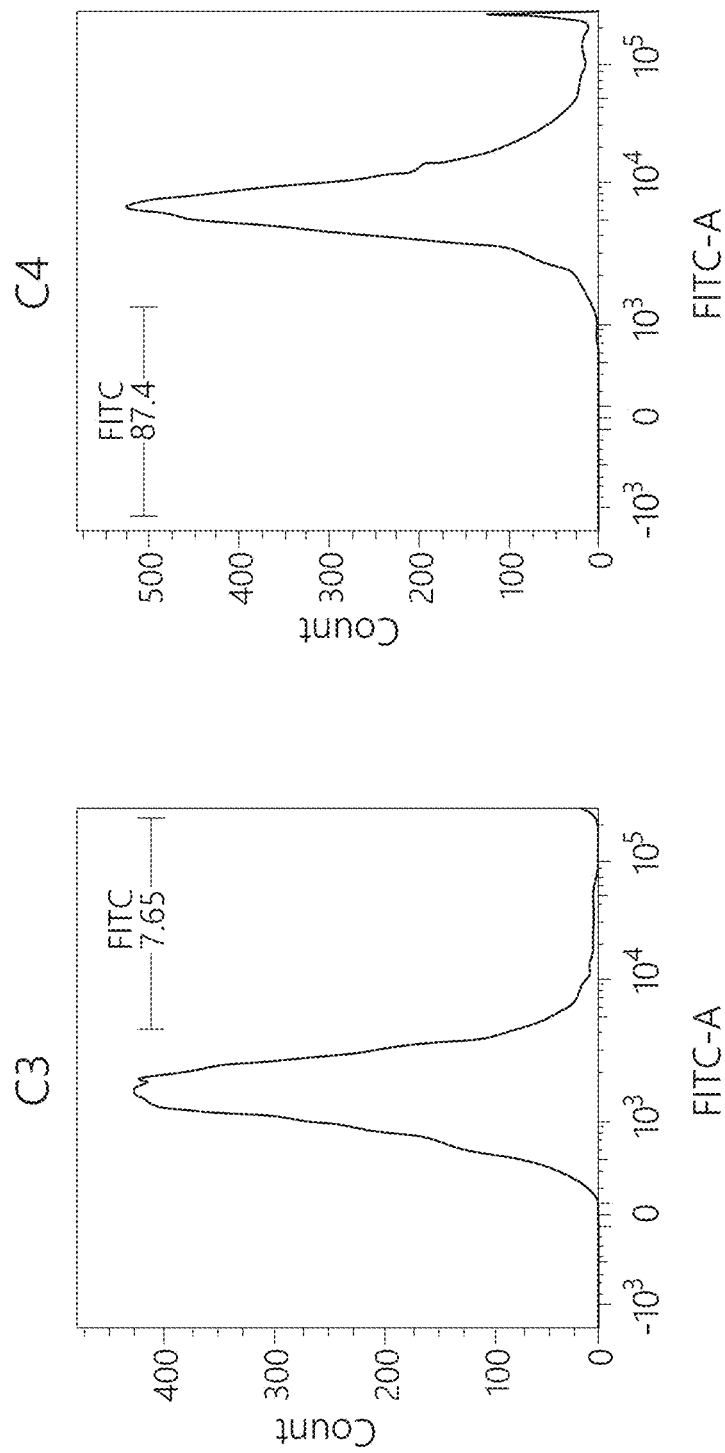
Figure 1D:
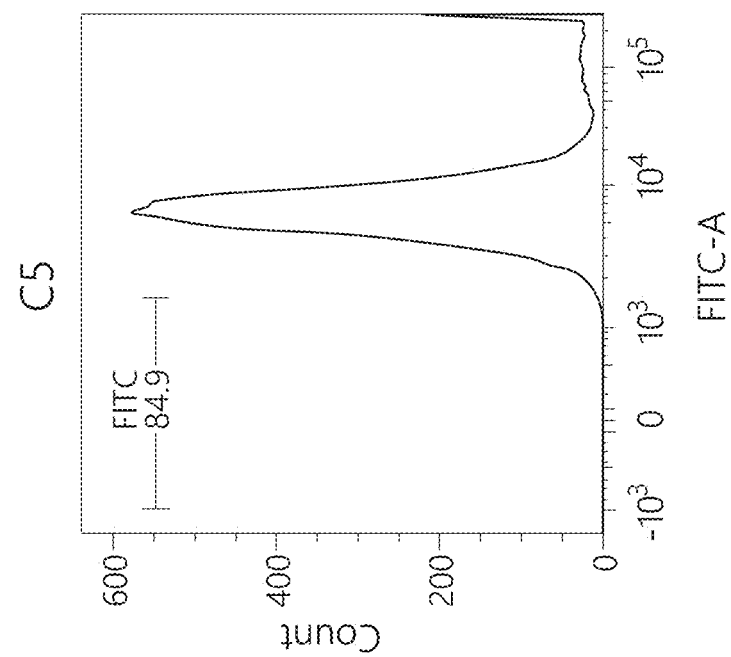
Figure 2B:
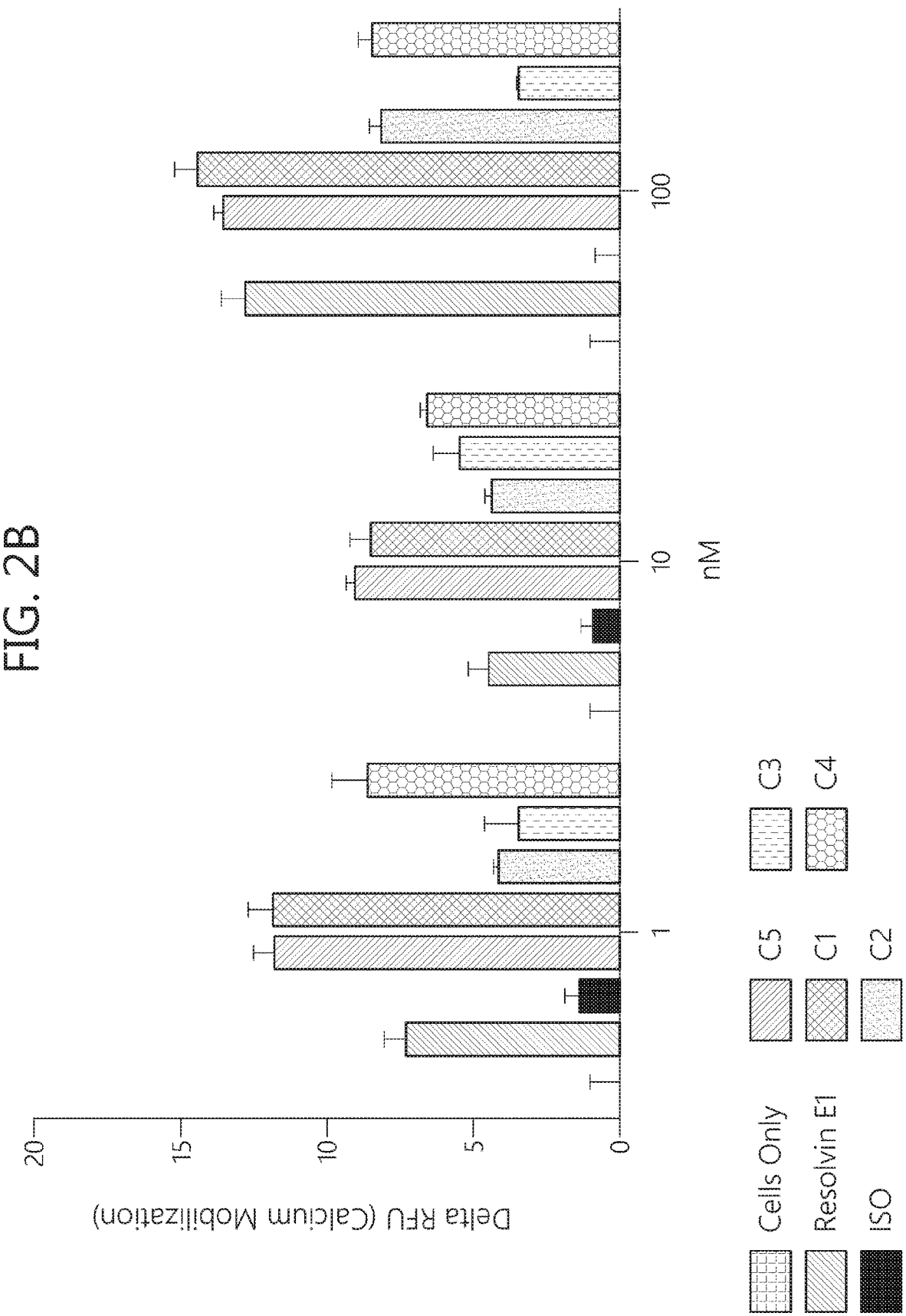

Aspects of the present invention provide compositions and methods for treating, inhibiting, and/or ameliorating inflammatory conditions in a vertebrate subject (human or animal). The inventive methods generally comprise administration of at least one resolvin mimetic peptide molecule, SEQ ID NOs: 2, 4, 6, 8, 10, 12, 14, and/or 16, or a biologically active variant thereof, or combinations thereof. In another aspect, the methods comprise administrating at least one resolvin mimetic antibody (e.g., resolvimab) or a binding fragment thereof. In certain embodiments, the resolvimab comprises a variable heavy chain (VH) sequence comprising an amino acid sequence selected from the group consisting of SEQ ID NO: 2, 6, 10, and 14, or biologically active variant thereof, or combination thereof. In certain embodiments, the resolvimab comprises a variable light chain (VK) sequence comprising an amino acid sequence selected from the group consisting of SEQ ID NO: 4, 8, 12, and 16, or biologically active variant thereof, or combination thereof.

In certain embodiments, the resolvimab (e.g., 1G12.G8-2.C3) comprises a variable heavy chain (VH) sequence comprising an amino acid sequence set forth in SEQ ID NO: 2 and a variable light chain (VK) sequence comprising an amino acid sequence set forth in SEQ ID NO: 4. In certain embodiments, the resolvimab (e.g., 1G12.G8-2.C3) comprises a variable heavy chain (VH) sequence comprising a nucleotide sequence set forth in SEQ ID NO: 1, which encodes a polypeptide sequence set forth in SEQ ID NO: 2, and a variable light chain (VK) sequence comprising nucleotide sequence set forth in SEQ ID NO: 3, which encodes a polypeptide sequence set forth in SEQ ID NO: 4. In certain embodiments, the resolvimab (e.g., 5G4.F8-1.G5) comprises a variable heavy chain (VH) sequence comprising an amino acid sequence set forth in SEQ ID NO: 6 and a variable light chain (VK) sequence comprising an amino acid sequence set forth in SEQ ID NO: 8. In certain embodiments, the resolvimab (e.g., 5G4.F8-1.G5) comprises a variable heavy chain (VH) sequence comprising a nucleotide sequence set forth in SEQ ID NO: 5, which encodes a polypeptide sequence set forth in SEQ ID NO: 6, and a variable light chain (VK) sequence comprising nucleotide sequence set forth in SEQ ID NO: 7, which encodes a polypeptide sequence set forth in SEQ ID NO: 8. In certain embodiments, the resolvimab (e.g., 5G4.F8-1B7) comprises a variable heavy chain (VH) sequence comprising an amino acid sequence set forth in SEQ ID NO: 10 and a variable light chain (VK) sequence comprising an amino acid sequence set forth in SEQ ID NO: 12. In certain embodiments, the resolvimab (e.g., 5G4.F8-1B7) comprises a variable heavy chain (VH) sequence comprising a nucleotide sequence set forth in SEQ ID NO: 9, which encodes a polypeptide sequence set forth in SEQ ID NO: 10, and a variable light chain (VK) sequence comprising nucleotide sequence set forth in SEQ ID NO: 11, which encodes a polypeptide sequence set forth in SEQ ID NO: 12. In certain embodiments, the resolvimab (e.g., 5G4.F8-1.C10) comprises a variable heavy chain (VH) sequence comprising an amino acid sequence set forth in SEQ ID NO: 14 and a variable light chain (VK) sequence comprising an amino acid sequence set forth in SEQ ID NO: 16. In certain embodiments, the resolvimab (e.g., 5G4.F8-1.C10) comprises a variable heavy chain (VH) sequence comprising a nucleotide sequence set forth in SEQ ID NO: 13, which encodes a polypeptide sequence set forth in SEQ ID NO: 14, and a variable light chain (VK) sequence comprising nucleotide sequence set forth in SEQ ID NO: 15, which encodes a polypeptide sequence set forth in SEQ ID NO: 16. Yet another embodiment includes aptamers that may be designed that bind the peptide molecule having an amino acid sequence selected from the group consisting of SEQ ID NOs: 2, 4, 6, 8, 10, 12, 14, and 16, or biologically active variant thereof, or combinations thereof.

The methods of the present invention, which are non-surgical, non-invasive and safe, can be used for the treatment, inhibition, amelioration and/or prevention of inflammation or disease states or conditions associated with inflammation including, but not limited to, allergic reactions, anaphylactic reactions, arthritis, asthma, atherosclerosis, bone diseases, breast cancer, cancer, cardiovascular diseases, colon cancer, degenerative neurologic disorders, dementia, diabetes mellitus, eye diseases, gastrointestinal disorders, genitourinary disorders, hematologic disorders, hepatobiliary disorders, hypertension, infectious diseases, leukemia/lymphoma, lung cancer, metabolic disorders, neurological disorders, neuromuscular disorders, obesity/eating disorders, parasitic diseases, perinatal disorders, pregnancy, prostate cancer, psychiatric disorders, pulmonary disorders, renal disorders, rheumatic diseases, stroke, wound healing, oral infections, periodontal disease, brain injury, trauma and neuronal inflammation, and women's health.

A. Definitions

In order that the present invention may be more readily understood, certain terms are first defined. Additional definitions are set forth throughout the detailed description.

The articles "a" and "an" are used herein to refer to one or to more than one (i.e., to at least one) of the grammatical object of the article. By way of example, "an element" means one element or more than one element.

As used herein, the term "administering" means providing a pharmaceutical agent or composition to a subject, and includes, but is not limited to, administering by a medical professional and self-administering.

The term "ERV1" is used interchangeably with ChemR23, ChemerinR, and RVER1. EVR1 is a G protein-coupled receptor Chemokine like receptor 1 expressed in innate immune cells (neutrophils and monocytes) and most cells of the human body. The lipid mediator resolvin E1 (RvE1) is known to activate cell signaling through the ERV1 receptor (Arita et al. (2005) J. Exp Med 201(5):713-722).

As used herein, "resolvin mimetic" is used interchangeably with an anti-ERV1 antibody, resolvimab, or biologically active antibody fragment thereof. The resolvin mimetic may comprise a peptide, aptamer directed to the peptide, polypeptide, or a nucleic acid encoding the polypeptide.

In certain embodiments, the resolvin mimetics are synthetically derived or recombinantly made, and may comprise additional modifications (e.g., mutations, substitutions, linkage attachments, chemical modifications, fusion tags, conjugations, and the like). The resolvin mimetics are non-naturally occurring, and differ from their natural counterparts, in markedly enhancing intracellular calcium mobilization or signaling and promoting inflammation resolution in a subject. Additional enhanced properties of the resolvin mimetics include enhanced resolution, excellent stability, increased bioavailability, increased half-life, improved binding affinity, and/or improved specificity.

The terms "individual" and "subject" are used herein interchangeably. They refer to a higher vertebrate, preferably a human or another mammal (e.g., a mouse, rat, rabbit, monkey, dog, cat, pig, cow, or horse) that can suffer from a disease state or condition for which administration of a resolvin biomimetic peptide is beneficial but may or may not have the disease state or condition. In many embodiments, the subject is suffering from or is susceptible to (e.g., exhibits a high or higher risk of developing) an inflammatory disorder, for example, a condition associated with chronic inflammation. In certain embodiments, the subject is a human being. The terms do not denote a particular age, and thus encompass adults, children and newborns.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers, for which the aforementioned resolvin mimetics can be used to treat or inhibit include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and/or Wilms tumor.

The terms "local" and "topical", when herein used to characterize the delivery, administration or application of a compound or composition, is meant to specify that the compound or composition is delivered, administered or applied directly to the site of interest (e.g., in the oral cavity for an oral inflammatory disorder such as periodontitis) for a localized effect. In certain embodiments, local or topical administration is effected without any significant absorption of components of the composition into the subject's blood stream.

As used herein, the term "effective amount" refers to any amount of a molecule, agent, factor or composition that is sufficient to fulfill its intended purpose(s) (e.g., the purpose may be to treat or prevent inflammation, for example, inflammation associated with periodontal disease). The term "treatment" is used herein to characterize a process/method that is aimed at (1) delaying the onset of a disease state or condition; (2) slowing down or stopping the progression, aggravation or deterioration of the symptoms of a clinical condition, (3) bringing about ameliorations of the symptoms of the condition; and/or (4) curing the condition. The treatment may be administered before the onset of the condition or it may be administered after initiation of the condition.

As used herein, "percent identity" between amino acid sequences is synonymous with "percent homology," which can be determined using the algorithm of Karlin and Altschul (*Proc. Natl. Acad. Sci.* USA 87, 2264-2268, 1990), modified by Karlin and Altschul (*Proc. Natl. Acad. Sci.* USA 90, 5873-5877, 1993). The noted algorithm is incorporated into the NBLAST and XBLAST programs of Altschul et al. (*J. Viol. Biol.* 215. 403-410, 1990). BLAST nucleotide searches are performed with the NBLAST program, score=100, wordlength=12, to obtain nucleotide sequences homologous to a polynucleotide described herein. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul. et al. (*Nucleic Acids Res.* 25, 3389-3402, 1997). When utilizing BLAST and Gapped BLAST programs, the default parameters of the respective programs (e.g., XBLAST and NBLAST) are used.

As used herein, an "immunomodulatory agent" may comprise one or more of aminocaproic acid, azathioprine, bromocriptine, chlorambucil, chloroquine, cyclophosphamide, cyclosporine, cyclosporine A, danazol, dehydroepiandrosterone, dexamethasone, etanercept, hydrocortisone, hydroxychloroquine, infliximab, meloxicam, methotrexate, mycophenylate mofetil, prednisone, sirolimus, or tacrolimus, or combinations thereof, or other immunomodulatory agents as are known in the art.

As used herein, an "anticancer agent" may comprise one or more of from 1-methyl-4-phenylpyridinium ion, 5-ethynyl-1-beta-D-ribofuranosylimidazole-4-carboxamide (EICAR), 5-fluorouracil, 9-aminocamptothecin, actinomycin D, asparaginase, bicalutamide, bis-chloroethylnitrosourea (BCNU), bleomycin, bleomycin A2, bleomycin B2, busulfan, camptothecin, carboplatin, carmustine, CB1093, chlorambucil, cisplatin, crisnatol, cyclophosphamide, cytarabine, cytosine arabinoside, cytoxan, dacarbazine, dactinomycin, daunorubicin, decarbazine, deferoxamine, demethoxy-hypocrellin A, docetaxel, doxifluridine, doxorubicin, EB1089, epirubicin, etoposide, floxuridine, fludarabine, flutamide, gemcitabine, goserelin, hydroxyurea, idarubicin, ifosfamide, interferon-α, interferon-γ, irinotecan, KH1060, leuprolide acetate, lomustine, lovastatin, megestrol, melphalan, mercaptopurine, methotrexate, mitomycin, mitomycin C, mitoxantrone, mycophenolic acid, nitrogen mustard, nitrosourea, paclitaxel, peplomycin, photosensitizer Pe4, phthalocyanine, pirarubicin, plicamycin, procarbazine, raloxifene, raltitrexed, revlimid, ribavirin, staurosporine, tamoxifen, teniposide, thalomid, thapsigargin, thioguanine, tiazofurin, topotecan, treosulfan, trimetrexate, tumor necrosis factor, velcade, verapamil, verteporfin, vinblastine, vincristine, vinorelbine, or zorubicin, or combinations thereof, or any other anticancer agent as is or may be known in the art.

As used herein, an "antiviral" agent may comprise one or more of pencicyclovir, valacyclovir, gancicyclovir, foscarnet, ribavirin, idoxuridine, vidarabine, trifluridine, acyclovir, famcicyclovir, amantadine, rimantadine, cidofovir, antisense oligonucleotide, immunoglobulin, and interferon. An antibacterial agent may be selected from chloramphenicol, vancomycin, metronidazole, trimethoprin, sulfamethazole, quinupristin, dalfopristin, rifampin, spectinomycin, or nitrofurantoin or combinations thereof, or any other antiviral agent as is or may be known in the art.

As used herein, an "antifungal" agent may comprise one or more of amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, benzoic acid, ciclopirox, flucytosine, griseofulvin, haloprogin, tolnaftate, undecylenic acid, crystal violet, balsam of peru, ciclopirox olamine, piroctone olamine, zinc pyrithione, or selenium sulfide or combinations thereof, or any other antifungal agent as is or may be known in the art.

As used herein, an "antiparasitic" agent may comprise one or more of mebendazole, pyrantel pamoate, thiabendazole, diethylcarbamazine, ivermectin, niclosamide, praziquantel, albendazole, rifampin, amphotericin B, melarsoprol, eflornithine, metronidazole, tinidazole, or miltefosine or combinations thereof, or any other antiparasitic agent as is or may be known in the art.

As used herein, a "chemotherapeutic" agent may comprise one or more of a small molecule receptor antagonist such as vatalanib, SU 11248 or AZD-6474, EGFR or HER2 antagonists such as gefitinib, erlotinib, CI-1033 or Herceptin, antibodies such as bevacizumab, cetuximab, rituximab, DNA alkylating drugs such as cisplatin, oxaliplatin or carboplatin, anthracyclines such as doxorubicin or epirubicin, an antimetabolite such as 5-FU, pemetrexed, gemcitabine or capecitabine, a camptothecin such as irinotecan or topotecan, an anti-cancer drug such as paclitaxel or docetaxel, an epipodophyllotoxin such as etoposide or teniposide, a proteasome inhibitor such as bortezomib or anti-inflammatory drugs such as celecoxib or rofecoxib, optionally in form of the pharmaceutically acceptable salts, in form of the hydrates and/or solvates and optionally in the form of the individual optical isomers, mixtures of the individual enantiomers or racemates thereof. In some embodiments, the chemotherapeutic agent is selected from the group consisting of a small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, a dual EGFR/HER2 antagonist such as gefitinib, erlotinib, CI-1033 or GW-2016, an EGFR antagonist such as iressa (ZD-1839), tarceva (OSI-774), PKI-166, EKB-569, HKI-272 or herceptin, an antagonist of the mitogen-activated protein kinase such as BAY-43-9006 or BAY-57-9006, a quinazoline derivative such as 4-[(3-chloro-4-fluorophenypamino]-6-{[4-(N,N-dimethylamino)-1-oxo-2-bute-n-1-yl]amino}-7-((S)-tetrahydrofuran-3-yloxy)quinazoline or 4-[(3-chloro-4-fluoro-phenyl)amino]-6-{[4-(homomorpholin-4-yl)-1-oxo-2-bu-ten-1-yl]amino}-7-[(S)-(tetrahydrofuran-3-yl)oxy]-quinazoline, or a pharmaceutically acceptable salt thereof, a protein kinase receptor antagonist which is not classified under the synthetic small molecules such as atrasentan, rituximab, cetuximab, Avastin® (bevacizumab), IMC-1C11, erbitux (C-225), DC-101, EMD-72000, vitaxin, imatinib, a protein tyrosine kinase inhibitor which is a fusion protein such as VEGFtrap, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an ethyleneimine compound, an alkylsulphonate, daunorubicin, doxorubicin (adriamycin), liposomal doxorubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as propamidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), pemetrexed, tegafur/uracil, uracil mustard, fludarabine, gemcitabine, capecitabine, mercaptopurine, cladribine, thioguanine, methotrexate, pentostatin, hydroxyurea, or folic acid, a phleomycin, a bleomycin or a derivative or salt thereof, CHPP, BZPP, MTPP, BAPP, liblomycin, an acridine or a derivative thereof, a rifamycin, an actinomycin, adramycin, a camptothecin such as irinotecan (camptosar) or topotecan, an amsacrine or analogue thereof, a tricyclic carboxamide, an histonedeacetylase inhibitor such as SAHA, MD-275, trichostatin A, CBHA, LAQ824, or valproic acid, an anti-cancer drug from plants such as paclitaxel (taxol), docetaxel or taxotere, a vinca alkaloid such as navelbine, vinblastin, vincristin, vindesine or vinorelbine, a tropolone alkaloid such as colchicine or a derivative thereof, a macrolide such as maytansine, an ansamitocin or rhizoxin, an antimitotic peptide such as phomopsin or dolastatin, an epipodophyllotoxin or a derivative of podophyllotoxin such as etoposide or teniposide, a steganacin, an antimitotic carbamate derivative such as combretastatin or amphetinile, procarbazine, a proteasome inhibitor such as bortezomib, an enzyme such as asparaginase, pegylated asparaginase (pegaspargase) or a thymidine-phosphorylase inhibitor, a gestagen or an estrogen such as estramustine (T-66) or megestrol, an anti-androgen such as flutamide, casodex, anandron or cyproterone acetate, an aromatase inhibitor such as aminogluthetimide, anastrozole, formestan or letrozole, a GNrH analogue such as leuprorelin, buserelin, goserelin or triptorelin, an anti-estrogen such as tamoxifen or its citrate salt, droloxifene, trioxifene, raloxifene or zindoxifene, a derivative of 17.beta.-estradiol such as ICI 164,384 or ICI 182,780, aminoglutethimide, formestane, fadrozole, finasteride, ketoconazole, a LH-RH antagonist such as leuprolide, a steroid such as prednisone, prednisolone, methylprednisolone, dexamethasone, budenoside, fluocortolone or triamcinolone, an interferon such as interferon β, an interleukin such as IL-10 or IL-12, an anti-TNFα antibody such as etanercept, an immunomodulatory drug such as thalidomide, its R- and S-enantiomers and its derivatives, or revimid (CC-5013), a leukotrien antagonist, mitomycin C, an aziridoquinone such as BMY-42355, AZQ or EO-9, a 2-nitroimidazole such as misonidazole, NLP-1 or NLA-1, a nitroacridine, a nitroquinoline, a nitropyrazoloacridine, a "dual-function" nitro aromatic such as RSU-1069 or RB-6145, CB-1954, a N-oxide of nitrogen mustard such as nitromin, a metal complex of a nitrogen mustard, an anti-CD3 or anti-CD25 antibody, a tolerance induction agent, a biphosphonate or derivative thereof such as mannuronic acid or its derivatives (YM-529, Ono-5920, YH-529), zoledronic acid monohydrate, ibandronate sodium hydrate or clodronate disodium, a nitroimidazole such as metronidazole, misonidazole, benznidazole or nimorazole, a nitroaryl compound such as RSU-1069, a nitroxyl or N-oxide such as SR-4233, an halogenated pyrimidine analogue such as bromodeoxyuridine, iododeoxyuridine, a thiophosphate such as WR-272 1, a photo-chemically activated drug such as porfimer, photofrin, a benzoporphyrin derivative, a pheophorbide derivative, merocyanin 540 (MC-540) or tin etioporpurin, an ant-template or an anti-sense RNA or DNA such as oblimersen, a non-steroidal inflammatory drug such as acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, nifluminic acid, tolfenamic acid, diflunisal, flufenisal, piroxicam, tenoxicam, lomoxicam, nimesulide, meloxicam, celecoxib, rofecoxib, or a pharmaceutically acceptable salt of a non-steroidal inflammatory drug, a cytotoxic antibiotic, an antibody targeting the surface molecules of cancer cells such as apolizumab or 1D09C3, an inhibitor of metalloproteinases such as TIMP-1 or TIMP-2, Zinc, an inhibitor of oncogenes such as P53 and Rb, a complex of rare earth elements such as the heterocyclic complexes of lanthanides, a photo-chemotherapeutic agent such as PUVA, an inhibitor of the transcription factor complex ESX/DRIP130/Sur-2, an inhibitor of HER-2 expression, such as the heat shock protein HSP90 modulator geldanamycin and its derivative 17-allylaminogeldanamycin or 17-AAG, or a therapeutic agent selected from IM-842, tetrathiomolybdate, squalamine, combrestatin A4, TNP-470, marimastat, neovastat, bicalutamide, abarelix, oregovomab, mitumomab, TLK-286, alemtuzumab, ibritumomab, temozolomide, denileukin diftitox, aldesleukin, dacarbazine, floxuridine, plicamycin, mitotane, pipobroman, plicamycin, tamoxifen and testolactone. Preferred compounds include small molecule VEGF receptor antagonist such as vatalanib (PTK-787/ZK222584), SU-5416, SU-6668, SU-11248, SU-14813, AZD-6474, EGFR/HER2 antagonists such as CI-1033 or GW-2016, an EGFR antagonist such as iressa (gefitinib, ZD-1839), tarceva (erlotinib, OSI-774), PKI-166, EKB-569, HKI-272 or herceptin, an antagonist of the mitogen-activated protein kinase such as BAY-43-9006 or BAY-57-9006, atrasentan, rituximab, cetuximab, Avastin™ (bevacizumab), IMC-1C11, erbitux (C-225), DC-101, EMD-72000, vitaxin, imatinib, an alkylating agent or a platinum compound such as melphalan, cyclophosphamide, cisplatin, carboplatin, oxaliplatin, satraplatin, daunorubicin, doxorubicin (adriamycin), liposomal doxorubicin (doxil), epirubicin, idarubicin, a pyrimidine or purine analogue or antagonist or an inhibitor of the nucleoside diphosphate reductase such as cytarabine, 5-fluorouracile (5-FU), pemetrexed, tegafur/uracil, gemcitabine, capecitabine, mercaptopurine, methotrexate, an anti-cancer drug such as paclitaxel (taxol) or docetaxel, a vinca alkaloid such as navelbine, vinblastin, vincristin, vindesine or vinorelbine, an antimitotic peptide such as dolastatin, an epipodophyllotoxin or a derivative of podophyllotoxin such as etoposide or teniposide, a non-steroidal inflammatory drug such as meloxicam, celecoxib, rofecoxib, an antibody targeting the surface molecules of cancer cells such as apolizumab or ID09C3 or the heat shock protein HSP90 modulator geldanamycin and its derivative 17-allylaminogeldanamycin or 17-AAG.

As used herein, the term "physiologically acceptable salts or prodrugs" refers to salts or prodrugs that are, within the scope of sound medical judgment, suitable for use in contact with the tissues of patients without undue toxicity, irritation, allergic response, and the like, commensurate with a reasonable benefit/risk ratio, and effective for their intended use.

The term "salts" refers to any acid addition or base addition salt that retains the biological activity and properties of the corresponding free base or free acid, respectively, and that is not biologically or otherwise undesirable. Acid addition salts are formed with inorganic acids (e.g., hydrochloric, hydrobromic, sulfuric, nitric, phosphoric acids, and the like); and organic acids (e.g., acetic, propionic, pyruvic, maleic, malonic, succinic, fumaric, tartaric, citric, benzoic, mandelic, methanesulfonic, ethanesulfonic, p-toluenesulfonic, salicylic acids, and the life). Base addition salts can be formed with inorganic bases (e.g., sodium, potassium, lithium, ammonium, calcium, magnesium, zinc, aluminum salts, and the like) and organic bases (e.g., salts of primary, secondary, and tertiary amines, substituted amines including naturally-occurring substituted amines, cyclic amines and basic ion exchange resins, such as isopropylamine, trimethylamine, diethylamine, triethylamine, tripropylamine, ethanolamine, 2-dimethyl-aminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like).

The term "prodrug" refers to a compound that, upon in vivo administration, is metabolized or otherwise converted to the biologically, pharmaceutically or therapeutically active form of the compound. The prodrug may be designed to alter the metabolic stability or the transport characteristics of a compound, to mask side effects or toxicity, to improve the flavor of a compound and/or to alter other characteristics or properties of a compound. By virtue of knowledge of pharmacodynamic processes and drug metabolisms in vivo, once a pharmaceutically active compound is identified, those of skill in the pharmaceutical art generally can design prodrugs of the compound (Nogrady, "Medicinal Chemistry A Biochemical Approach", 1985, Oxford University Press: N.Y., pages 388-392). Procedures for the selection and preparation of suitable prodrugs are also known in the art.

As used herein, the term "pharmaceutically acceptable carrier or excipient" refers to a carrier medium or an excipient which does not interfere with the effectiveness of the biological activity of the active ingredients and which is not excessively toxic to the host at the concentrations at which it is administered. The term includes solvents, dispersion media, coatings, antibacterial and antifungal agents, isotonic agents, absorption delaying agents, and the like. The use of such media and agents for pharmaceutically active substances is well known in the art (see, for example, "Remington's Pharmaceutical Sciences", E. W. Martin, 18th Ed., 1990, Mack Publishing Co.: Easton, Pa., which is incorporated herein by reference in its entirety).

B. Resolvin Mimetic Antibody/Anti-ERV1 Antibody Compositions

Provided herein are compositions, methods, and kits comprising resolvin mimetic antibody, peptide, or biologically active fragments thereof, for the treatment, inhibition, amelioration and/or prevention of diseases and conditions for which enhanced inflammation resolution may be beneficial. Such diseases include, but not limited to, chronic inflammation, periodontal disease, type 2 diabetes, cardiovascular disease, and/or cancer.

In some embodiments, the Resolvin mimetic antibody is a resolvimab, or biologically active fragment thereof. In some embodiments, the Resolvin mimetic antibody is a polypeptide or a nucleic acid encoding a resolvimab. In some embodiments, the Resolvin mimetic antibodies are fragments or a portion of the resolvimab amino acid sequence of sufficient length to elicit a resolvin-specific inflammatory response. In certain embodiments, the resolvimab polypeptide also includes amino acids that do not correspond to the amino acid sequence (e.g., a fusion protein comprising a resolvimab amino acid sequence and an amino acid sequence corresponding to a non-resolvin protein or polypeptide). In some embodiments, the anti-ERV1-antibody, or biologically active fragment thereof, binds to the ERV1 receptor and activates downstream signaling. Such activation includes, but not limited to, activation of inflammation resolution, calcium mobilization, receptor internalization, and NF-κB downregulation of pro-inflammatory cytokines.

In some embodiments, the Resolvin mimetic antibody comprises nucleotide sequences and amino acid sequences set forth in Table 1.

Table 1 depicts antibody nucleotide sequences. Hybridoma cells of 4 positive clones (Clones 1-4; also referred to as C1-C4) were isolated and cell RNA was extracted. After cDNA synthesis on PCR, VH and VL regions were amplified and sequenced. Nucleotide sequencing was completed by DNA Sanger sequencing method. The same primer set was used for the DNA amplification for the cDNA strand. Nucleotide sequence of antibody clones with VH and Vk regions were aligned for C1-C4 clones.

TABLE 1

| | |
|---|---|
| VH (DNA) (345 bp) | GAGCTTGTGA TGCCTGGGGC TTCAGTGAAG CTGTCCTGCA AGGCTTCTGG CTACACCTTC ACCAGCTACT GGATGCACTG GGTGAAGCAG AGGCCTGGAC AAGGCCTTGA GTGGGTCGCA GAGATTGATC CTTCTGATAG TTATACTAAC TACAATCAAA AGTTCAAGGG CAAGGCCACA TTGACTGTAG ACAAATCCTC CAGCACAGCC TACATGCAGC TCAGCAGCCT GACATCTGAG GACTCTGCGG TCTATTACTG TGCAAGAGAT GGGGATATAT TAACTACGGT AGTAGCTAAG GGGTTTGTTT ACTGGGGCCA AGGGACTCTG GTCACTGTCT CTGCA (SEQ ID NO: 1) |
| VK (DNA) (312 bp) | CTCTCCCTGC CTGTCAGTCT TGGAGATCAA GCCTCCATCT CTTGCAGATC TAGTCAGACC ATTGTACATA GTAATGGAAA CACCTATTTA GAATGGTACC TGCAGAAACC AGGCCAGTCT CCAAAGCTCC TGATCTACAA AGTTTCCAAC CGATTTTCTG GGGTCCCAGA CAGGTTCAGT GGCAGTGGAT CAGGGACAGA TTTCACACTC AAGATCAGCA GAGTGGAGGC TGAGGATCTG GGAGTTTATT ACTGCTTTCA AGGTTCACAT GTTCCGTGGA CGTTCGGTGG AGGCACCAAG CTGGAAATCA AA (SEQ ID NO: 3) |
| VH (AA) (115 aa) | ELVMPGASVK LSCKASGYTF TSYWMHWVKQ RPGQGLEWVA EIDPSDSYTN YNQKFKGKAT LTVDKSSSTA YMQLSSLTSE DSAVYYCARD GDILTTVVAK GFVYWGQGTL VTVSA (SEQ ID NO: 2) |
| VK (AA) (104 aa) | LSLPVSLGDQ ASISCRSSQT IVHSNGNTYL EWYLQKPGQS PKLLIYKVSN RFSGVPDRFS GSGSGTDFTL KISRVEAEDL GVYYCFQGSH VPWTFGGGTK LEIK (SEQ ID NO: 4) |

Clone 2: 5G4.F8-1.G5 (as referred to as "5G4_F8-1_G5")

| | |
|---|---|
| VH (DNA) (372 bp) | GAGGTTCAGC TGCAGCAGTC TGGGGCTGAG CTTGTGATGC CTGGGGCTTC AGTGAAGCTG TCCTGCAAGG CTTCTGGCTA CACCTTCACC AGCTACTGGA TGCACTGGGT GAAGCAGAGG CCTGGACAAG GCCTTGAGTG GGTCGCAGAG ATTGATCCTT CTGATAGTTA TACTAACTAC AATCAAAAGT TCAAGGGCAA GGCCACATTG ACTGTAGACA AATCCTCCAG CACAGCCTAC ATGCAGCTCA GCAGCCTGAC ATCTGAGGAC TCTGCGGTCT ATTACTGTGC AAGAGATGGG GATATATTAA CTACGGTAGT AGCTAAGGGG TTTGTTTACT GGGGCCAAGG GACTCTGGTC ACTGTCTCTG CA (SEQ ID NO: 5) |
| VK (DNA) (312 bp) | CTCTCCCTGC CTGTCAGTCT TGGAGATCAA GCCTCCATCT CTTGCAGATC TAGTCAGACC ATTGTACATA GTAATGGAAA CACCTATTTA GAATGGTACC TGCAGAAACC AGGCCAGTCT CCAAAGCTCC TGATCTACAA AGTTTCCAAC CGATTTTCTG GGGTCCCAGA CAGGTTCAGT GGCAGTGGAT CAGGGACAGA TTTCACACTC AAGATCAGCA GAGTGGAGGC TGAGGATCTG GGAGTTTATT ACTGCTTTCA AGGTTCACAT GTTCCGTGGA CGTTCGGTGG AGGCACCAAG CTGGAAATCA AA (SEQ ID NO: 7) |
| VH (AA) (124 aa) | EVQLQQSGAE LVMPGASVKL SCKASGYTFT SYWMHWVKQR PGQGLEWVAE IDPSDSYTNY NQKFKGKATL TVDKSSSTAY MQLSSLTSED SAVYYCARDG DILTTVVAKG FVYWGQGTLV TVSA (SEQ ID NO: 6) |
| VK (AA) (104 aa) | LSLPVSLGDQ ASISCRSSQT IVHSNGNTYL EWYLQKPGQS PKLLIYKVSN RFSGVPDRFS GSGSGTDFTL KISRVEAEDL GVYYCFQGSH VPWTFGGGTK LEIK (SEQ ID NO: 8) |

Clone 3: 5G4.F8-1B7 (as referred to as "5G4_F8-1_B7")

| | |
|---|---|
| VH (DNA) (372 bp) | GAGGTGCAGC TGCAGCAGTC TGGGGCTGAG CTTGTGATGC CTGGGGCTTC AGTGAAGCTG TCCTGCAAGG CTTCTGGCTA CACCTTCACC AGCTACTGGA TGCACTGGGT GAAGCAGAGG CCTGGACAAG GCCTTGAGTG GGTCGCAGAG ATTGATCCTT CTGATAGTTA TACTAACTAC AATCAAAAGT TCAAGGGCAA GGCCACATTG ACTGTAGACA AATCCTCCAG CACAGCCTAC ATGCAGCTCA GCAGCCTGAC ATCTGAGGAC TCTGCGGTCT ATTACTGTGC AAGAGATGGG GATATATTAA CTACGGTAGT AGCTAAGGGG TTTGTTTACT GGGGCCAAGG GACTCTGGTC ACTGTCTCTG CA (SEQ ID NO: 9) |
| VK (DNA) (312 bp) | CTCTCCCTGC CTGTCAGTCT TGGAGATCAA GCCTCCATCT CTTGCAGATC TAGTCAGACC ATTGTACATA GTAATGGAAA CACCTATTTA GAATGGTACC TGCAGAAACC AGGCCAGTCT CCAAAGCTCC TGATCTACAA AGTTTCCAAC CGATTTTCTG GGGTCCCAGA CAGGTTCAGT GGCAGTGGAT CAGGGACAGA TTTCACACTC AAGATCAGCA GAGTGGAGGC TGAGGATCTG GGAGTTTATT ACTGCTTTCA AGGTTCACAT GTTCCGTGGA CGTTCGGTGG AGGCACCAAG CTGGAAATCA AA (SEQ ID NO: 11) |

TABLE 1-continued

```
VH (AA)      EVQLQQSGAE LVMPGASVKL SCKASGYTFT SYWMHWVKQR
(124 aa)     PGQGLEWVAE IDPSDSYTNY NQKFKGKATL TVDKSSSTAY
             MQLSSLTSED SAVYYCARDG DILTTVVAKG FVYWGQGTLV TVSA
             (SEQ ID NO: 10)
VK (AA)      LSLPVSLGDQ ASISCRSSQT IVHSNGNTYL EWYLQKPGQS
(104 aa)     PKLLIYKVSN RFSGVPDRFS GSGSGTDFTL KISRVEAEDL
             GVYYCFQGSH VPWTFGGGTK LEIK (SEQ ID NO: 12)

Clone 4: 5G4.F8-1.C10 (as referred to as "5G4_F8-1_C10")

VH (DNA)     GAAGTTAAGC TGGAGGAGTC TGGGGCTGAG CTTGTGATGC
             CTGGGGCTTC AGTGAAGCTG TCCTGCAAGG CTTCTGGCTA
             CACCTTCACC AGCTACTGGA TGCACTGGGT GAAGCAGAGG
             CCTGGACAAG GCCTTGAGTG GGTCGCAGAG ATTGATCCTT
             CTGATAGTTA TACTAACTAC AATCAAAAGT TCAAGGGCAA
             GGCCACATTG ACTGTAGACA AATCCTCCAG CACAGCCTAC
             ATGCAGCTCA GCAGCCTGAC ATCTGAGGAC TCTGCGGTCT
             ATTACTGTGC AAGAGATGGG GATATATTAA CTACGGTAGT
             AGCTAAGGGG TTTGTTTACT GGGGCCAAGG GACTCTGGTC
             (SEQ ID NO: 13)
VK (DNA)     CTCTCCCTGC CTGTCAGTCT TGGAGATCAA GCCTCCATCT
             CTTGCAGATC TAGTCAGACC ATTGTACATA GTAATGGAAA
             CACCTATTTA GAATGGTACC TGCAGAAACC AGGCCAGTCT
             CCAAAGCTCC TGATCTACAA AGTTTCCAAC CGATTTTCTG
             GGGTCCCAGA CAGGTTCAGT GGCAGTGGAT CAGGGACAGA
             TTTCACACTC AAGATCAGCA GAGTGGAGGC TGAGGATCTG
             GGAGTTTATT ACTGCTTTCA AGGTTCACAT GTTCCGTGGA
             CGTTCGGTGG AGGCACCAAG CTGGAAATCA AA (SEQ ID NO: 15)
VH (AA)      EVKLEESGAE LVMPGASVKL SCKASGYTFT SWMEIWVKQR
             PGQGLEWVAE IDPSDSYTNY NQKFKGKATL TVDKSSSTAY
             MQLSSLTSED SAVYYCARDG DILTTVVAKG FVYWGQGTLV
             (SEQ ID NO: 14)
VK (AA)      LSLPVSLGDQ ASISCRSSQT IVHSNGNTYL EWYLQKPGQS
             PKLLIYKVSN RFSGVPDRFS GSGSGTDFTL KISRVEAEDL
             GVYYCFQGSH VPWTFGGGTK LEIK (SEQ ID NO: 16)
```

In some embodiments of the methods, compositions, and kits provided herein, the resolvin mimetic antibody comprises a polypeptide comprising amino acid sequences at least 70%, 75%, 80%, 85%, 90%, 91%, 92%, 93%, 94%, 95%, 96%, 97%, 98% or 99% identical to the amino acid sequence selected from the group consisting of SEQ ID NOs: 2, 4, 6, 8, 10, 12, 14, and 16, or biologically active variant thereof, or combinations thereof. In some embodiments of the methods, compositions, and kits provided herein, the resolvin mimetic antibody has an amino acid sequence that consists essentially of the amino acid sequence set forth in SEQ ID NOs: 2, 4, 6, 8, 10, 12, 14, or 16, or biologically active variant thereof, or combinations thereof. In some embodiments of the methods, compositions, and kits provided herein, the resolvin mimetic antibody is encoded by a polynucleotide comprising a polynucleotide sequence at least 70%, 75%, 80%, 85%, 90%, 91%, 92%, 93%, 94%, 95%, 96%, 97%, 98% or 99% identical to the nucleotide sequence selected from the group consisting of SEQ ID NOs: 1, 3, 5, 7, 9, 11, 13, and 15, or biologically active variant thereof, or combinations thereof. In some embodiments of the methods, compositions, and kits provided herein, the resolvin mimetic antibody is encoded by a polynucleotide that consists essentially of the nucleotide sequence set forth in SEQ ID NOs: 1, 3, 5, 7, 9, 11, 13, or 15, or biologically active variant thereof, or combinations thereof.

In some embodiments of the methods, compositions and kits provided herein, the anti-ERV1 antibody comprises a polypeptide having an amino acid sequence that consists of 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 140, 150, 160, 170, 180, 190 or 200 of SEQ ID Nos: 2, 4, 6, 8, 10, 12, 14, or 16, or biologically active variant thereof, or combinations thereof consecutive amino acids that are at least 70%, 75%, 80%, 85%, 90%, 91%, 92%, 93%, 94%, 95%, 96%, 97%, 98% or 99% identical to an amino acid sequence for a resolvin mimetic. In some embodiments of the methods, compositions and kits provided herein, the anti-ERV1 antibody is encoded by a polynucleotide comprising a polynucleotide sequence that consists of 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 140, 150, 160, 170, 180, 190 or 200 of SEQ ID Nos: 1, 3, 5, 7, 9, 11, 13, or 15, or biologically active variant thereof, or combinations thereof consecutive amino acids that are at least 70%, 75%, 80%, 85%, 90%, 91%, 92%, 93%, 94%, 95%, 96%, 97%, 98% or 99% identical to an amino acid sequence for a resolvin mimetic.

In certain embodiments, the resolvimab comprises a variable heavy chain (VH) sequence having at least 70%, 75%, 80%, 85%, 90%, 91%, 92%, 93%, 94%, 95%, 96%, 97%, 98% or 99% sequence identity to an amino acid sequence selected from the group consisting of SEQ ID NO: 2, 6, 10, and 14, or biologically active variant thereof, or combination thereof. In certain embodiments, the resolvimab comprises a variable light chain (VK) sequence having at least 70%, 75%, 80%, 85%, 90%, 91%, 92%, 93%, 94%, 95%, 96%, 97%, 98% or 99% sequence identity to an amino acid sequence selected from the group consisting of SEQ ID NO: 4, 8, 12, and 16, or biologically active variant thereof, or combination thereof.

In certain embodiments, the resolvimab (e.g., 1G12.G8-2.C3) comprises a variable heavy chain (VH) sequence having at least 70%, 75%, 80%, 85%, 90%, 91%, 92%, 93%, 94%, 95%, 96%, 77%, 98% or 99% sequence identity to an amino acid sequence set forth in SEQ ID NO: 2 and a variable light chain (VK) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 4. In certain embodiments, the resolvimab (e.g., 1G12.G8-2.C3) comprises a variable heavy chain (VH) sequence having at least 70%, 75%, 80%, 85%, 90%, 91%, 92%, 93%, 94%, 95%, 96%, 97%, 98% or 99% sequence identity to a nucleotide sequence set forth in SEQ ID NO: 1, which encodes a polypeptide sequence having at least 70%, 75%, 80%, 85%, 90%, 91%, 92%, 93%, 94%, 95%, 96%, 97%, 98% or 99% sequence identity to the amino acid sequence set forth in SEQ ID NO: 2, and a variable light chain (VK) sequence having at least 70%, 75%, 80%, 85%, 90%, 91%, 92%, 93%, 94%, 95%, 96%, 97%, 98% or 99% sequence identity to a nucleotide sequence set forth in SEQ ID NO: 3, which encodes a polypeptide sequence having at least 70%, 75%, 80%, 85%, 90%, 91%, 92%, 93%, 94%, 95%, 96%, 97%, 98% or 99% sequence identity to the amino acid sequence set forth in SEQ ID NO: 4. In certain embodiments, the resolvimab (e.g., 5G4.F8-1.G5) comprises a variable heavy chain (VH) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 6 and a variable light chain (VK) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 8. In certain embodiments, the resolvimab (e.g., 5G4.F8-1.G5) comprises a variable heavy chain (VH) sequence having at least 70%, 75%, 80%, 85%, 90%, 91%, 92%, 93%, 94%, 95%, 96%, 97%, 98% or 99% sequence identity to a nucleotide sequence set forth in SEQ ID NO: 5, which encodes a polypeptide sequence having at least 70%, 75%, 80%, 85%, 90%, 91%, 92%, 93%, 94%, 95%, 96%, 97%, 98% or 99% sequence identity to an amino acid sequence set forth in SEQ ID NO: 6, and a variable light chain (VK) sequence having at least 70%, 75%, 80%, 85%, 90%, 91%, 92%, 93%, 94%, 95%, 96%, 97%, 98% or 99% sequence identity to a nucleotide sequence set forth in SEQ ID NO: 7, which encodes a polypeptide sequence having at least 70%, 75%, 80%, 85%, 90%, 91%, 92%, 93%, 94%, 95%, 96%, 97%, 98% or 99% sequence identity to an amino acid sequence set forth in SEQ ID NO: 8. In certain embodiments, the resolvimab (e.g., 5G4.F8-1B7) comprises a variable heavy chain (VH) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 10 and a variable light chain (VK) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 12. In certain embodiments, the resolvimab (e.g., 5G4.F8-1B7) comprises a variable heavy chain (VH) sequence having at least 70%, 75%, 80%, 85%, 90%, 91%, 92%, 93%, 94%, 95%, 96%, 97%, 98% or 99% sequence identity to a nucleotide sequence set forth in SEQ ID NO: 9, which encodes a polypeptide sequence having at least 70%, 75%, 80%, 85%, 90%, 91%, 92%, 93%, 94%, 95%, 96%, 97%, 98% or 99% sequence identity to the amino acid sequence set forth in SEQ ID NO: 10, and a variable light chain (VK) sequence having at least 70%, 75%, 80%, 85%, 90%, 91%, 92%, 93%, 94%, 95%, 96%, 97%, 98% or 99% sequence identity to nucleotide sequence set forth in SEQ ID NO: 11, which encodes a polypeptide sequence having at least 70%, 75%, 80%, 85%, 90%, 91%, 92%, 93%, 94%, 95%, 96%, 97%, 98% or 99% sequence identity to an amino acid sequence set forth in SEQ ID NO: 12. In certain embodiments, the resolvimab (e.g., 5G4.F8-1.C10) comprises a variable heavy chain (VH) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 14 and a variable light chain (VK) sequence having at least 70%, 75%, 80%, 85%, 90%, 91%, 92%, 93%, 94%, 95%, 96%, 97%, 98% or 99% sequence identity to an amino acid sequence set forth in SEQ ID NO: 16. In certain embodiments, the resolvimab (e.g., 5G4.F8-1.C10) comprises a variable heavy chain (VH) sequence having at least 70%, 75%, 80%, 85%, 90%, 91%, 92%, 93%, 94%, 95%, 96%, 97%, 98% or 99% sequence identity to a nucleotide sequence set forth in SEQ ID NO: 13, which encodes a polypeptide sequence having at least 70%, 75%, 80%, 85%, 90%, 91%, 92%, 93%, 94%, 95%, 96%, 97%, 98% or 99% sequence identity to an amino acid sequence set forth in SEQ ID NO: 14, and a variable light chain (VK) sequence having at least 70%, 75%, 80%, 85%, 90%, 91%, 92%, 93%, 94%, 95%, 96%, 97%, 98% or 99% sequence identity to nucleotide sequence set forth in SEQ ID NO: 15, which encodes a polypeptide sequence having at least 70%, 75%, 80%, 85%, 90%, 91%, 92%, 93%, 94%, 95%, 96%, 97%, 98% or 99% sequence identity to an amino acid sequence set forth in SEQ ID NO: 16. Yet another embodiment includes aptamers that may be designed that bind the peptide molecule having at least 70%, 75%, 80%, 85%, 90%, 91%, 92%, 93%, 94%, 95%, 96%, 97%, 98% or 99% sequence identity to an amino acid sequence selected from the group consisting of SEQ ID NOs: 2, 4, 6, 8, 10, 12, 14, and 16, or biologically active variant thereof, or combinations thereof.

In certain embodiments, the resolvimab comprises a variable heavy chain (VH) sequence comprising an amino acid sequence selected from the group consisting of SEQ ID NO: 2, 6, 10, and 14, or biologically active variant thereof, or combination thereof. In certain embodiments, the resolvimab comprises a variable light chain (VK) sequence comprising an amino acid sequence selected from the group consisting of SEQ ID NO: 4, 8, 12, and 16, or biologically active variant thereof, or combination thereof.

In certain embodiments, the resolvimab (e.g., 1G12.G8-2.C3) comprises a variable heavy chain (VH) sequence comprising an amino acid sequence set forth in SEQ ID NO: 2 and a variable light chain (VK) sequence comprising an amino acid sequence set forth in SEQ ID NO: 4. In certain embodiments, the resolvimab (e.g., 1G12.G8-2.C3) comprises a variable heavy chain (VH) sequence comprising a nucleotide sequence set forth in SEQ ID NO: 1, which encodes a polypeptide sequence set forth in SEQ ID NO: 2, and a variable light chain (VK) sequence comprising nucleotide sequence set forth in SEQ ID NO: 3, which encodes a polypeptide sequence set forth in SEQ ID NO: 4. In certain embodiments, the resolvimab (e.g., 5G4.F8-1.G5) comprises a variable heavy chain (VH) sequence comprising an amino acid sequence set forth in SEQ ID NO: 6 and a variable light chain (VK) sequence comprising an amino acid sequence set forth in SEQ ID NO: 8. In certain embodiments, the resolvimab (e.g., 5G4.F8-1.G5) comprises a variable heavy chain (VH) sequence comprising a nucleotide sequence set forth in SEQ ID NO: 5, which encodes a polypeptide sequence set forth in SEQ ID NO: 6, and a variable light chain (VK) sequence comprising nucleotide sequence set forth in SEQ ID NO: 7, which encodes a polypeptide sequence set forth in SEQ ID NO: 8. In certain embodiments, the resolvimab (e.g., 5G4.F8-1B7) comprises a variable heavy chain (VH) sequence comprising an amino acid sequence set forth in SEQ ID NO: 10 and a variable light chain (VK) sequence comprising an amino acid sequence set forth in SEQ ID NO: 12. In certain embodiments, the resolvimab (e.g., 5G4.F8-1B7) comprises a variable heavy chain (VH) sequence comprising a nucleotide sequence set forth in SEQ ID NO: 9, which encodes a polypeptide sequence set forth in SEQ ID NO: 10, and a variable light chain (VK) sequence comprising nucleotide sequence set forth in SEQ ID NO: 11, which encodes a polypeptide sequence set forth in SEQ ID NO: 12. In certain embodiments, the resolvimab (e.g., 5G4.F8-1.C10) comprises a variable heavy chain (VH) sequence comprising an amino acid sequence set forth in SEQ ID NO: 14 and a variable light chain (VK) sequence comprising an amino acid sequence set forth in SEQ ID NO: 16. In certain embodiments, the resolvimab (e.g., 5G4.F8-1.C10) comprises a variable heavy chain (VH) sequence comprising a nucleotide sequence set forth in SEQ ID NO: 13, which encodes a polypeptide sequence set forth in SEQ ID NO: 14, and a variable light chain (VK) sequence comprising nucleotide sequence set forth in SEQ ID NO: 15, which encodes a polypeptide sequence set forth in SEQ ID NO: 16. Yet another embodiment includes aptamers that may be designed that bind the peptide molecule having an amino acid sequence selected from the group consisting of SEQ ID NOs: 2, 4, 6, 8, 10, 12, 14, and 16, or biologically active variant thereof, or combinations thereof.

As is well-known to those skilled in the art, polypeptides having substantial sequence similarities can cause identical or very similar immune reaction in a host animal. Accordingly, in some embodiments, a derivative, equivalent, variant, fragment, or mutant of the resolvin mimetic antibody or fragment thereof can also suitable for the methods, compositions and kits provided herein.

In some embodiments, the altered polypeptide may have an altered amino acid sequence, for example by conservative substitution, yet still elicits inflammation resolution, and are considered functional equivalents. As used herein, the term "conservative substitution" denotes the replacement of an amino acid residue by another, biologically similar residue. It is well known in the art that the amino acids within the same conservative group can typically substitute for one another without substantially affecting the function of a protein. According to certain embodiments, the derivative, equivalents, variants, or mutants of the resolvin mimetic antibody are at least 85% homologous to a sequence set forth in SEQ ID NOs: 2, 4, 6, 8, 10, 12, 14, and 16, or biologically active variant thereof, or combinations thereof. In some embodiments, the homology is at least 90%, at least 95%, or at least 98%.

In some embodiments, provided herein is a nucleic acid encoding a resolvimab described herein, such as a DNA molecule encoding a resolvimab. In some embodiments the composition comprises an expression vector comprising an open reading frame encoding a resolvin mimetic antibody. In some embodiments, the resolvimab nucleic acid includes regulatory elements necessary for expression of the open reading frame. Such elements can include, for example, a promoter, an initiation codon, a stop codon, and a polyadenylation signal. In addition, enhancers can be included. These elements can be operably linked to a sequence that encodes the targeted cancer vaccine polypeptide.

Examples of promoters include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine, and human metalothionein. Examples of suitable polyadenylation signals include but are not limited to SV40 polyadenylation signals and LTR polyadenylation signals.

In addition to the regulatory elements required for expression, other elements may also be included in the nucleic acid molecule. Such additional elements include enhancers. Enhancers include the promoters described hereinabove. Preferred enhancers/promoters include, for example, human actin, human myosin, human hemoglobin, human muscle creatine and viral enhancers such as those from CMV, RSV and EBV.

In some embodiments, the nucleic acid can be operably incorporated in a carrier or delivery vector. Useful delivery vectors include but are not limited to biodegradable microcapsules, immuno-stimulating complexes (ISCOMs) or liposomes, and genetically engineered attenuated live carriers such as viruses or bacteria.

In some embodiments, the vector is a viral vector, such as lentiviruses, retroviruses, herpes viruses, adenoviruses, adeno-associated viruses, vaccinia viruses, baculoviruses, Fowl pox, AV-pox, modified vaccinia Ankara (MVA) and other recombinant viruses. For example, a vaccinia virus vector can be used to infect dendritic cells (DC).

C. Pharmaceutical Compositions

Provided herein are pharmaceutical compositions comprising at least one resolvin mimetic. Such pharmaceutical compositions can be useful as vaccine compositions for prophylactic and/or therapeutic treatment or inhibition of inflammation or inflammatory disorders. In some embodiments, the resolvimab, or biologically active fragment thereof, may be employed in combination with one or more carriers to allow more stability, different releasing properties in vivo, targeting to a specific site, or any other desired characteristic that will allow more effective delivery of the resolvimab, or biologically active fragment thereof, to a subject or a target in a subject.

Examples of carriers include, but are not limited to, liposomes, nanoparticles, microspheres, and/or microbubbles.

The resolvimab, or biologically active fragment thereof, either alone or in combination with one or more carriers, can be dispersed in a physiologically compatible carrier. As used herein, "physiologically compatible carrier" refers to a physiologically acceptable diluent including, but not limited to water, phosphate buffered saline, or saline, and, in some embodiments, includes another adjuvant.

Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight polypeptides (less than about 10 residues); proteins, such as albumin, gelatin or immunoglobulins; hydrophilic polymers, such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween, Pluronics, or PEG.

In another embodiment, the resolvimab, or biologically active fragment thereof, can be administered in combination with an adjuvant. Additional adjuvants may include, but are not limited to, monophosphoryl lipid A (MPL); LTK63, dimethyl dioctadecyl-ammonium bromide (DDA), lipophilic quaternary ammonium salt-DDA, Trehalose dimycolate and synthetic derivatives, DDA-MPL, DDA-TDM, DDA-TDB, IC-31, aluminum salts, aluminum hydroxyide, aluminum phosphate, potassium aluminum phosphate, Montanide ISA-51, ISA-720, microparticles, immuno stimulatory complexes, liposomes, virosomes, virus-like particles, CpG oligonucleotides, cholera toxin, heat-labile toxin from E. coli, lipoproteins, dendritic cells, IL-12, GM-CSF, nanoparticles; a combination of soybean oil, emulsifying agents, and ethanol to form a nanoemulsion; AS04, ZADAXIN, or combinations thereof.

Compositions to be used for in vivo administration must be sterile, which can be achieved by filtration through sterile filtration membranes, prior to or following lyophilization and reconstitution. Therapeutic compositions may be placed into a container having a sterile access port, for example, an intravenous solution bag or vial having a stopper pierceable by a hypodermic injection needle.

As described above, in certain embodiments, the presently disclosed subject matter also includes combination therapies. These additional agents may be administered separately, as part of a multiple dosage regimen, or they may be part of a single dosage form in a single composition.

By "in combination with" is meant the administration of one or more resolvimab, or biologically active fragment thereof, with one or more therapeutic agents either simultaneously, sequentially, or a combination thereof. Therefore, a subject administered a combination of one or more resolvimab, or biologically active fragment thereof, and/or therapeutic agents, can receive the resolvimab, or biologically active fragment thereof, as described herein, and one or more therapeutic agents at the same time (i.e., simultaneously) or at different times (i.e., sequentially, in either order, on the same day or on different days), so long as the effect of the combination of both agents is achieved in the subject. When administered sequentially, the agents can be administered within 1, 5, 10, 30, 60, 120, 180, or 240 minutes or longer of one another. In other embodiments, agents administered sequentially, can be administered within 1, 5, 10, 15, 20 or more days of one another.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered agent is not diminished by the sequential, simultaneous or separate administration of the subsequent agent(s).

The presently disclosed compositions comprising resolvimab, or biologically active fragment thereof, can be administered using a variety of methods known in the art depending on the subject and the particular disease, disorder, or condition being treated. The administering can be carried out by, for example, intravenous infusion; injection by intravenous, intraperitoneal, intracerebral, intramuscular, intraocular, intraarterial or intralesional routes; or topical or ocular application.

More particularly, as described herein, the resolvimab, or biologically active fragment thereof, can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The presently disclosed pharmaceutical compositions can be manufactured in a manner known in the art, e.g. by means of conventional mixing, dissolving, granulating, dragee-making, levitating, emulsifying, encapsulating, entrapping or lyophilizing processes.

More particularly, pharmaceutical compositions for oral use can be obtained through combination of resolvimab, or biologically active fragment thereof, with a solid excipient, optionally grinding a resulting mixture, and processing the mixture of granules, after adding suitable auxiliaries, if desired, to obtain tablets or dragee cores. Suitable excipients include, but are not limited to, carbohydrate or protein fillers, such as sugars, including lactose, sucrose, mannitol, or sorbitol; starch from corn, wheat, rice, potato, or other plants; cellulose, such as methyl cellulose, hydroxypropyl-methyl-cellulose, or sodium carboxymethyl cellulose; and gums including arabic and tragacanth; and proteins, such as gelatin and collagen; and polyvinylpyrrolidone (PVP:povidone). If desired, disintegrating or solubilizing agents, such as cross-linked polyvinyl pyrrolidone, agar, alginic acid, or a salt thereof, such as sodium alginate, also can be added to the compositions.

Dragee cores are provided with suitable coatings, such as concentrated sugar solutions, which also can contain gum arabic, talc, polyvinylpyrrolidone, carbopol gel, polyethylene glycol (PEG), and/or titanium dioxide, lacquer solutions, and suitable organic solvents or solvent mixtures. Dyestuffs or pigments can be added to the tablets or dragee coatings for product identification or to characterize the quantity of resolvimab, or biologically active fragment thereof, compositions, e.g., dosage, or different combinations of doses.

Pharmaceutical compositions suitable for oral administration include push-fit capsules made of gelatin, as well as soft, sealed capsules made of gelatin and a coating, e.g., a plasticizer, such as glycerol or sorbitol. The push-fit capsules can contain active ingredients admixed with a filler or binder, such as lactose or starches, lubricants, such as talc or magnesium stearate, and, optionally, stabilizers. In soft capsules, the resolvimab, or biologically active fragment thereof, can be dissolved or suspended in suitable liquids, such as fatty oils, liquid paraffin, or liquid polyethylene glycols (PEGs), with or without stabilizers. Stabilizers can be added as warranted.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al., J. Biomed. Mater. Res. 15:167, 1981; Langer, Chem. Tech. 12:98, 1982), ethylene vinyl acetate (Langer et al., Id), or poly-D-(−)-3-hydroxybutyric acid (EP 133,988A).

Pharmaceutical compositions for parenteral administration include aqueous solutions of the resolvimab, or biologically active fragment thereof. For injection, the presently disclosed pharmaceutical compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of resolvimab, or biologically active fragment thereof, compositions include fatty oils, such as sesame oil, or synthetic fatty acid esters, such as ethyl oleate or triglycerides, or liposomes. Optionally, the suspension also can contain suitable stabilizers or agents that increase the solubility of the compositions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and/or fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, or buffering agents, can be present. The pH of the presently disclosed topical composition can be adjusted to a physiologically acceptable range of from about 6.0 to about 9.0 by adding buffering agents thereto such that the composition is physiologically compatible with a subject's skin.

Regardless of the route of administration selected, the presently disclosed resolvimab, or biologically active fragment thereof, compositions are formulated into pharmaceutically acceptable dosage forms such as described herein or by other conventional methods known to those of skill in the art.

D. Therapeutic Methods

Actual dosage levels of the resolvin mimetic compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular composition comprising the resolvin mimetic of the presently disclosed subject matter, the route of administration, the time of administration, the duration of the treatment, other drugs and/or materials used in combination with the particular resolvin mimetic employed, the age, sex, weight, condition, general health and prior medical history of the patient being treated, and like factors well known in the medical arts.

A physician having ordinary skill in the art can readily determine and prescribe the effective amount of resolvin mimetic required. Accordingly, the dosage range for administration will be adjusted by the physician as necessary.

Generally, doses of resolvin mimetic will range from about 0.0001 to about 1000 mg per kilogram of body weight of the subject. In certain embodiments, the dosage is between about 1 µg/kg and about 500 mg/kg, more preferably between about 0.01 mg/kg and about 50 mg/kg.

For example, in certain embodiments, a dose can be 1, 5, 10, 15, 20, or 40 mg/kg or within a range defined by any two of the aforementioned doses. In certain embodiments, a dose can be 0.1, 0.5, 1.0, 1.5, 2.0, or 4.0 mg/kg. In certain embodiments, a dose can be 0.01, 0.05, 0.1, 0.15, 0.2, or 0.4 mg/kg. In certain embodiments, a dose can be 0.001, 0.005, 0.01, 0.015, 0.02, or 0.04 mg/kg. In certain embodiments, a dose can be 0.0001, 0.0005, 0.001, 0.0015, 0.002, or 0.004 mg/kg.

In certain aspects, provided herein is a method of treating, inhibiting or preventing inflammation or an inflammatory disorder in a subject in need thereof, the method comprising the steps of administering a therapeutically effective amount of at least one resolvin mimetic. In some embodiment, the methods comprising administering at least one, two, three, four, or five resolvin mimetics.

In certain embodiments, the methods provided herein may be combined with at least one therapeutic agent selected from the group consisting of anticancer, chemotherapeutic, analgesics, anesthetics, antimicrobial agents, antibacterial agents, antiviral agents, antifungal agents, antibiotics, anti-inflammatory agents, antioxidants, antiseptic agents, immunostimulating agents, and combinations thereof. In some embodiment, the methods comprising administering at least one, two, three, four, five, six, seven, or eight therapeutic agents. In some embodiments, the therapeutic agent is administered conjointly, in combination, subsequently, or prior to administering the resolvin mimetic.

The methods described herein can be administered to any subject in need thereof. As used herein, a "subject in need thereof" includes any subject who has an inflammatory disorder selected from the group consisting of allergic reactions, anaphylactic reactions, arthritis, asthma, atherosclerosis, bone diseases, breast cancer, cancer, cardiovascular diseases, colon cancer, degenerative neurologic disorders, dementia, diabetes mellitus, eye diseases, gastrointestinal disorders, genitourinary disorders, hematologic disorders, hepatobiliary disorders, hypertension, infectious diseases, leukemia/lymphoma, lung cancer, metabolic disorders, neurological disorders, neuromuscular disorders, obesity/eating disorders, parasitic diseases, perinatal disorders, pregnancy, prostate cancer, psychiatric disorders, pulmonary disorders, renal disorders, rheumatic diseases, stroke, wound healing, oral infections, periodontal disease, brain injury, trauma and neuronal inflammation, and women's health.

The pharmaceutical compositions disclosed herein may be delivered by any suitable route of administration, including orally and parenterally. In certain embodiments the pharmaceutical compositions are delivered generally (e.g., via oral or parenteral administration).

The dosage of the subject agent may be determined by reference to the plasma concentrations of the agent. For example, the maximum plasma concentration (Cmax) and the area under the plasma concentration-time curve from time 0 to infinity (AUC (0-4)) may be used. Dosages include those that produce the above values for Cmax and AUC (0-4) and other dosages resulting in larger or smaller values for those parameters.

Actual dosage levels of the active ingredients in the pharmaceutical compositions may be varied so as to obtain an amount of the active ingredient which is effective to achieve the desired therapeutic response for a particular subject, composition, and mode of administration, without being toxic to the subject.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the subject being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the agents employed in the pharmaceutical composition at levels lower than that required in order to achieve the desired therapeutic effect and gradually increase the dosage until the desired effect is achieved.

In general, a suitable daily dose of an agent described herein will be that amount of the agent which is the lowest dose effective to produce a therapeutic effect. Such an effective dose will generally depend upon the factors described above.

In certain aspects, the methods provided herein include administering to both human and non-human mammals. Veterinary applications also are contemplated. In some embodiments, the subject can be any living female organism in which an immune response can be elicited.

Examples of subjects include, without limitation, humans, livestock, dogs, cats, mice, rats, and transgenic species thereof.

In certain embodiments, the subject has a history of cancer and has been administered another mode of therapy. The other therapy may have included e.g., surgical resection, radiotherapy, chemotherapy, and/or other modes of immunotherapy whereby as a result of the other therapy, the subject presents no clinically measurable tumor. However, the subject can be one determined to be at risk for recurrence or progression of the cancer, either near the original tumor site, or by metastases. Such subjects can be further categorized as high-risk and low-risk subjects. The subdivision can be made on the basis of features observed before or after the initial treatment. These features are known in the clinical arts, and are suitably defined for each different cancer. Features typical of high risk subgroups are those in which the tumor has invaded neighboring tissues, or which show involvement of lymph nodes. Thus, for example, a pharmaceutical composition described herein can be administered to the subject to elicit an anti-cancer response primarily as a prophylactic measure against recurrence.

In some embodiments, the pharmaceutical composition can be administered at any time that is appropriate. For example, the administering can be conducted before or during traditional therapy of a subject having an inflammatory disorder. The administering also can be continued in a subject showing signs of recurrence.

In some embodiments, the pharmaceutical composition can be administered in a therapeutically or a prophylactically effective amount. Administering the pharmaceutical composition to the subject can be carried out using known procedures, and at dosages and for periods of time sufficient to achieve a desired effect.

In some embodiments, the pharmaceutical composition can be administered to the subject at any suitable site, for example a site that is distal to or proximal to an organ, cell, or target of interest. The route of administering can be parenteral, intramuscular, subcutaneous, intradermal, intraperitoneal, intranasal, intravenous (including via an indwelling catheter), via an afferent lymph vessel, or by any other route suitable in view of the neoplastic disease being treated and the subject's condition. Preferably, the dose will be administered in an amount and for a period of time effective in bringing about a desired response, be it eliciting the immune response or the prophylactic or therapeutic treatment of the neoplastic disease and/or symptoms associated therewith.

The pharmaceutically acceptable composition can be given subsequent to, preceding, or contemporaneously with other therapies including therapies that also elicit an immune response in the subject. For example, the subject may previously or concurrently be treated by chemotherapy, radiation therapy, and other forms of immunotherapy, such other therapies preferably provided in such a way so as not to interfere with the immunogenicity of the compositions described herein.

Administering can be properly timed by the care giver (e.g., physician, veterinarian), and can depend on the clinical condition of the subject, the objectives of administering, and/or other therapies also being contemplated or administered. In some embodiments, an initial dose can be administered, and the subject monitored for an immunological and/or clinical response. Suitable means of immunological monitoring include using subject's peripheral blood lymphocyte (PBL) as responders and neoplastic cells as stimulators. One or more doses subsequent to the initial dose can be given as appropriate, typically on a monthly, semi-monthly, or preferably a weekly basis, until the desired effect is achieved. Thereafter, additional booster or maintenance doses can be given as required, particularly when the immunological or clinical benefit appears to subside.

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1

The primary reactivity of several antibody constructs illustrates the feasibility of constructing Resolvin mimetic peptides. Briefly, Chinese Hamster Ovary (CHO) K1/CMKLR1/Ga15 cells were transfected with CMKLR1 gene for screening assay (gene Synonyms: ChemR23, CMKLR1, ERV-1, DEZ, MGC126106, MGC126105, Genbank Accession Number NM_00407). Cells were cultured with Ham's F12, 10% FBS, 200 µg/ml Zeocin, 100 µg/ml Hygromycin B at 37° C./5% CO2. Cell media was replaced every 2-3 days.

Example 2

The ability of antibody constructs to cause a cellular response by mobilizing intracellular calcium displays the functionality of the Resolvin mimetic peptides. To investigate calcium mobilization, cells were transferred to a 96-well plate at density of 60,000 cells per well in 80 µl of growth medium 18 hours prior to the day of experiment and maintained at 37° C./5% CO2.

After aspiration of the media, cells were labeled with the fluorescent probe, Calcium5 FLIPR (Medical Devices). After agonist treatment, detection of changes in fluorescence were detected by microplate reader and expressed as change in relative fluorescence units ($\Delta$RFU). The CHO cells were treated in vitro with antibody clones, RvE1 and Chemerin (1-10 nM) and read at intervals of 1-240 minutes. ERV1 receptor activation by agonist ligands, such as resolvimab, is calcium dependent.

Example 3: Material and Methods

1—Animals

Male diabetic db/db (homozygous), db/− (heterozygous) mice with background strain FVB (FVB.BKS(D)-Lepr$^{db}$/ChuaJ) and their age-matched non-diabetic wild type control mice were obtained from Jackson Laboratories (Bar Harbor, Me., USA).

2—ERV-1 and db/ERV-1 Transgenic Mice

The ERV-1 mice were produced as previously described (Gao et al, 2012). They were bred with db/− (heterozygous) mice in order to produce the F1 generation, ERV+db/−. The F1 generation mice were bred in order to produce db/EVR transgenic mice (diabetic with an overexpression of ERV-1). Four strains result from the breeding of ERV+db/− mice: wild type; ERV, db/db and db/ERV-1. All mouse experiments were in conformity with the standards of the Public Health Service Policy on Human Care and Use of Laboratory Animals, and were approved by the Institutional Animal Care and Use Committee of The Forsyth Institute.

3—Custom ERV-1 ELISA:

ERV-1 whole cell lysate was obtained from Chinese Hamster Ovary (CHO) K1/CMKLR1/Ga15 cells (ERV1+ CHO cells) or peritoneal neutrophils from db/db mice, ERV-1 transgenic mice or wild type (WT) mice. Cells were washed with PBS (4000 rpm for 20 min at 4C) and added 2 ml of sonication buffer (10 ml DW, 40 mM Tris-cl, 1 mM EDTA, 1 mM PMSF) and sonicated on ice (20 sec, 10 sec interval, 5 min). Upon sonication, lysate was transferred to individual tubes before centrifuge at 15000 rpm for 5 min at 4 C. Supernatant was removed and filtered transferred to 25 µl of each standard and sample into a microplate well. Plates were covered and incubated overnight at 2-8° C. After washing steps (4 times of 300 µl, 1×PBS-T, Sigma), plates were inverted and blotted on paper towels to remove remaining liquid. Plates were blocked with 200 µl 3% BSA (Sigma) before washing steps were repeated twice.

Lysate was incubated with primary anti-human ERV-1 antibody (Monoclonal Mouse IgG3 Clone #84939, R&D systems) and plates were incubated for 1 hr at 25° C. After four rounds of washing steps, wells were labeled with secondary antibodies (Anti-Human IgG HRP, use at 1:1,000, Dako, clone #P0214) and incubated for 1 hr at 25° C. To avoid false positive results, repeated washing steps were performed (4×) before detection. 1000 TMB-1 solution (KPL) Cat #53-00-03) was added to each well before incubation for 30 min at 25° C. 1000 TMB-1 solution (KPL) was added to each well before incubation for 30 min at 25° C. To stop the reaction, 1000 TMB stop solution (KPL) was added to all wells and samples were read using 450 nm wavelength. For quantifications samples were compared to BSA protein curve. Anti-ERV-1 clones from Hybridoma cells were screened trough this system (lysate) and flow cytometry (whole cells).

4—CHO Cell Culture

Recombinant Human ERV1 transfected into Chinese hamster ovarian cells were obtained from Genscript (CHO ERV1+). Briefly, Chinese Hamster Ovary (CHO) K1/CMKLR1/Ga15 cells were transfected with CMKLR1 gene for screening assay (gene Synonyms: ChemR23, CMKLR1, ERV-1, DEZ, MGC126106, MGC126105, Genbank Accession Number NM_00407). Cells were cultured in Ham's 12 medium supplemented with 10% fetal bovine serum (GIBCO), 100 U/ml of Zeocin and Hydromycin antimicrobials and maintained 37° C. in 5% CO2. Cell media was replaced every 2-3 days. Expression of ERV-1 receptor was measured through flow cytometry and PCR during passages.

5—Production of Antti-Human Monoclonal Antibodies Against ERV-1 Receptor

To prepare Anti-human ERV-1 antibodies, CHO-ERV-1 cells were immunized to mice following general immunizations schemes (Fishwild, 1994). Mice were 6-16 weeks of age upon first infusion of antigen/cells. Mice were prepared for monoclonal antibody production by boosting the antigen 2 days before sacrificing. Spleens were removed thereafter and splenocytes isolated and fused with 50% PEG (Sigma) to a mouse myeloma cell line (ATCC, CRL1581) using standard protocols. Typically, 20-30 fusions for each host were performed. Cells were plated at approximately $1 \times 10^5$/well in flat bottom plates, followed by 2 weeks incubation in selective medium containing 10% fetal bovine serum (ATCC) conditioned medium, 3-5% origen (IGEN) in DMEM (GIBCO) with high glucose plus 5 mM HEPES, 0.055 mM 2-mercaptothanol, 50 mg/mL gentamycin and 1×HAT (Sigman). After 1-2 weeks, cells were cultured medium in which HAT was replaced by HT. The resulting hybridomas were screened for the production of antigen-specific antibodies through ELISA and flow cytometry. Once extensive hybridoma growth occurred, medium was monitored usually after 10-14 days. Antibody-secreting hybridomas were replated and screened again. When positive for human ERV-1 receptor, monoclonal antibodies were subclones at least twice by limiting dilution. The stable subclones were then cultured in vitro to generate small amounts of antibodies in tissue culture medium for characterization.

6—Hybridoma Screening by Flow Cytometry

Expression levels of the cellular proteins were monitored by flow cytometry (FACS Aria II, BD Biosciences) and analyzed with FlowJo (Tree Star). CHO ERV1+ cells were incubated with anti-Fc receptor (BD) blocking antibody (5 µg/ml×106 cells, 15 min) and then labeled with anti-human ERV1 alexafluor 488-conjugated antibody (10 µg/ml×106 cells, 1 hour at RT) or supernatant anti-ERV-1 clones (1 ml×106 cells, 1 hour at RT) with anti-IgG alexafluor 488 (30 mins at 37° C., isotype control, R&D Systems).

7—Intracellular Calcium Signaling

To investigate calcium mobilization, CHO ERV1+ cells were transferred to a 96-well plate at density of 60,000 cells per well in 80 μl of growth medium 18 hours prior to the day of experiment and maintained at 37° C./5% CO2. After aspiration of the media, cells were labeled with the fluorescent probe, Calcium5 FLIPR (Medical Devices). After agonist treatment, detection of changes in fluorescence were detected by microplate reader and expressed as change in relative fluorescence units (ARFU). The CHO cells were treated in vitro with varying doses (1, nM, 10 nM, 100 nM) of anti-ERV-1 antibody clones, Resolvin E-1, isotype control and four resolvimab clones (C1-C4). ERV1 receptor activation by agonist ligands such as resolvimab is calcium dependent.

8—Cell Surface Marker Expression

Cells were extracted from peritoneal exudates collected after 12 hours of intraperitoneal injection of zymosan-A (1 mg/ml in PBS). Isolated cells were incubated with anti-Fc receptor (BD) blocking antibody (5 μg/ml×106 cells, 15 min) and then labeled with anti-human ERV1 alexafluor 488-conjugated antibody (10 μg/ml×106 cells, 1 hour at RT) or anti-IgG alexafluor 488 (isotype control, R&D Systems). Expression of ERV1 on neutrophils was evaluated by immunofluorescence and quantified by flow cytometry. ERV-1, F40/80 positive monocytes were stained with PE-conjugated anti-mouse Arg-1 and FITC-conjugated anti-mouse EGR- (10 μg/ml×106 cells, 1 hour at RT) (BD Biosciences).

9—IgG Isotyping

Hybridoma antibody isotypes were categorized according to differences in their amino acid sequence in the constant region (Fc) of the antibody heavy chains. The antibody isotypes IgG is further grouped into subclasses (e.g. human IgG1, IgG2, IgG3, IgG4) based on additional small differences in their amino acid heavy chain sequences. Ig Isotyping multiplex Kit (eBioscience) were used to investigate anti-IgG1, IgG2a, IgG2b, IgG2c or IgG3, IgA, and IgM as well as light chain kappa and lambda.

10—IgG VH/VK Sequencing

Monoclonal antibodies derived from hybridoma cells specific to human ERV-1 receptor were cultured at $5 \times 10^8$ confluence. Total RNA extracted and reverse transcriptase was added (46 units) and incubated at 42° C. for 1 hr. For amplification with a thermostable DNA polymerase and VH/VK primers.

A typical PCR cycle was 1 min at 95° C. (denature), 1 min at 30° C. (anneal), and 2 min at 72° C. (elongate). cDNA was prepared from each of five hybridoma derived clones and nucleotide was sequenced through SANGER after gel extraction.

11—Statistical Analysis

Results are expressed as mean±SEM. Statistical analysis was performed using Prism 6 (GraphPad). Wilcoxon Test and Student unpaired t test were used to compare measurements. Values of P≤0.05 were considered statistically significant.

Example 4: Results

Selection of Anti-Human ERV-1 Monoclonal Antibodies

Figure 3A:
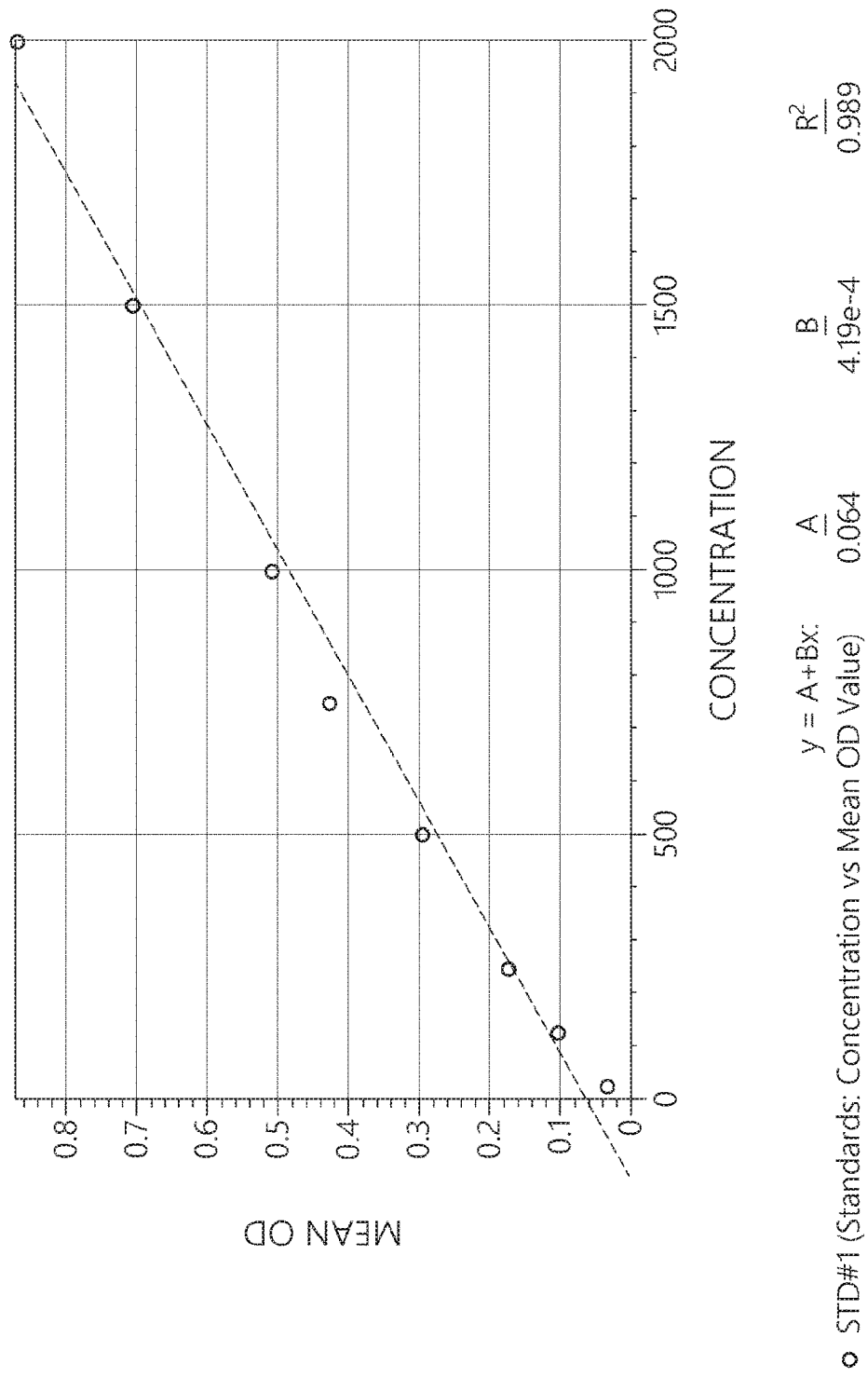
FIGS. 3A-B depict ERV-1 receptor assay development. Panel (A) shows linear and sigmoid standard curves of BCA curve for quantification of custom ELISA designed to identify ERV-1 receptor concentration. Panel (B) shows ERV-1 positive lysate were incubated on cell wells to quantify ERV-1 receptor expression (wt, neutrophils from wt FVB background; db/db+/+, neutrophils from diabetic mice; CHO ERV-1+, cell line lysate positive for human ERV-1 receptor; n=4, mean±SD).
Figure 3B:
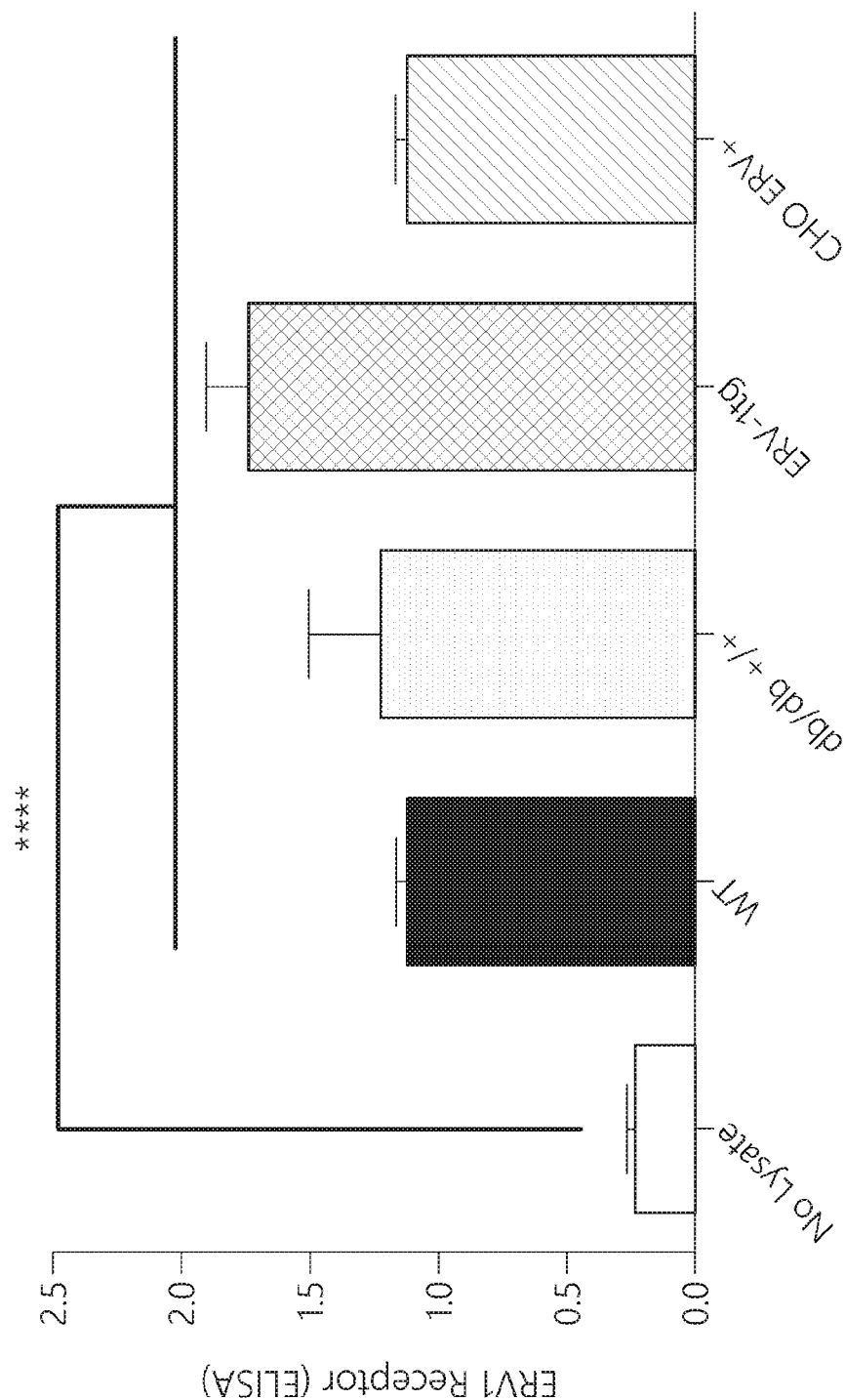

Hybridoma secreting a monoclonal antibody that bound with high affinity to ERV-1 were produced and subcloned for further binding and biological characterization. Once clones from each hybridoma, which retained the reactivity of parent cells, were selected in vitro and in vivo testing were used for final selection of the library. As determined by custom ELISA, anti-ERV-1 clones were selected. A custom ELISA assay was developed to screen for hybridomas that showed positive reactivity with ERV-1. Before quantification of the hibridoma and antigen interaction, the selection of positive lysate with a known anti-ERV-1 was performed. To understand the response of presence of the ERV-1 receptor, plates were incubated with four types of positive ERV-1 lysates including: wt, neutrophils from wt FVB background; db/db+/+, neutrophils from diabetic mice; CHO ERV-1+, cell line lysate positive for human ERV-1 receptor (FIGS. 3A-B). Results demonstrated that commercially available anti-ERV-1 antibody was able to interact and quantify with most lysates.

ELISA Screening of Resolvimab

Figure 4:
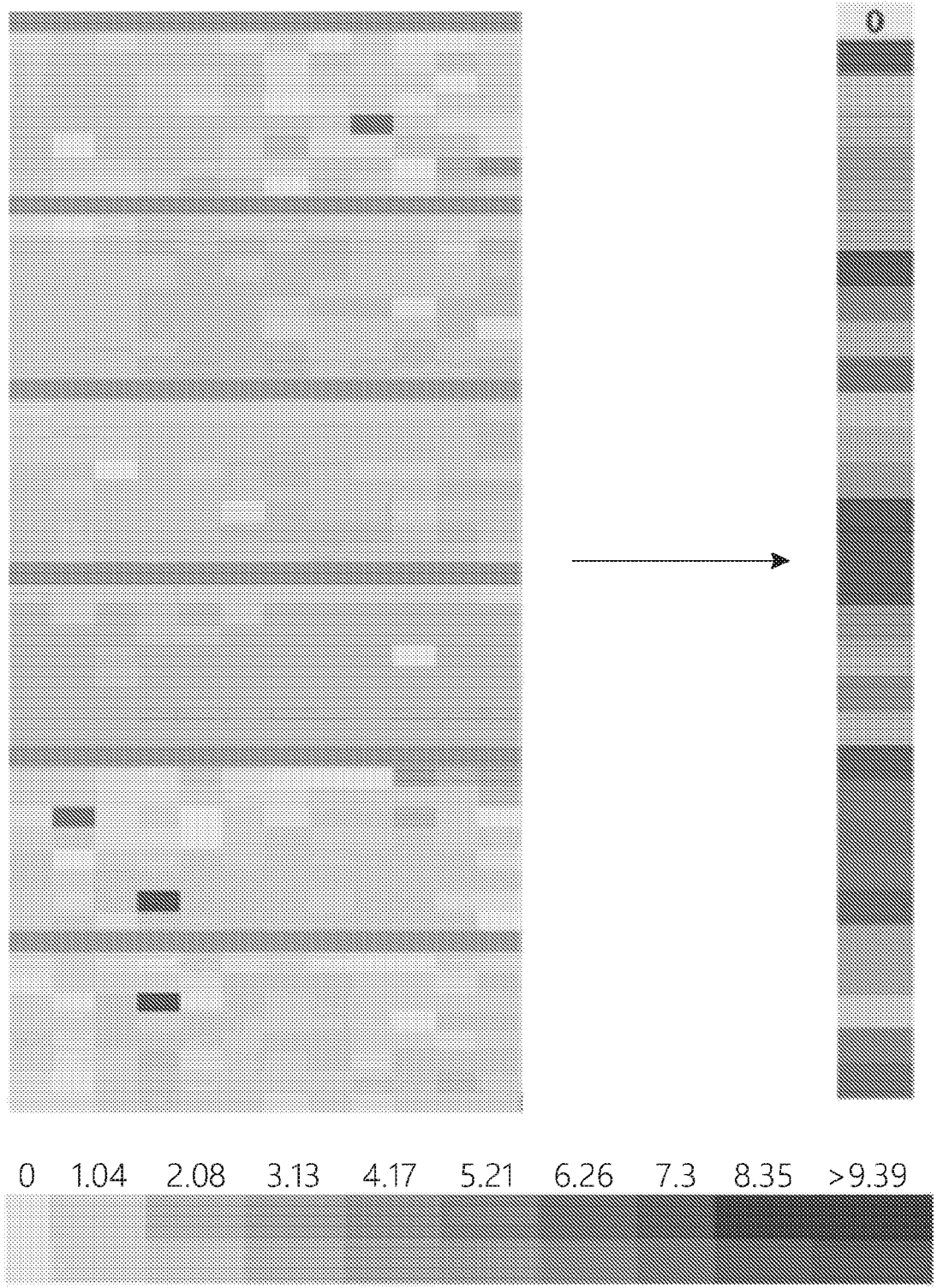
FIG. 4 depicts screening hybridoma supernatant through human ERV-1 ELISA. Human ERV1 lysate derived from CHO+ cells were immobilized on well plates at 1 mg/ml. Hybridoma supernatant derived from medium collected from 576 clones was hybridized with immobilized antigens. Shown is a heatmap of positive binders were identified by anti-IgG-HRP labeled antibodies and measured by OD, and parental selection of clones of highest binders went through sub-cloning with enrichment of the positivity. Data is represented by heatmaps (n=3, mean±SD).
Figure 5B:
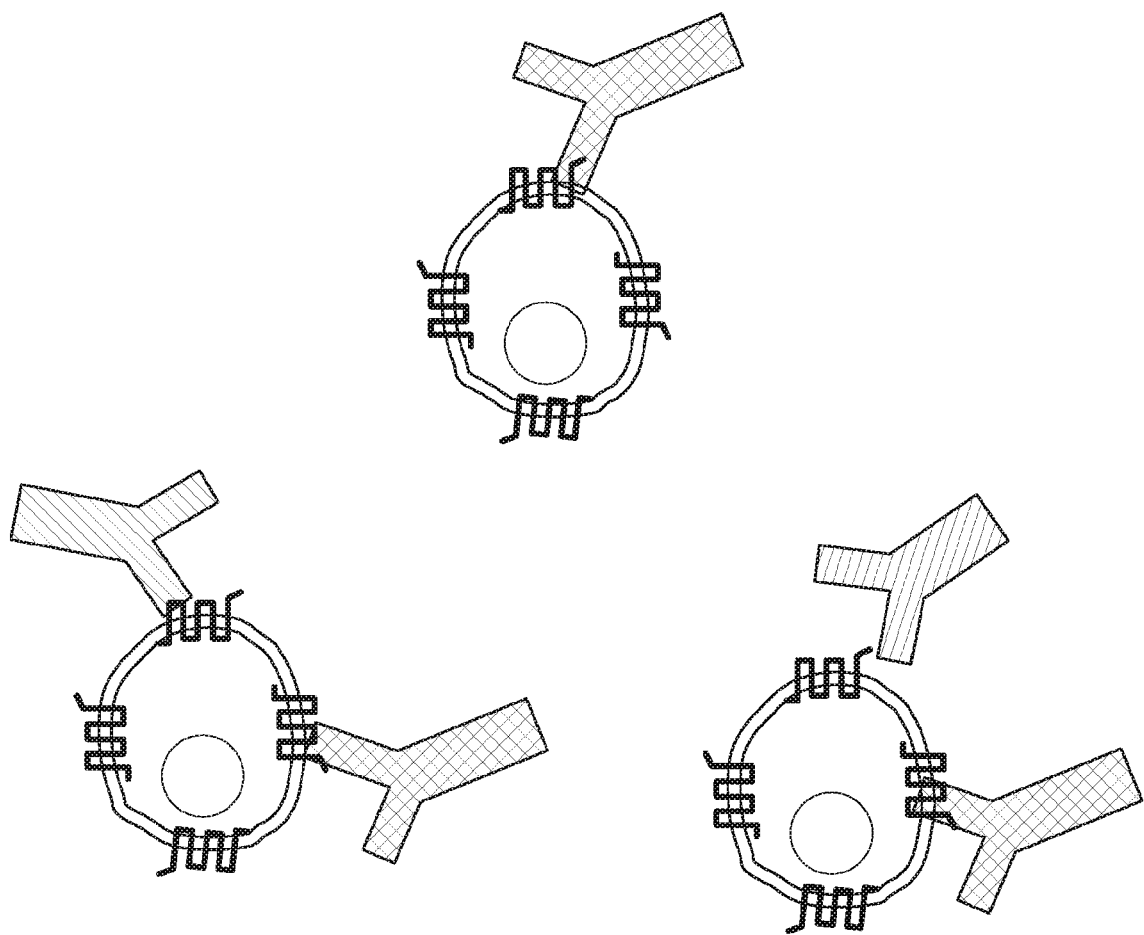
Figure 5C:
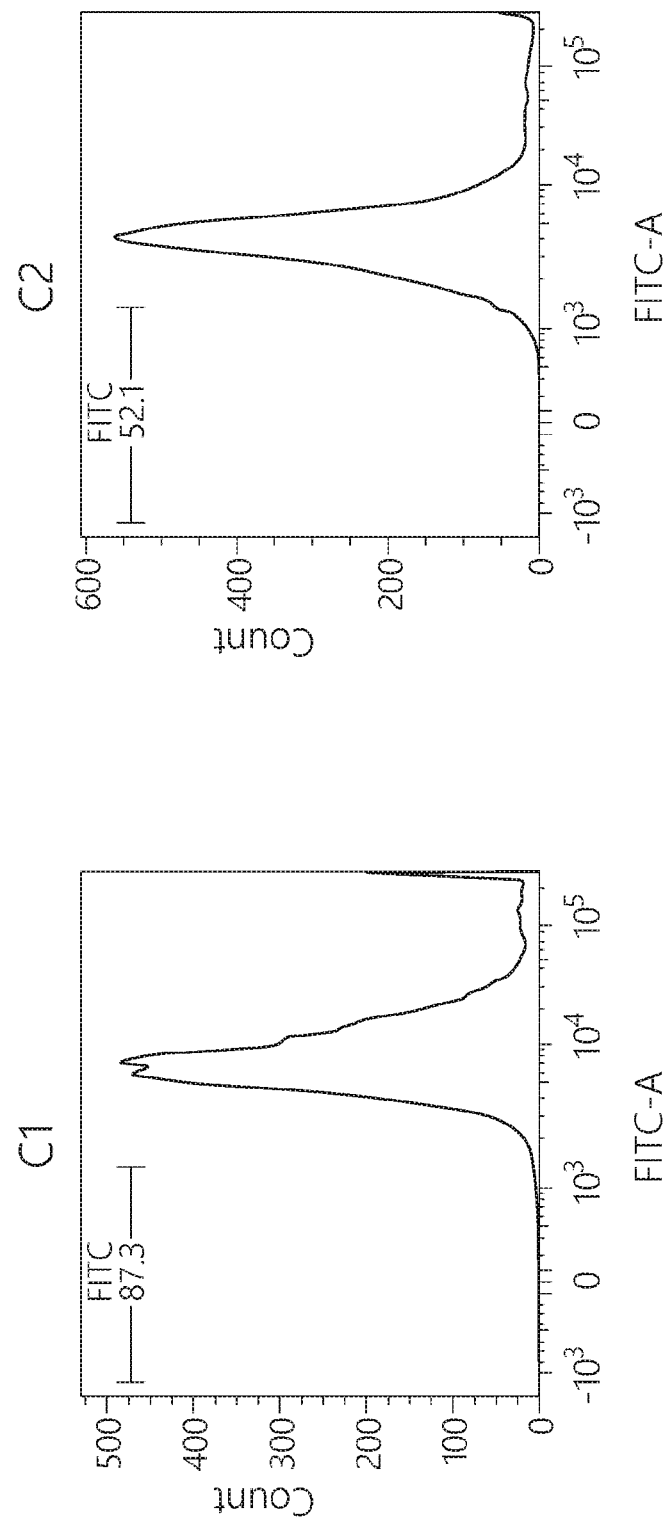
Figure 5D:
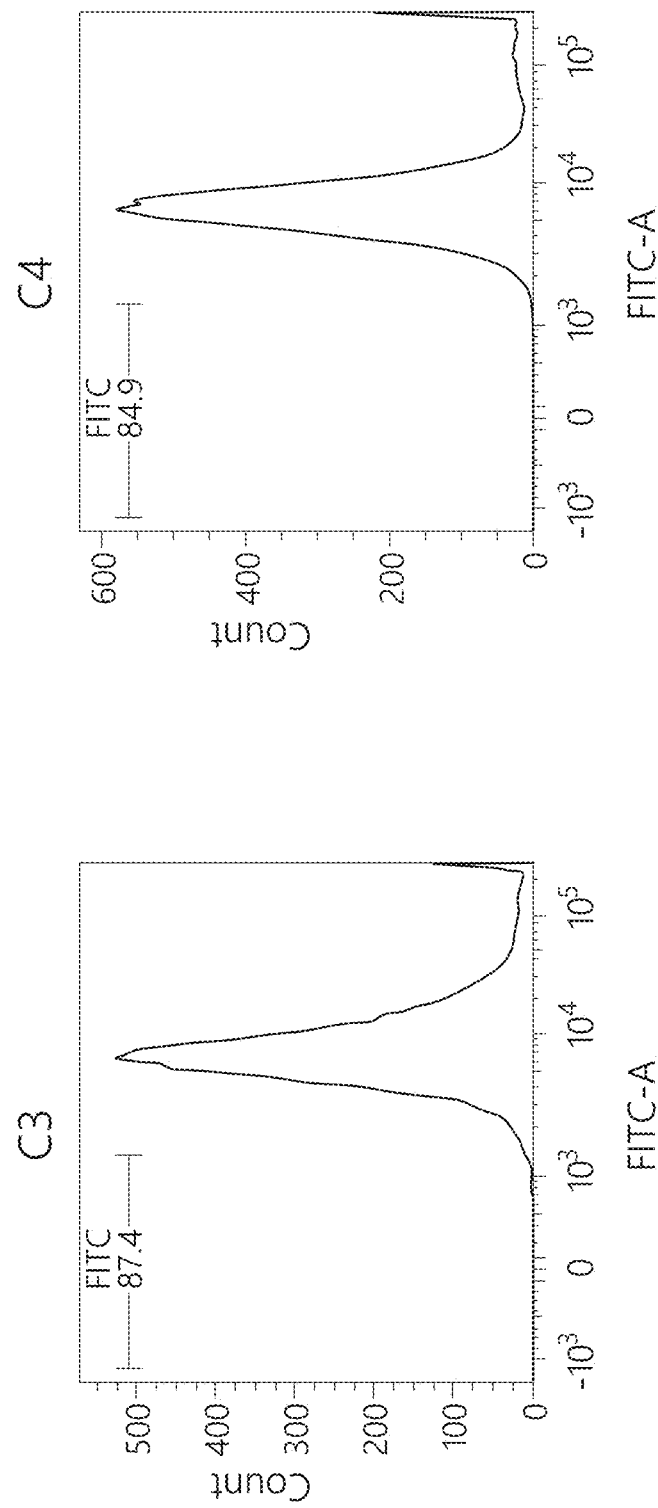
Figure 12C:
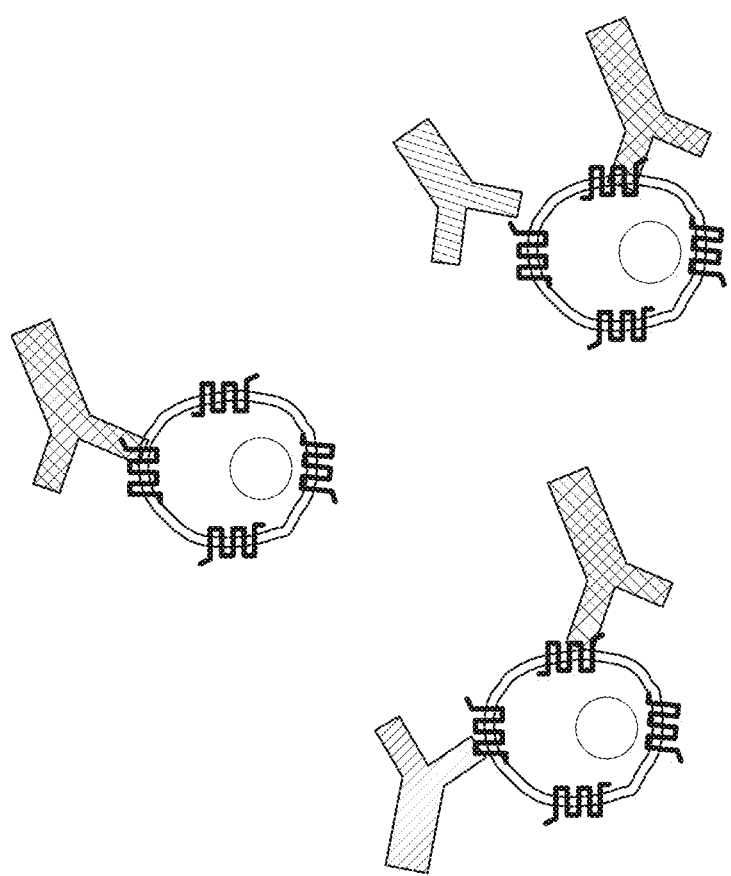
Figure 12D:
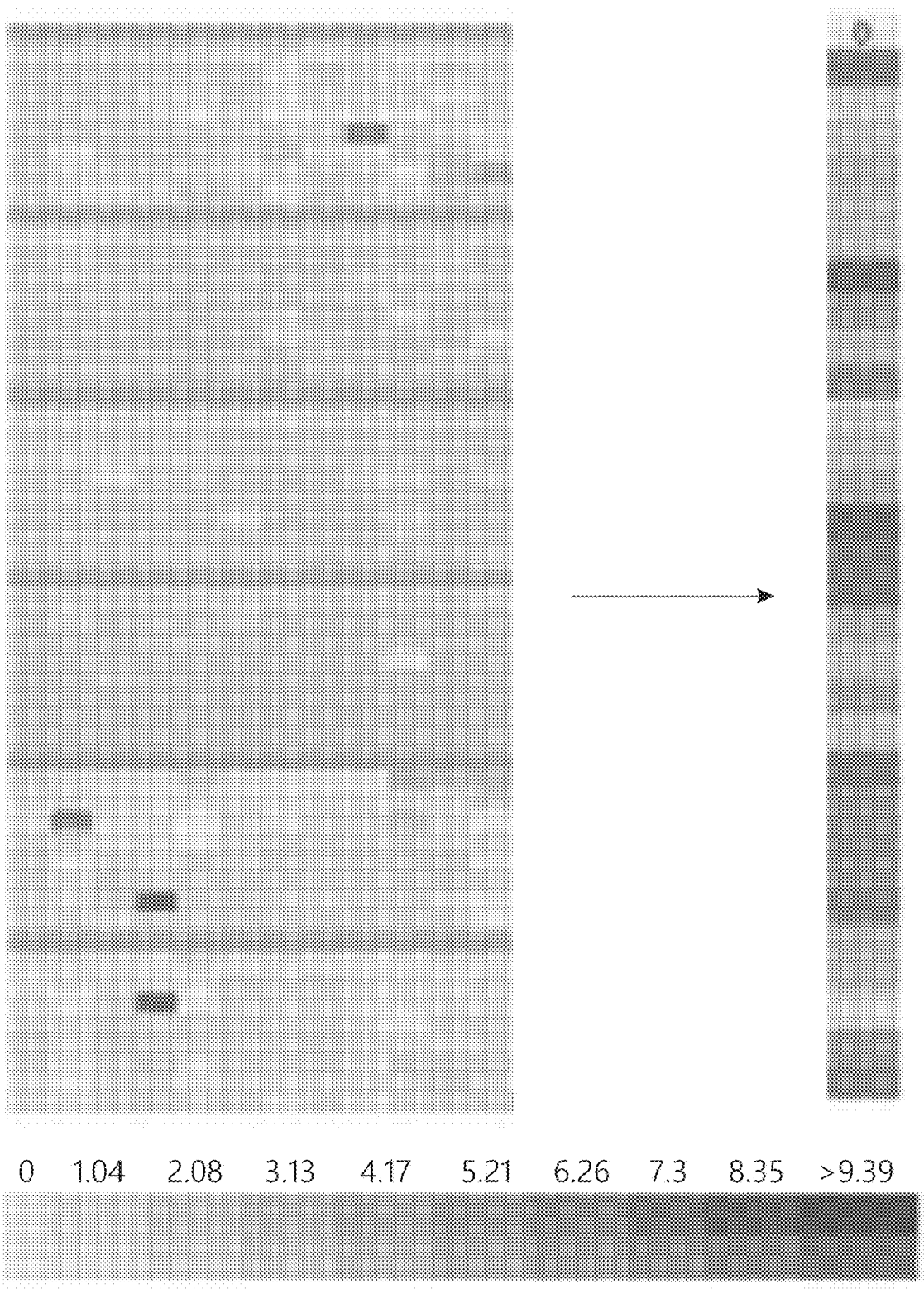

Because CHO-ERV-1+ cells have human sequence of the receptor, this lysate was selected for hybridoma screening. Monoclonal antibodies purified from hybridoma supernatants were screened by custom ELISA (FIGS. 2A-B, 11A-C). Human ERV1 lysate derived from CHO+ cells was immobilized on well plates at 1 mg/ml. Hybridoma supernatant derived from medium collected from 576 clones was hybridized with immobilized antigens. Heatmap of positive binders were identified and parental selection of clones of highest binders went through at least 2 cycles of sub-cloning resulting in enrichment of the of reactivity with ERV-1 (FIGS. 4, 12D). The results suggest that positive binders are able to interact with ERV-1 receptor molecules. Hybridoma supernatant of 27 clones were selected for further testing.

Resolvimab Interaction with ERV-1 Embedded in Cell Membranes

Multiplex for Immunoglobulin IgG isotype reveals IgG1 as the main subtype of positive binder clones clones. In order to understand if the ERV-1 protein receptor interaction with resovimab monoclonal antibodies would be affected by the cellular membrane, CHO-ERV-1+ cells were cultured until human ERV-1 receptor was positive. Cells were labeled with isotype control clone and secondary labeling for non-specific binding of antibodies. Hybridoma supernatant of the clones selected by ELISA were tested in CHO-ERV-1+ cells. The immune complex formation between the receptor and the hybridoma clones was detected by flow cytometry using FITC anti-murine IgG secondary antibodies. Results demonstrated that cell membrane did not interfere with the hybridoma clone interaction and similar positive reactivity was found among the clones and flow cytometry (FIGS. 5A-D, 12A-D) is compared to ELISA assay (FIG. 4).

Characterization of Anti-Human ERV-1 IgG Subtype and Sequencing

Figure 6:
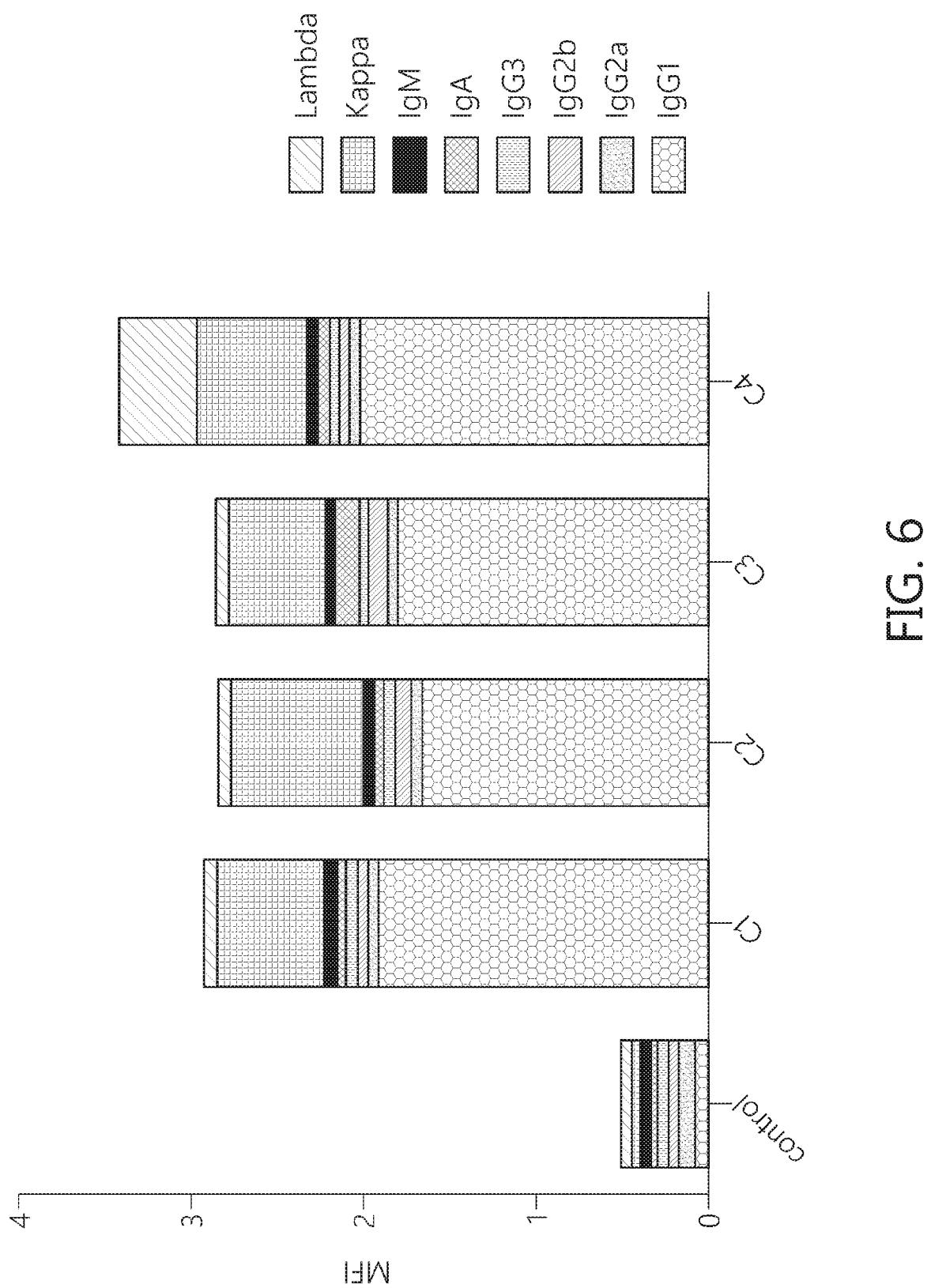
FIG. 6 depicts supernatant quantification and isotypes. Multiplex for Immunoglobulin IgG isotype reveals IgG1 as the main subtype of positive binder clones.
Figures 7, 8A:
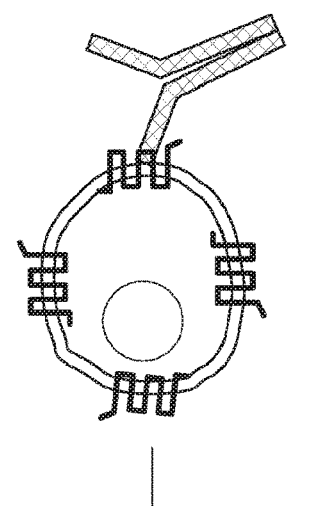
FIG. 7 depicts clones selected for in vivo assays. The figure shows clone Ids, parental hybridoma cells and isotyping. The engineered biomimmetic antibodies, resolvimabs, aim to activate ERV-1 receptor function and resolution of inflammation.
FIGS. 8A-B depict resolvimab calcium mobilization on ERV-1 positive CHO cells. Calcium mobilization is activated upon binding of an agonist ligand to ERV-1 CHO cells. On a concentration based assay (1-100 nM; specifically at 1 nM, 10 nM, and 100 nM), cells were treated with Resolvin, Chemerin, anti-ERV-1 Ab, isotype control and four resolvimab clones (C1-C4. After agonist treatment, detection of changes in fluorescence were detected by microplate reader and expressed as change in relative fluorescence units (ΔRFU) by fluorescent spectrophotometer. Values represent mean calcium stimulatory signals by CHO cells (n=4, mean±SD).
Figure 8B:
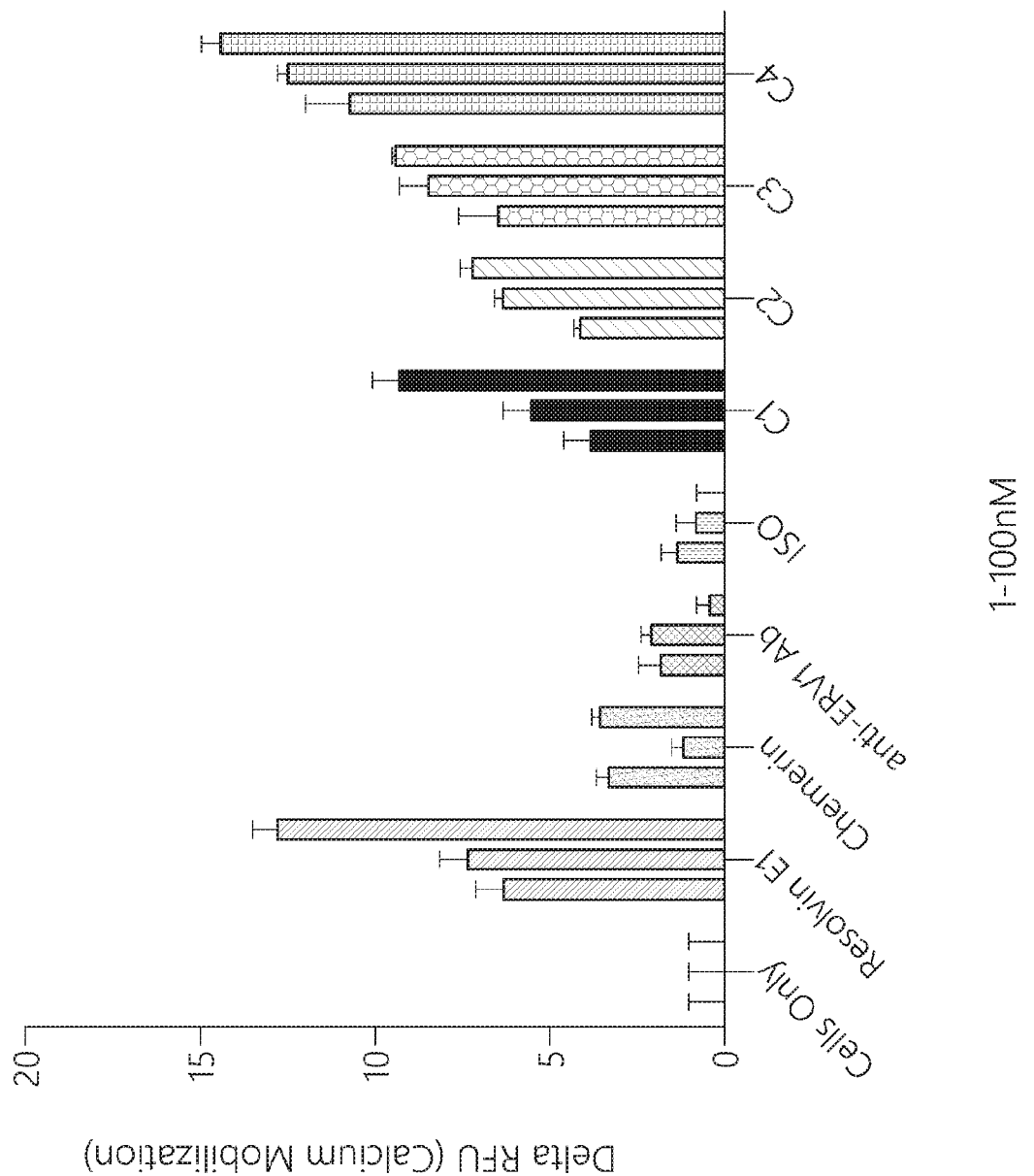
Figure 13B:
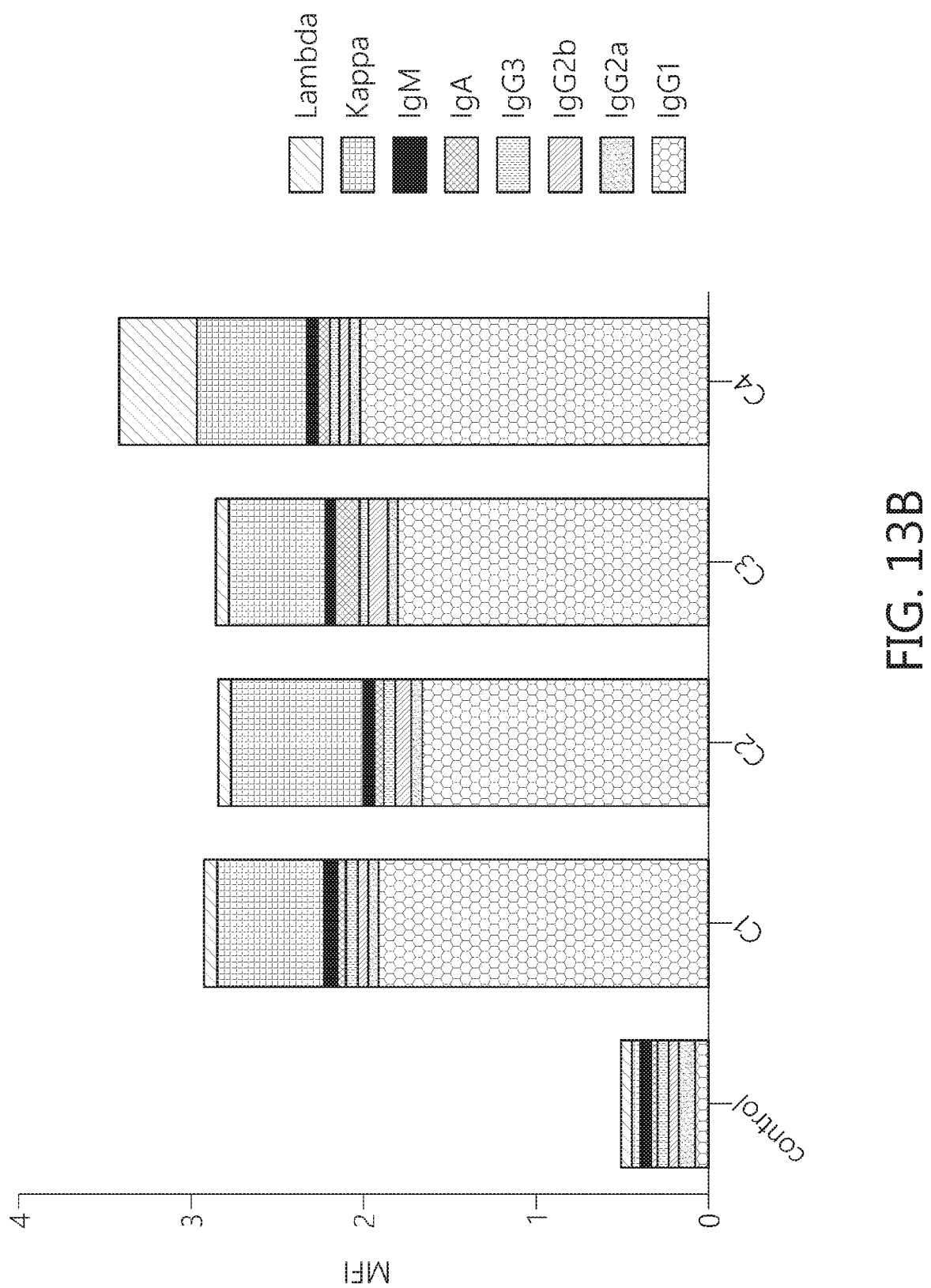

There are four IgG subclasses (1-4) present in human, mouse and rat. The subclasses differ in the number of disulfide bonds and the length and flexibility of the hinge region. Except for their variable regions, all immunoglobulins within one class share approximately 90% homology with one another, but only 60% among the other classes. To determine the IgG subclass, a multiplex assay was tested in vitro for the C1-C4 clone (FIGS. 6, 13A-B). Results indicated IgG1 as the main subtype of positive binder clones. DNA Sanger sequencing method allowed the nucleotide sequence of the monoclonal antibody FAB regions. Nucleotide sequences of VH and Vk regions from C1-C4 clones are shown (Table 1, FIG. 14A-B).

Resolvimab Activation of Intracellular Calcium Signaling

Figure 15:
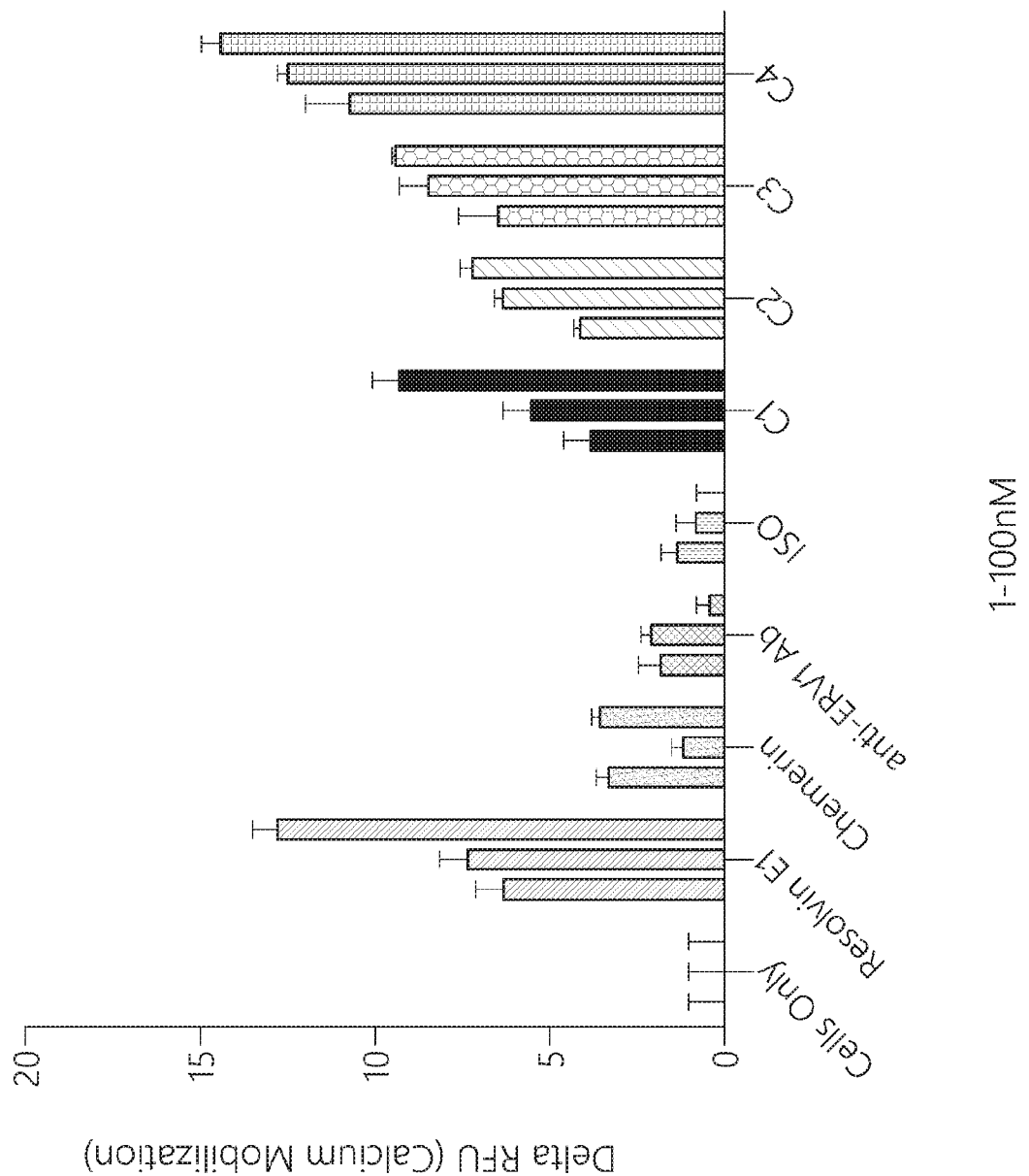
FIG. 15 shows intracellular signaling of anti-ERV-1 biomimetic antibodies In vitro. The figure depicts resolvimab calcium mobilization on ERV-1 positive CHO cells. Calcium mobilization is activated upon binding of an agonist ligand to ERV-1 CHO cells. In a concentration based assay (1-100 nM; specifically at 1 nM, 10 nM, and 100 nM), cells were treated with Resolvin, Chemerin, anti-ERV-1 Antibody, isotype control and four resolvimab clones (C1-C4). After agonist treatment, changes in fluorescence were detected by microplate reader and expressed as change in relative fluorescence units (ΔRFU) using a fluorescence spectrophotometer. Values represent mean calcium stimulatory signals by CHO cells (n=4, mean±SD).

To determine whether the immune complexes between ERV-1 receptor and various anti-ERV-1 antibodies permit the bound immune complex to interact with ERV-1 cellular receptor functions, an in vitro assay was devised. To that end, calcium intracellular signaling was measured upon agonist ligand binding. In a concentration dependent basis (1,10,100 nM), Resolvin E1, Chemerin, anti-ERV-1Ab, isotype control, hybridoma clones (C1-C4) were incubated with CHO-ERV-1 positive cells. After 20 seconds, calcium mobilization was measured through fluorescence (FIG. 15). The antibodies tested included a panel of mAb's, as well as a commercially available antibody. Plate reader results demonstrated significant increase in intracellular calcium mobilization when compared to isotype controls. Agonist functions were found in resolvinE-1, but not in chemerin and commercially anti-ERV-1 antibody. These data suggest that Resolvimabs (C1-C4) has potential biomimetic agonistic functions.

Resolvimab In Vivo Functions

Figure 9A:
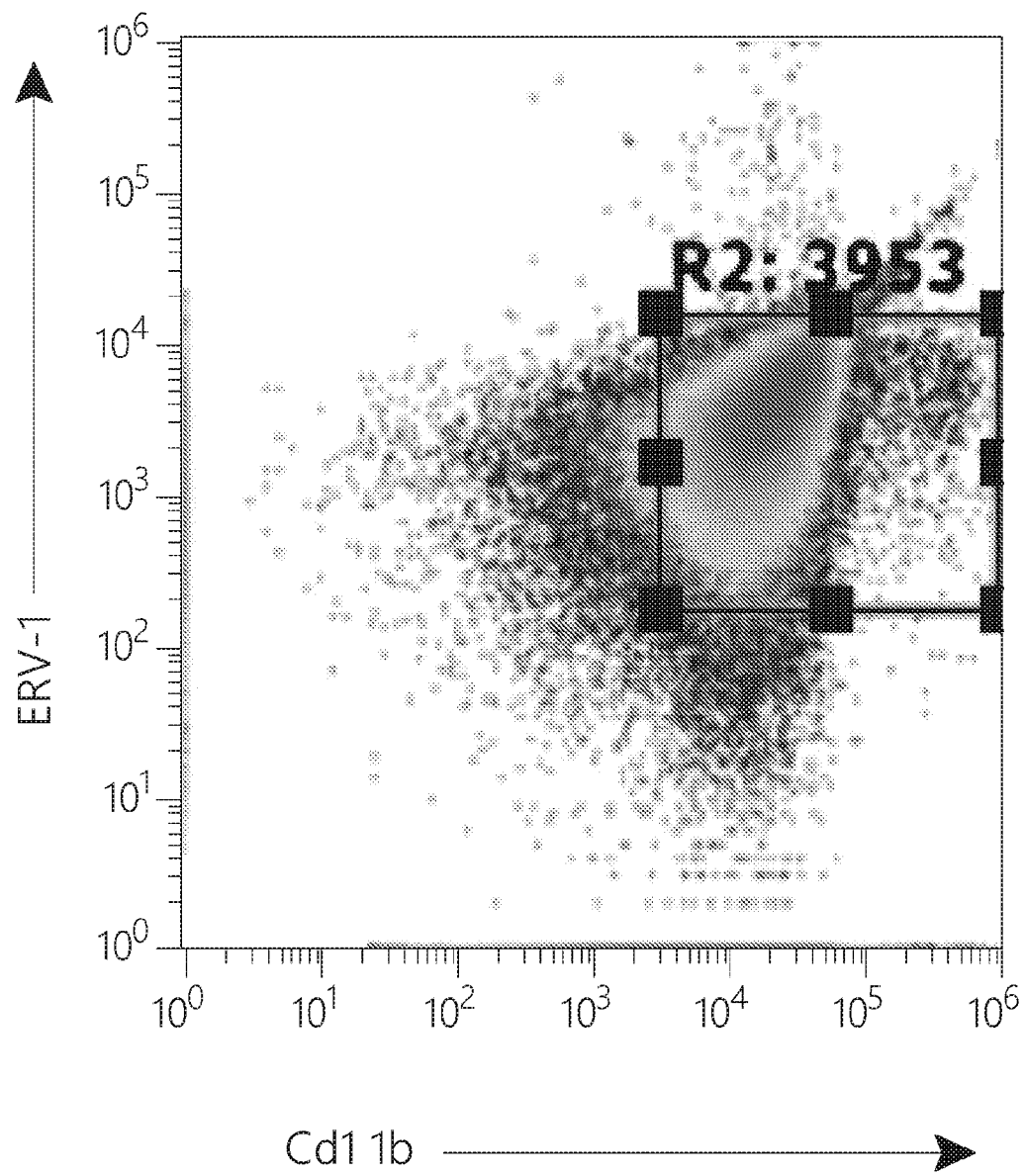
FIGS. 9A-D depict resolvimab in vivo actions on mice peritoneal lavage. After peritoneal lavage induction by zyomasan alone or in a combination with the reagents, total cells were collected at 12 hours on ERV-1 human receptor positive mice.
Figure 9B:
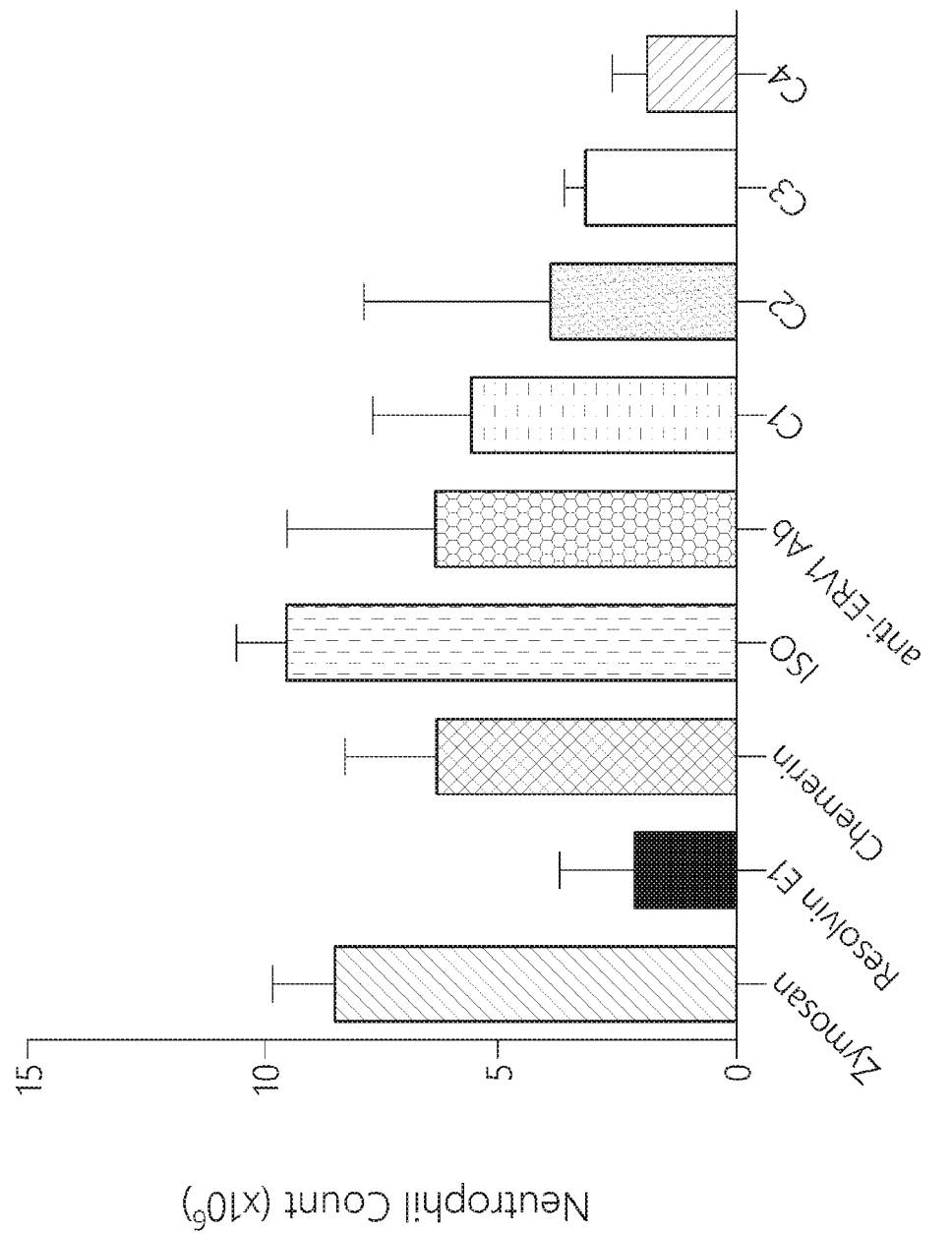
Figure 9C:
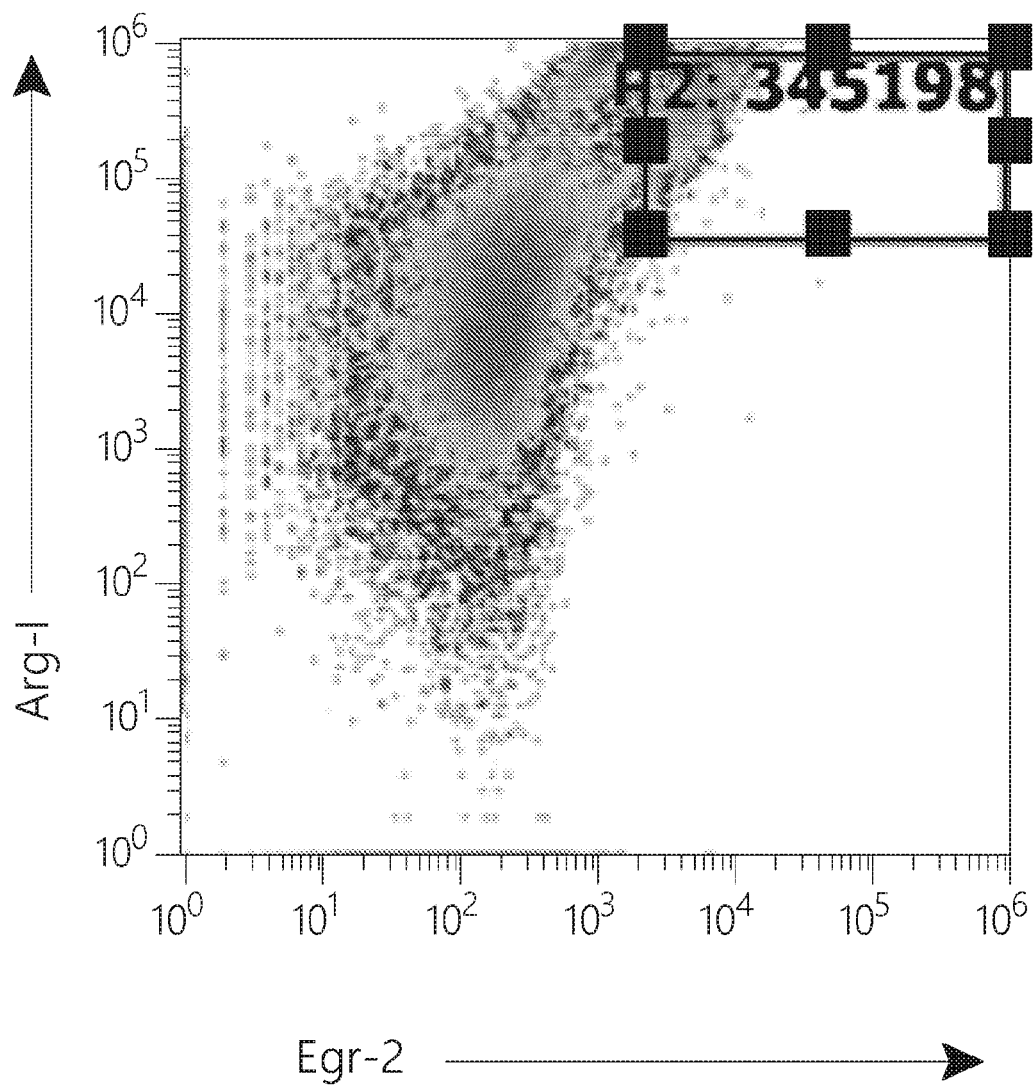
Figure 9D:
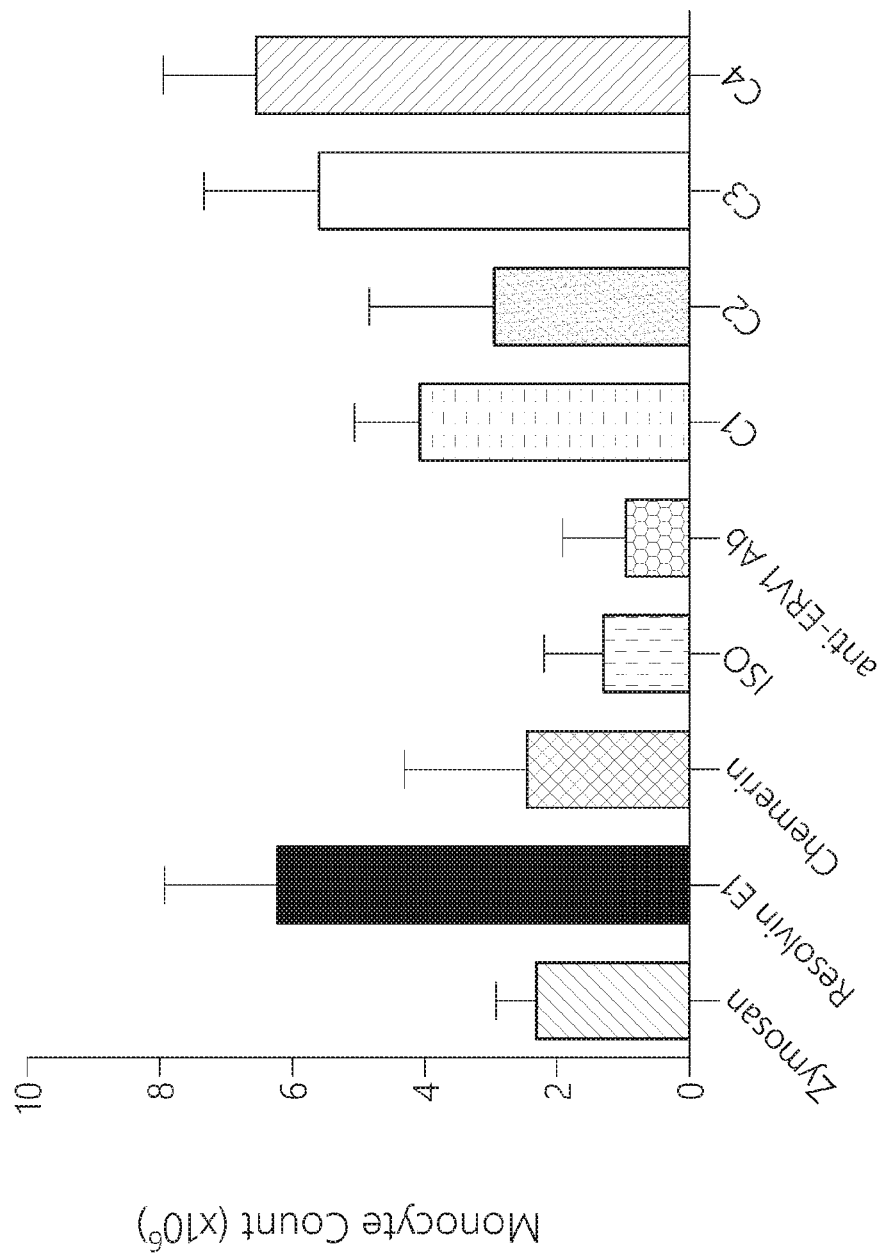
Figure 10A:
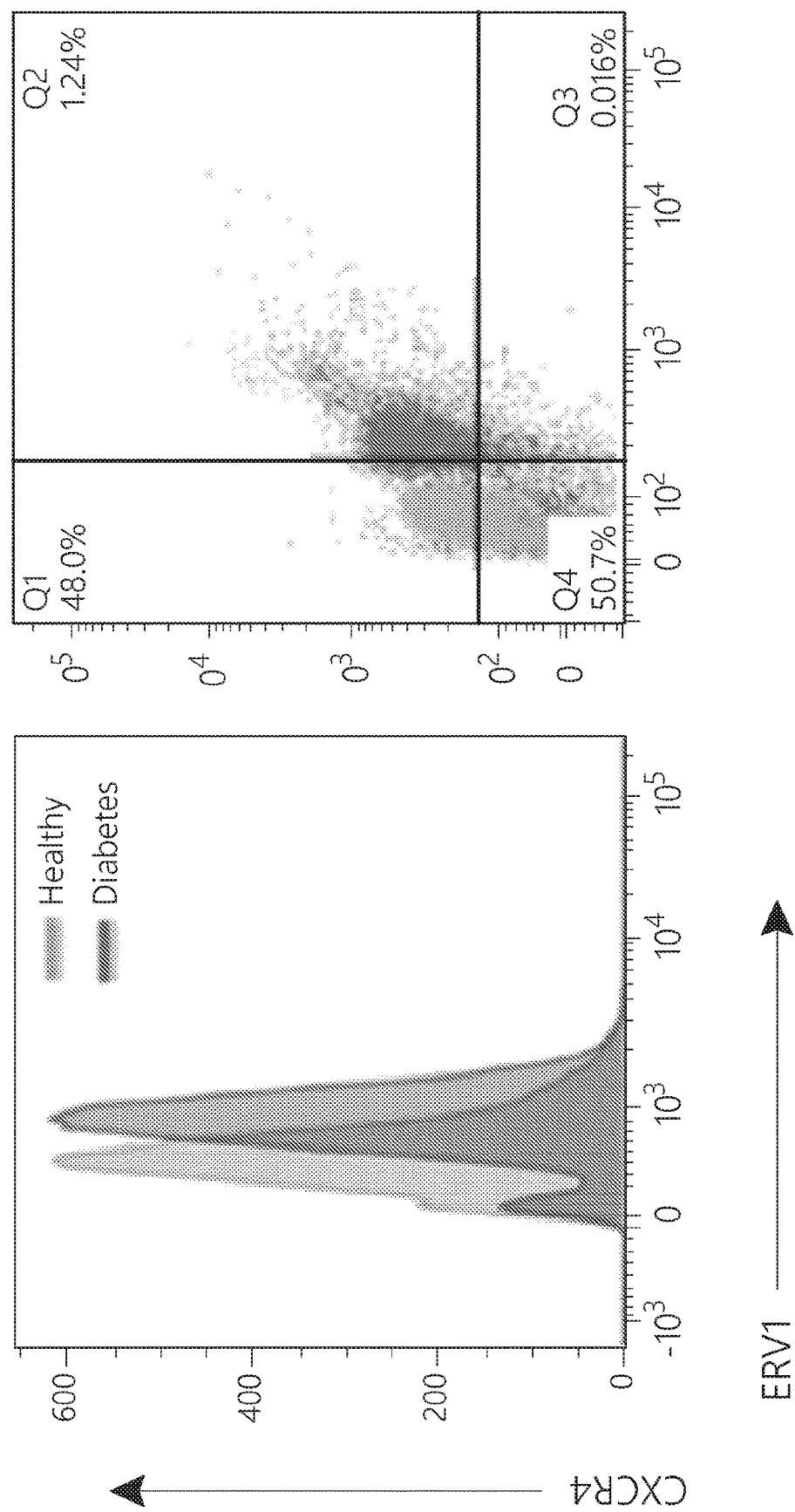
FIGS. 10A-D depict evidence of ERV1 receptor expression in health and chronic inflammation in diabetes.
Figure 10B:
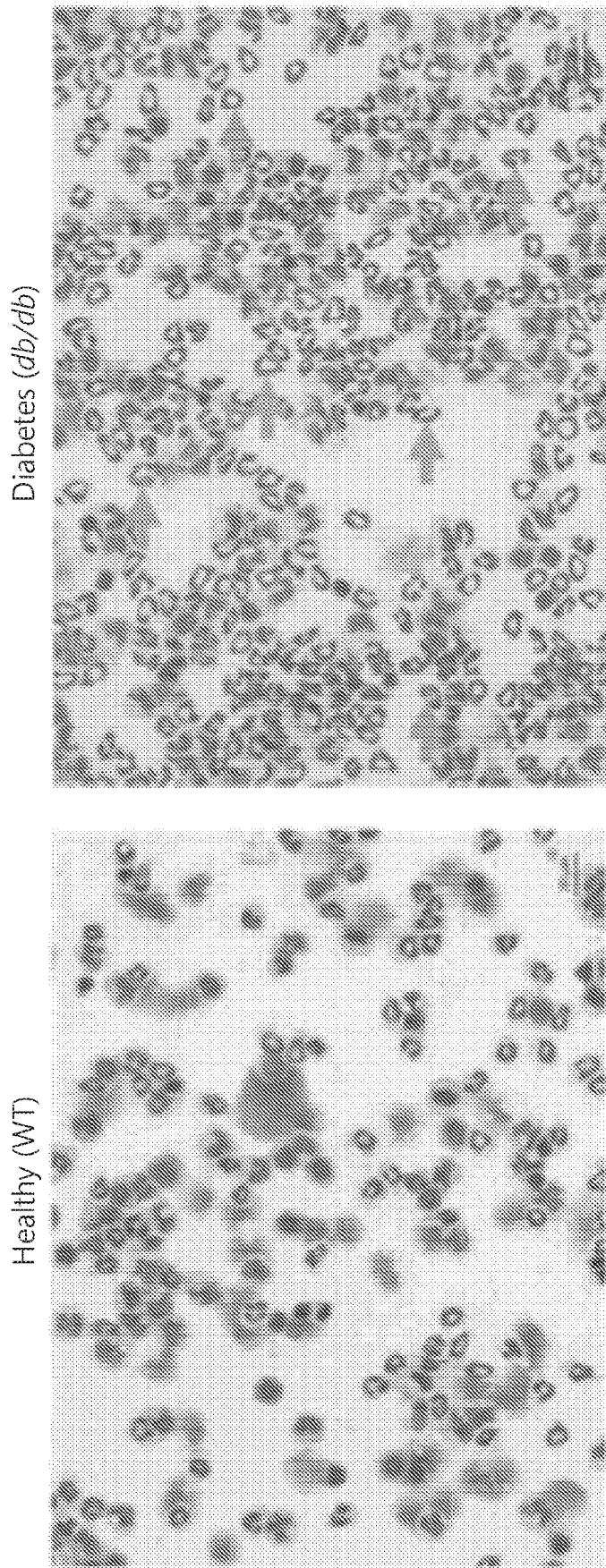
Figure 10C:
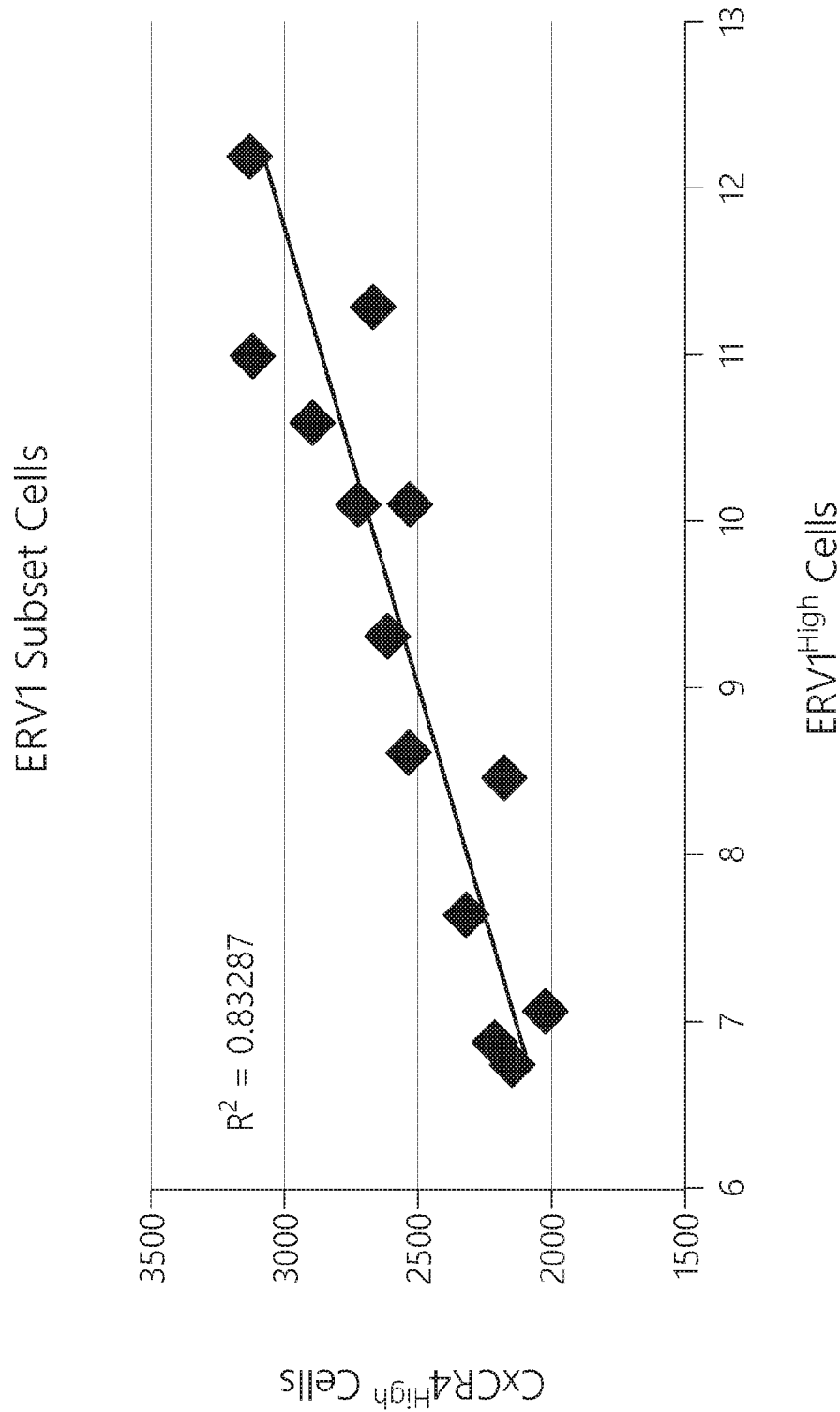
Figure 10D:
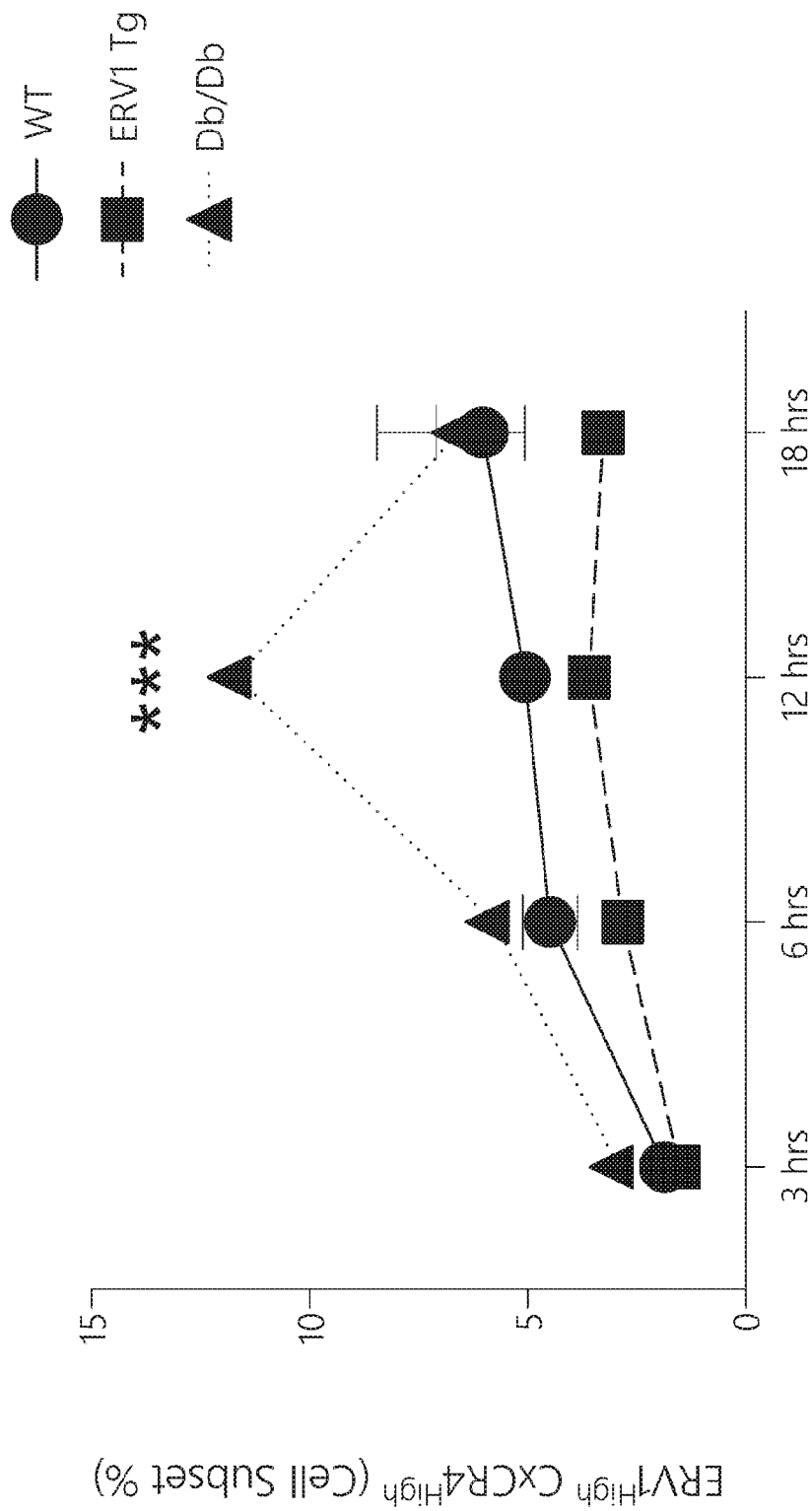
Figure 11A:
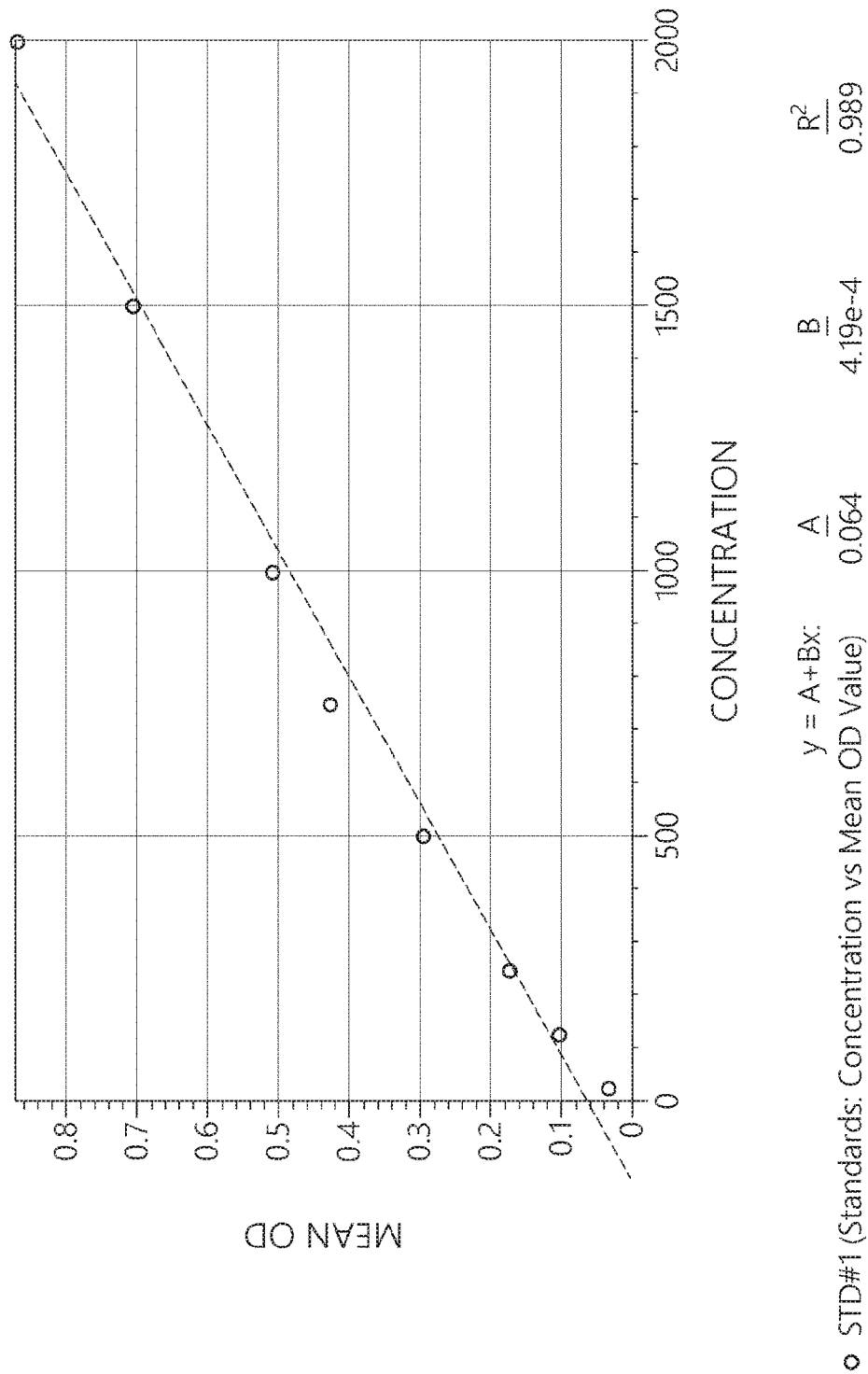
FIGS. 11A-C show development of a Custom Screening Assay for Human ERV1 receptor.
Figure 11B:
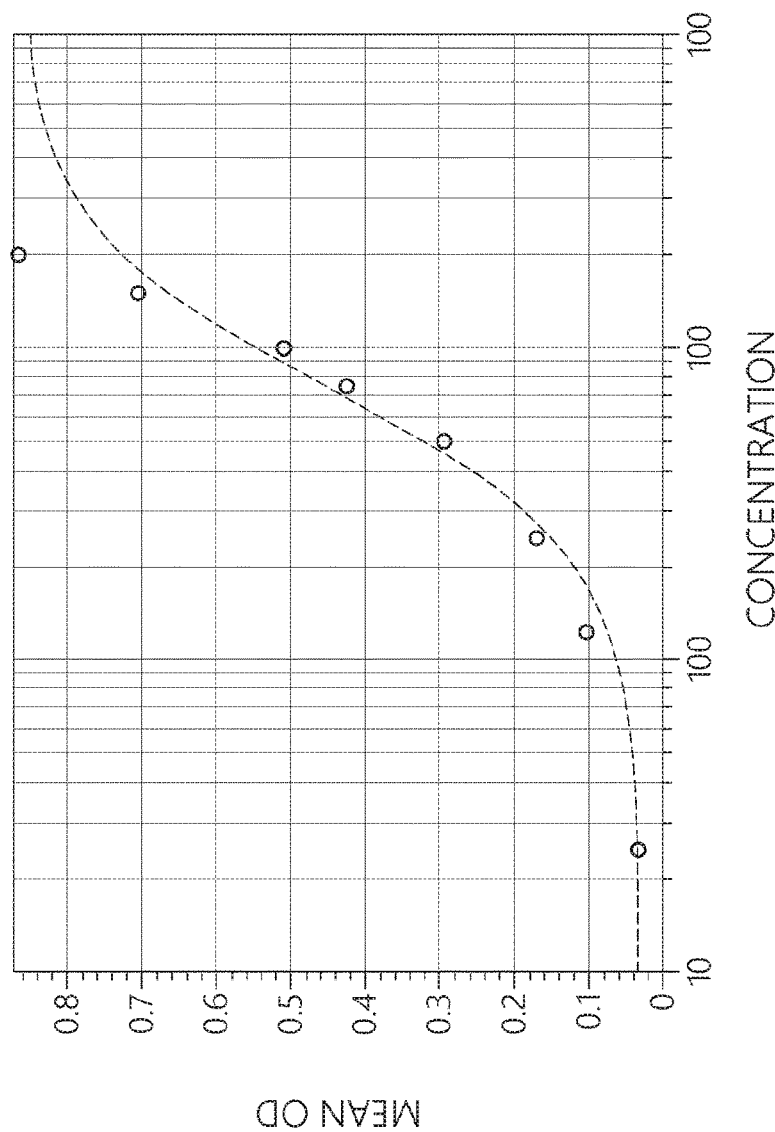
Figure 11C:
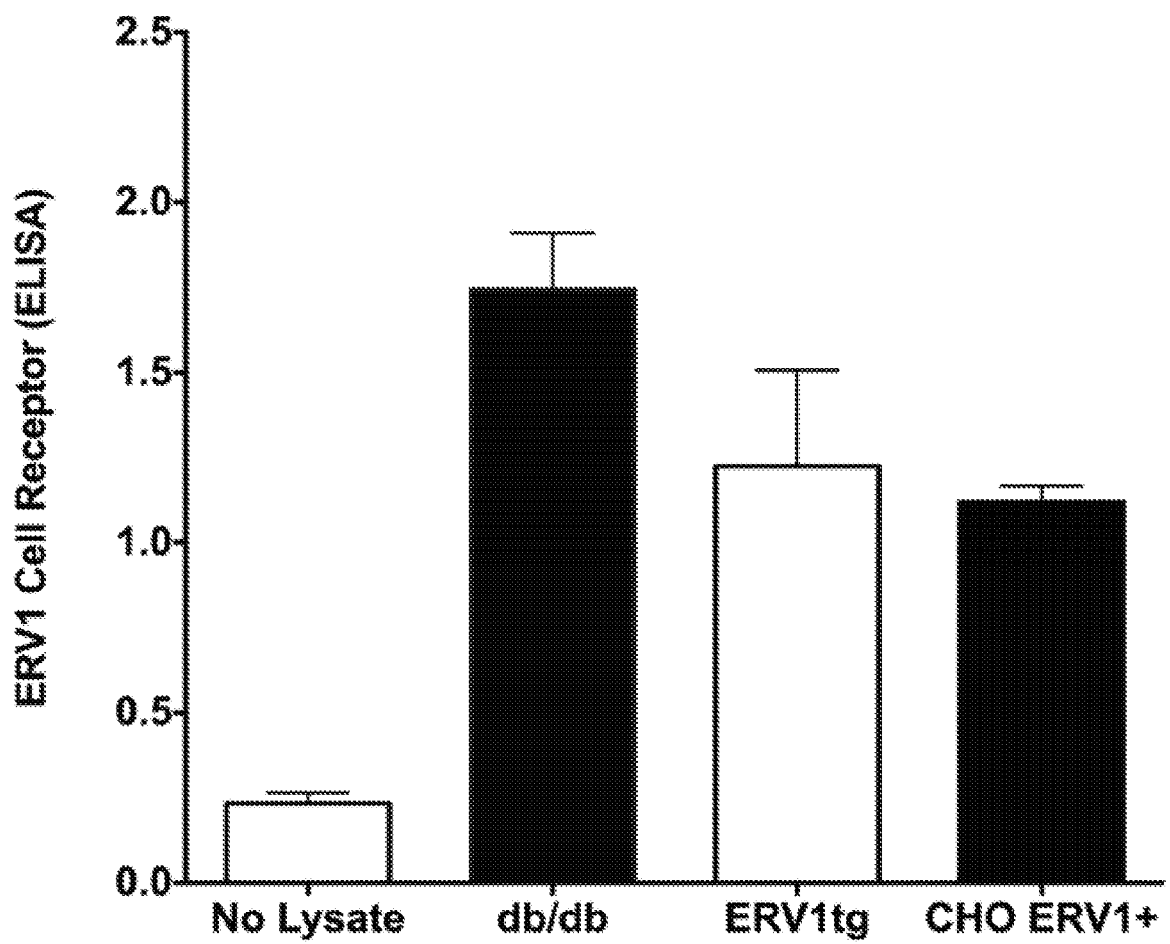
Figure 16A:
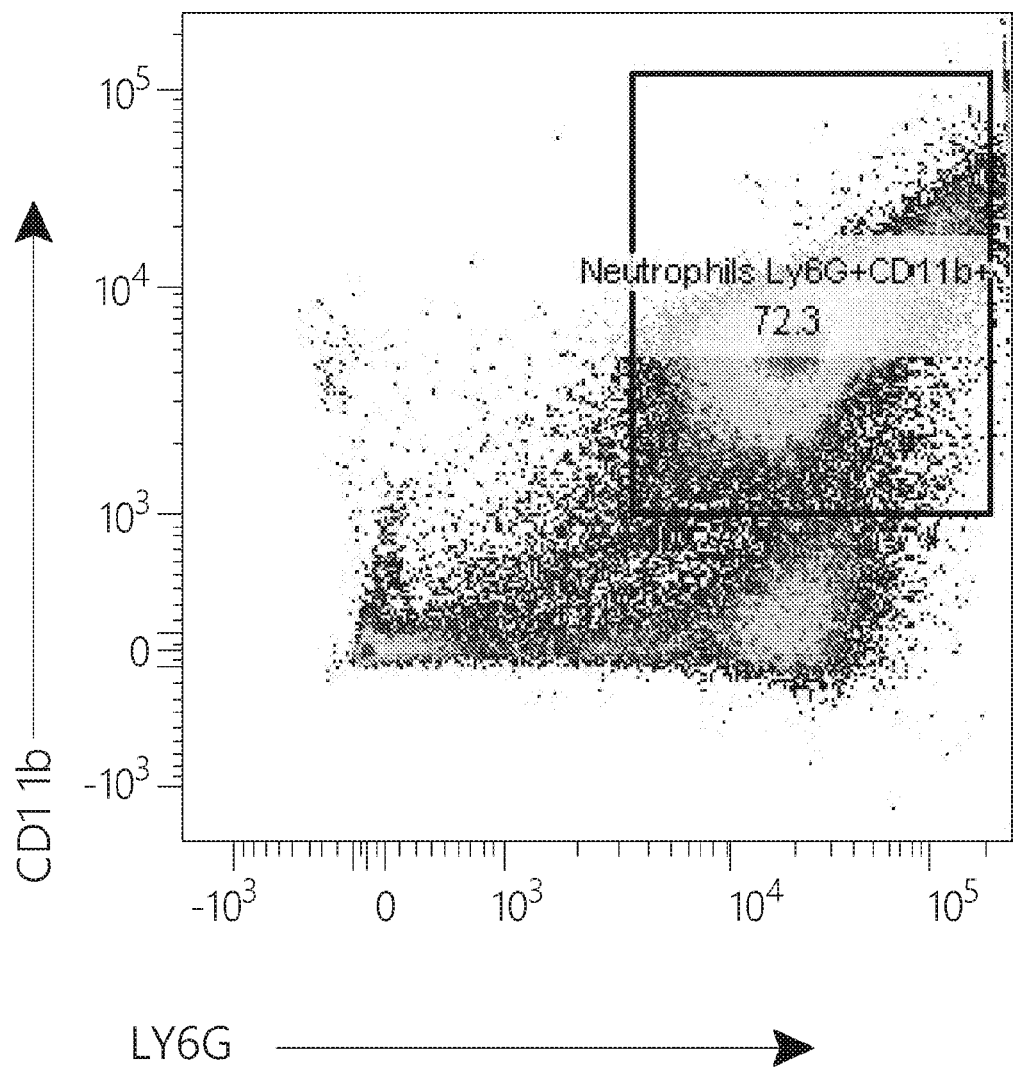
Figure 16B:
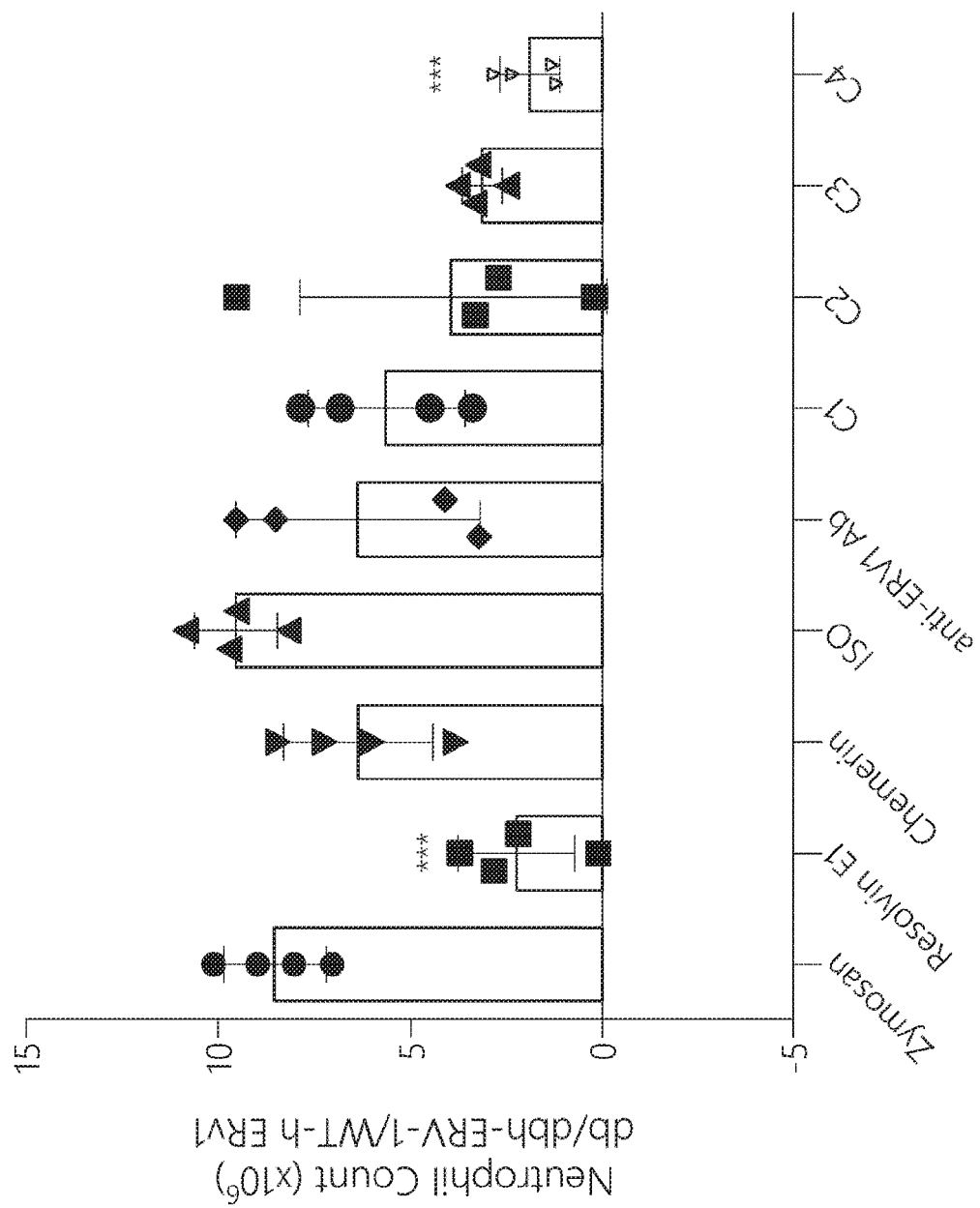

Peritonitis was initiated by zymosan particle injections (0.1 mg/ml) to ERV1tg mice peritoneal tissues. It had been previously established that Resolvin-E1 could affect inflammation-related responses in an ERV-1 dependent manner in vivo in cells derived from diabetic subjects (Freire, M. et al., J. Immunol. 198(2):718-728 (2017)). To further understand the biological response induced by resolvimabs, purified clones were injected together with the zymosan stimuli (FIGS. 9A-D). The agonistic actions of the monoclonal antibodies were compared to Resolvin E1, Chemerin, anti-ERV-1Ab, isotype control. We have looked if these compound would influence the phenotype of neutrophils and monocytes after 12 hours of inflammation in vivo. The results suggest a decrease of LY6G, CD11b neutrophils (FIG. 9A, 16B) and an increase of ERV-1, F40/80 positive monocytes that are for M2 pro-resolution phenotype, Arg-1/EGR+ cells (FIG. 9B, 16C). Data quantification through flow cytometry suggests that a decrease in inflammatory infiltrate occurs with resolvimabs, especially with C4 clones. A switch of inflammatory to pro-resolution monocytes is also found, demonstrating agonistic functions of resolvimab in vivo.

Additional Illustrative Embodiments

Alternative 1 provides a resolvin mimetic which comprises a recombinant antibody, or antibody fragment thereof, that binds the G protein coupled receptor Chemokine like receptor 1 (ERV1), said antibody, or antibody fragment thereof, comprises an amino acid sequence having at least 70% sequence identity to an amino acid sequence selected from the group consisting of SEQ ID: NOs: 2, 4, 6, 8, 10, 12, 14, and 16, or biologically active variant thereof, or combinations thereof.

Alternative 2 further provides the mimetic of alternative 1, which said antibody comprises the amino acid sequence having at least 71%, 72%, 73%, 74%, 75%, 76%, 97%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the amino acid sequence set forth in SEQ ID: NO: 2, 4, 6, 8, 10, 12, 14, and/or 16, or biologically active variant thereof, or combinations thereof.

Alternative 3 further provides the mimetic of any one of alternatives 1-2, wherein the antibody comprises a variable heavy chain (VH) sequence comprising an amino acid sequence having at least 71%, 72%, 73%, 74%, 75%, 76%, 97%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to an amino acid sequence selected from the group consisting of SEQ ID NO: 2, 6, 10, and/or 14, or biologically active variant thereof, or combination thereof.

Alternative 4 further provides the mimetic of any one of alternatives 1-2, wherein the antibody comprises a variable light chain (VK) sequence comprising an amino acid sequence having at least 71%, 72%, 73%, 74%, 75%, 76%, 97%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to an amino acid sequence selected from the group consisting of SEQ ID NO: 4, 8, 12, and/or 16, or biologically active variant thereof, or combination thereof.

Alternative 5 further provides the mimetic of any one of alternatives 1-4, wherein the antibody comprises a variable heavy chain (VH) sequence comprising an amino acid sequence having at least 71%, 72%, 73%, 74%, 75%, 76%, 97%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to an amino acid sequence set forth in SEQ ID NO: 2, and a variable light chain (VK) sequence comprising an amino acid sequence having at least 71%, 72%, 73%, 74%, 75%, 76%, 97%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to an amino acid sequence set forth in SEQ ID NO: 4.

Alternative 6 further provides the mimetic of alternative 5, wherein the antibody comprises a variable heavy chain (VH) sequence comprising an amino acid sequence set forth SEQ ID NO: 2, and a variable light chain (VK) sequence comprising an amino acid sequence set forth in SEQ ID NO: 4.

Alternative 7 further provides the mimetic of any one of alternatives 1-4, wherein the antibody comprises a variable heavy chain (VH) sequence comprising an amino acid sequence having at least 71%, 72%, 73%, 74%, 75%, 76%, 97%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to an amino acid sequence set forth in SEQ ID NO: 6, and a variable light chain (VK) sequence comprising an amino acid sequence having at least 71%, 72%, 73%, 74%, 75%, 76%, 97%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to an amino acid sequence set forth in SEQ ID NO: 8.

Alternative 8 further provides the mimetic of alternative 7, wherein the antibody comprises a variable heavy chain (VH) sequence comprising an amino acid sequence set forth in SEQ ID NO: 6, and a variable light chain (VK) sequence comprising an amino acid sequence set forth in SEQ ID NO: 8.

Alternative 9 further provides the mimetic of any one of alternatives 1-4, wherein the antibody comprises a variable heavy chain (VH) sequence comprising an amino acid sequence having at least 71%, 72%, 73%, 74%, 75%, 76%, 97%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to an amino acid sequence set forth in SEQ ID NO: 10, and a variable light chain (VK) sequence comprising an amino acid sequence having at least 70% sequence identity to an amino acid sequence set forth in SEQ ID NO: 12.

Alternative 10 further provides the mimetic of alternative 9, wherein the antibody comprises a variable heavy chain (VH) sequence comprising an amino acid sequence set forth in SEQ ID NO: 10, and a variable light chain (VK) sequence comprising an amino acid sequence set forth in SEQ ID NO: 12.

Alternative 11 further provides the mimetic of any one of alternatives 1-4, wherein the antibody comprises a variable heavy chain (VH) sequence comprising an amino acid sequence having at least 71%, 72%, 73%, 74%, 75%, 76%, 97%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to an amino acid sequence set forth in SEQ ID NO: 14, and a variable light chain (VK) sequence comprising an amino acid sequence having at least 70% sequence identity to an amino acid sequence set forth in SEQ ID NO: 16.

Alternative 12 further provides the mimetic of alternative 11, wherein the antibody comprises a variable heavy chain (VH) sequence comprising an amino acid sequence set forth in SEQ ID NO: 14, and a variable light chain (VK) sequence comprising an amino acid sequence set forth in SEQ ID NO: 16.

Alternative 13 further provides the mimetic of any one of alternatives 1-12, wherein the VH and VH are operably linked.

Alternative 14 further provides a fusion polypeptide comprising the mimetic of any one of alternatives 1-13.

Alternative 15 further provides a pharmaceutical composition comprising the mimetic of any one of alternatives 1-13 in combination with at least one pharmaceutically acceptable carrier or excipient.

Alternative 16 further provides a vaccine composition comprising the mimetic of any one of alternatives 1-13.

Alternative 17 further provides a method of treating or preventing an inflammatory disorder in a subject in need thereof, the method comprising the steps of administering a therapeutically effective amount of at least one mimetic of any one of alternatives 1-16.

Alternative 18 further provides the method of alternative 17, wherein the subject is human.

Alternative 19 further provides the method of any one of alternatives 17-18, wherein the subject is afflicted with a disorder selected from the group consisting of allergic reactions, anaphylactic reactions, arthritis, asthma, atherosclerosis, bone diseases, breast cancer, cancer, cardiovascular diseases, colon cancer, degenerative neurologic disorders, dementia, diabetes mellitus, eye diseases, gastrointestinal disorders, genitourinary disorders, hematologic disorders, hepatobiliary disorders, hypertension, infectious diseases, leukemia/lymphoma, lung cancer, metabolic disorders, neurological disorders, neuromuscular disorders, obesity/eating disorders, parasitic diseases, perinatal disorders, pregnancy, prostate cancer, psychiatric disorders, pulmonary disorders, renal disorders, rheumatic diseases, stroke, wound healing, oral infections, periodontal disease, brain injury, trauma, neuronal inflammation, and/or women's health.

Alternative 20 further provides the method of any one of alternatives 17-19, wherein the mimetic is administered topically.

he method of any one of claims 17-19, wherein the mimetic is administered enterally.

Alternative 21 further provides the method of any one of alternatives 17-19, wherein the mimetic is administered orally.

Alternative 22 further provides the method of any one of alternatives 17-19, wherein the antibody is administered to the subject's oral cavity.

Alternative 23 further provides the method of any one of alternatives 17-23, further comprising administering a therapeutically effective amount of a therapeutic agent.

Alternative 24 further provides the method of alternative 24, wherein the therapeutic agent selected from the group consisting of resolvin, anticancer, chemotherapeutic, analgesics, anesthetics, antimicrobial agents, antibacterial agents, antiviral agents, antifungal agents, antibiotics, antiinflammatory agents, antioxidants, antiseptic agents, immunomodulatory agents, and combinations thereof.

Alternative 25 further provides the method of any one of alternatives 24-25, wherein the therapeutic agent is administered conjointly, in combination, or subsequently to administering the mimetic of any one of alternatives 1-13.

INCORPORATION BY REFERENCE

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

EQUIVALENTS

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A resolvin mimetic comprising a recombinant antibody, or antigen-binding fragment thereof, which binds a G protein coupled receptor/Chemokine like receptor 1 (CMKLR1 or ERV1), wherein said antibody, or antigen-binding fragment thereof, comprises a variable heavy chain (VH) sequence comprising an amino acid sequence having at least 95% sequence identity to an amino acid sequence selected from the group consisting of SEQ ID NO: 2, 6, 10, and 14 and a variable light chain (VK) sequence comprising an amino acid sequence having at least 95% sequence identity to the amino acid sequence of SEQ ID NO: 16.

2. The resolvin mimetic of claim 1, wherein said antibody or antigen-binding fragment thereof comprises a variable heavy chain (VH) sequence comprising the amino acid sequence set forth in SEQ ID NO: 14, and a variable light chain (VK) sequence comprising the amino acid sequence set forth in SEQ ID NO: 16.

3. The resolvin mimetic of claim 1, wherein the VH and VK sequences are operably linked.

4. A fusion polypeptide comprising the resolvin mimetic of claim 1.

5. A pharmaceutical composition comprising the resolvin mimetic of claim 1 in combination with at least one pharmaceutically acceptable carrier or excipient.

6. A method of treating an inflammatory disorder in a subject in need thereof, said method comprising administering a therapeutically effective amount of at least one resolvin mimetic of claim 1.

7. The method of claim 6, wherein said subject is afflicted with a disorder selected from the group consisting of allergic reactions, anaphylactic reactions, arthritis, asthma, atherosclerosis, bone diseases, breast cancer, cancer, cardiovascular diseases, colon cancer, degenerative neurologic disorders, dementia, diabetes mellitus, eye diseases, gastrointestinal disorders, genitourinary disorders, hematologic disorders, hepatobiliary disorders, hypertension, infectious diseases, leukemia, lymphoma, lung cancer, oral cancer, metabolic disorders, neurological disorders, neuromuscular disorders, obesity, eating disorders, parasitic diseases, perinatal disorders, pregnancy, prostate cancer, psychiatric disorders, pulmonary disorders, renal disorders, rheumatic diseases, stroke, wound healing, oral infections, periodontal disease, brain injury, trauma, and neuronal inflammation.

8. The method of claim 6, wherein said resolvin mimetic is administered enterically, topically, orally, or parenterally.

9. The method of claim 6, further comprising administering a therapeutically effective amount of one or more additional therapeutic agents.

10. The method of claim 9, wherein said one or more therapeutic agents is selected from the group consisting of a resolvin, an anti-inflammatory agent, an anticancer agent, a chemotherapeutic, an analgesic, an anesthetic, an antimicrobial agent, an antibacterial agent, an antiviral agent, an antifungal agent, an antibiotic, an anti-inflammatory agent, an antioxidant, an antiseptic agent, and an immunomodulatory agent, or any combination thereof.

* * * * *

UNITED STATES PATENT AND TRADEMARK OFFICE
CERTIFICATE OF CORRECTION

PATENT NO. : 11,351,140 B2
APPLICATION NO. : 16/611203
DATED : June 7, 2022
INVENTOR(S) : Marcelo Freire It is certified that error appears in the above-identified patent and that said Letters Patent is hereby corrected as shown below:

In the Specification

In Column 8, Line 32, delete "biomimmetic" and insert --biomimetic--.

In Column 8, Line 41, delete "(C1-C4." and insert --(C1-C4).--.

In Column 8, Lines 48-49, delete "zyomasan" and insert --zymosan--.

In Column 10, Line 12, delete "zyomasan" and insert --zymosan--.

In Column 13, Line 62, delete "Viol." and insert --Mol.--.

In Column 14, Line 44, delete "pencicyclovir" and insert --penciclovir--.

In Column 14, Line 44, delete "gancicyclovir," and insert --ganciclovir,--.

In Column 14, Line 46, delete "famcicyclovir," and insert --famciclovir,--.

In Column 14, Line 49, delete "trimethoprin," and insert --trimethoprim,--.

In Column 14, Lines 60-61, delete "amorolfin," and insert --amorolfine,--.

In Column 15, Line 57, delete "phtalanilide" and insert --phthalanilide--.

In Column 15, Lines 61-62, delete "5-fluorouracile" and insert --5-fluorouracil--.

In Column 16, Line 1, delete "adramycin," and insert --adriamycin,--.

In Column 16, Line 7, delete "vinblastin," and insert --vinblastine,--.

Signed and Sealed this
Fourteenth Day of March, 2023

Katherine Kelly Vidal
*Director of the United States Patent and Trademark Office*

In Column 16, Line 7, delete "vincristin," and insert --vincristine,--.

In Column 16, Line 20, delete "aminogluthetimide," and insert --aminoglutethimide,--.

In Column 16, Line 21, delete "formestan" and insert --formestane--.

In Column 16, Lines 28-29, delete "budenoside," and insert --budesonide,--.

In Column 16, Line 33, delete "revimid" and insert --revlimid--.

In Column 16, Line 33, delete "leukotrien" and insert --leukotriene--.

In Column 16, Line 41, delete "biphosphonate" and insert --bisphosphonate--.

In Column 16, Line 42, delete "mannuronic" and insert --minodronic--.

In Column 16, Line 51, delete "merocyanin" and insert --merocyanine--.

In Column 16, Line 54, delete "mesalazin," and insert --mesalazine,--.

In Column 16, Line 63, delete "lomoxicam," and insert --lornoxicam,--.

In Column 17, Line 10, delete "combrestatin" and insert --combretastatin--.

In Column 17, Line 31, delete "5-fluorouracile" and insert --5-fluorouracil--.

In Column 17, Line 34, delete "vinblastin," and insert --vinblastine,--.

In Column 17, Line 35, delete "vincristin," and insert --vincristine,--.

In Column 21, (Table 1-continued), Line 28, delete "SWMEIWVKQR" and insert --SYWMHWVKQR--.

In Column 21, Table 1-continued, Line 30, delete "FVWGQGTLV" and insert --FVYWGQGTLV--.

In Column 26, Line 4, delete "metalothionein." and insert --metallothionein.--.

In Column 27, Line 6, delete "hydroxyide," and insert --hydroxide,--.

In Column 28, Line 15, delete "intarterial," and insert --intraarterial,--.

In Column 29, Lines 1-2, delete "proteinacious" and insert --proteinaceous--.

In Column 34, Line 31, delete "Antti" and insert --Anti--.

In Column 34, Line 47, delete "2-mercaptothanol," and insert --2-mercaptoethanol,--.

CERTIFICATE OF CORRECTION (continued)
U.S. Pat. No. 11,351,140 B2

In Column 35, Line 12, delete "(ARFU)." and insert --(ΔRFU).--.

In Column 35, Line 13, delete "(1, nM," and insert --(1 nM,--.

In Column 36, Line 5, delete "hibridoma" and insert --hybridoma--.

In Column 36, Line 26, delete "of the of" and insert --of the--.

In Column 36, Line 33, delete "clones clones." and insert --clones.--.

In Column 36, Line 35, delete "resovimab" and insert --resolvimab--.

In Column 36, Line 62, delete "FIG." and insert --FIGS.--.

In Column 37, Line 30, delete "(FIG." and insert --(FIGS.--.

In Column 37, Line 32, delete "(FIG." and insert --(FIGS.--.

SEQUENCE LISTING

<160> NUMBER OF SEQ ID NOS: 16

<210> SEQ ID NO 1
<211> LENGTH: 345
<212> TYPE: DNA
<213> ORGANISM: Artificial Sequence
<220> FEATURE:
<223> OTHER INFORMATION: Immunoglobulin VH Region

<400> SEQUENCE: 1

```
gagcttgtga tgcctggggc ttcagtgaag ctgtcctgca aggcttctgg ctacaccttc      60
accagctact ggatgcactg ggtgaagcag aggcctggac aaggccttga gtgggtcgca     120
```

```
gagattgatc cttctgatag ttatactaac tacaatcaaa agttcaaggg caaggccaca    180
ttgactgtag acaaatcctc cagcacagcc tacatgcagc tcagcagcct acatctgag    240 gactctgcgg tctattactg tgcaagagat ggggatatat taactacggt agtagctaag    300
gggtttgttt actggggcca agggactctg gtcactgtct ctgca                   345
```

<210> SEQ ID NO 2
<211> LENGTH: 115
<212> TYPE: PRT
<213> ORGANISM: Artificial Sequence
<220> FEATURE:
<223> OTHER INFORMATION: Immunoglobulin VH Region

<400> SEQUENCE: 2

```
Glu Leu Val Met Pro Gly Ala Ser Val Lys Leu Ser Cys Lys Ala Ser
1               5                   10                  15

Gly Tyr Thr Phe Thr Ser Tyr Trp Met His Val Lys Gln Arg Pro
            20                  25                  30

Gly Gln Gly Leu Glu Trp Val Ala Glu Ile Asp Pro Ser Asp Ser Tyr
        35                  40                  45

Thr Asn Tyr Asn Gln Lys Phe Lys Gly Lys Ala Thr Leu Thr Val Asp
    50                  55                  60

Lys Ser Ser Thr Ala Tyr Met Gln Leu Ser Ser Leu Thr Ser Glu
65                  70                  75                  80

Asp Ser Ala Val Tyr Tyr Cys Ala Arg Asp Gly Asp Ile Leu Thr Thr
                85                  90                  95

Val Val Ala Lys Gly Phe Val Tyr Trp Gly Gln Gly Thr Leu Val Thr
            100                 105                 110

Val Ser Ala
        115
```

<210> SEQ ID NO 3
<211> LENGTH: 312
<212> TYPE: DNA
<213> ORGANISM: Artificial Sequence
<220> FEATURE:
<223> OTHER INFORMATION: Immunoglobulin VL(K) region

<400> SEQUENCE: 3

```
ctctccctgc ctgtcagtct tggagatcaa gcctccatct cttgcagatc tagtcagacc    60
attgtacata gtaatggaaa cacctattta gaatggtacc tgcagaaacc aggccagtct   120
ccaaagctcc tgatctacaa agtttccaac cgatttctg gggtcccaga caggttcagt    180
ggcagtggat cagggacaga tttcacactc aagatcagca gagtggaggc tgaggatctg    240
ggagtttatt actgctttca aggttcacat gttccgtgga cgttcggtgg aggcaccaag    300
ctggaaatca aa                                                       312
```

<210> SEQ ID NO 4
<211> LENGTH: 104
<212> TYPE: PRT
<213> ORGANISM: Artificial Sequence
<220> FEATURE:
<223> OTHER INFORMATION: Immunoglobulin VL(K) region

<400> SEQUENCE: 4

```
Leu Ser Leu Pro Val Ser Leu Gly Asp Gln Ala Ser Ile Ser Cys Arg
1               5                   10                  15

Ser Ser Gln Thr Ile Val His Ser Asn Gly Asn Thr Tyr Leu Glu Trp
```

```
                 20                  25                  30

Tyr Leu Gln Lys Pro Gly Gln Ser Pro Lys Leu Leu Ile Tyr Lys Val
                 35                  40                  45

Ser Asn Arg Phe Ser Gly Val Pro Asp Arg Phe Ser Gly Ser Gly Ser
             50                  55                  60

Gly Thr Asp Phe Thr Leu Lys Ile Ser Arg Val Glu Ala Glu Asp Leu
 65                  70                  75                  80

Gly Val Tyr Tyr Cys Phe Gln Gly Ser His Val Pro Trp Thr Phe Gly
                 85                  90                  95

Gly Gly Thr Lys Leu Glu Ile Lys
            100

<210> SEQ ID NO 5
<211> LENGTH: 372
<212> TYPE: DNA
<213> ORGANISM: Artificial Sequence
<220> FEATURE:
<223> OTHER INFORMATION: Immunoglobulin VH Region

<400> SEQUENCE: 5
gaggttcagc tgcagcagtc tggggctgag cttgtgatgc ctggggcttc agtgaagctg      60
tcctgcaagg cttctggcta caccttcacc agctactgga tgcactgggt gaagcagagg     120
cctggacaag ccttgagtg gtcgcagag attgatcctt ctgatagtta tactaactac      180
aatcaaaagt tcaagggcaa ggccacattg actgtagaca atcctccag cacagcctac      240 atgcagctca gcagcctgac atctgaggac tctgcggtct attactgtgc aagagatggg     300
gatatattaa ctacggtagt agctaagggg tttgtttact ggggccaagg gactctggtc     360
actgtctctg ca                                                         372

<210> SEQ ID NO 6
<211> LENGTH: 124
<212> TYPE: PRT
<213> ORGANISM: Artificial Sequence
<220> FEATURE:
<223> OTHER INFORMATION: Immunoglobulin VH Region

<400> SEQUENCE: 6

Glu Val Gln Leu Gln Gln Ser Gly Ala Glu Leu Val Met Pro Gly Ala
 1               5                  10                  15

Ser Val Lys Leu Ser Cys Lys Ala Ser Gly Tyr Thr Phe Thr Ser Tyr
                 20                  25                  30

Trp Met His Trp Val Lys Gln Arg Pro Gly Gln Gly Leu Glu Trp Val
             35                  40                  45

Ala Glu Ile Asp Pro Ser Asp Ser Tyr Thr Asn Tyr Asn Gln Lys Phe
         50                  55                  60

Lys Gly Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Gly Asp Ile Leu Thr Thr Val Val Ala Lys Gly Phe Val
            100                 105                 110

Tyr Trp Gly Gln Gly Thr Leu Val Thr Val Ser Ala
            115                 120

<210> SEQ ID NO 7
<211> LENGTH: 312
<212> TYPE: DNA
```

<213> ORGANISM: Artificial Sequence
<220> FEATURE:
<223> OTHER INFORMATION: Immunoglobulin VL(K) region

<400> SEQUENCE: 7

```
ctctccctgc ctgtcagtct tggagatcaa gcctccatct cttgcagatc tagtcagacc      60
attgtacata gtaatggaaa cacctattta gaatggtacc tgcagaaacc aggccagtct     120
ccaaagctcc tgatctacaa agtttccaac cgatttttctg gggtcccaga caggttcagt    180
ggcagtggat cagggacaga tttcacactc aagatcagca gagtggaggc tgaggatctg     240
ggagtttatt actgctttca aggttcacat gttccgtgga cgttcggtgg aggcaccaag     300
ctggaaatca aa                                                          312
```

<210> SEQ ID NO 8
<211> LENGTH: 104
<212> TYPE: PRT
<213> ORGANISM: Artificial Sequence
<220> FEATURE:
<223> OTHER INFORMATION: Immunoglobulin VL(K) region

<400> SEQUENCE: 8

```
Leu Ser Leu Pro Val Ser Leu Gly Asp Gln Ala Ser Ile Ser Cys Arg
1               5                   10                  15
Ser Ser Gln Thr Ile Val His Ser Asn Gly Asn Thr Tyr Leu Glu Trp
            20                  25                  30
Tyr Leu Gln Lys Pro Gly Gln Ser Pro Lys Leu Leu Ile Tyr Lys Val
        35                  40                  45
Ser Asn Arg Phe Ser Gly Val Pro Asp Arg Phe Ser Gly Ser Gly Ser
    50                  55                  60
Gly Thr Asp Phe Thr Leu Lys Ile Ser Arg Val Glu Ala Glu Asp Leu
65                  70                  75                  80
Gly Val Tyr Tyr Cys Phe Gln Gly Ser His Val Pro Trp Thr Phe Gly
                85                  90                  95
Gly Gly Thr Lys Leu Glu Ile Lys
            100
```

<210> SEQ ID NO 9
<211> LENGTH: 372
<212> TYPE: DNA
<213> ORGANISM: Artificial Sequence
<220> FEATURE:
<223> OTHER INFORMATION: Immunoglobulin VH Region

<400> SEQUENCE: 9

```
gaggtgcagc tgcagcagtc tggggctgag cttgtgatgc ctggggcttc agtgaagctg      60
tcctgcaagg cttctggcta caccttcacc agctactgga tgcactgggt gaagcagagg     120
cctggacaag gccttgagtg ggtcgcagag attgatcctt ctgatagtta tactaactac     180
aatcaaaagt tcaagggcaa ggccacattg actgtagaca atcctccag cacagcctac      240
atgcagctca gcagcctgac atctgaggac tctgcggtct attactgtgc aagagatggg     300
gatatattaa ctacggtagt agctaagggg tttgtttact ggggccaagg gactctggtc     360
actgtctctg ca                                                          372
```

<210> SEQ ID NO 10
<211> LENGTH: 124
<212> TYPE: PRT
<213> ORGANISM: Artificial Sequence
<220> FEATURE:

<223> OTHER INFORMATION: Immunoglobulin VH Region

<400> SEQUENCE: 10

```
Glu Val Gln Leu Gln Gln Ser Gly Ala Glu Leu Val Met Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Val
        35                  40                  45

Ala Glu Ile Asp Pro Ser Asp Ser Tyr Thr Asn Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Asp Ile Leu Thr Thr Val Val Ala Lys Gly Phe Val
            100                 105                 110

Tyr Trp Gly Gln Gly Thr Leu Val Thr Val Ser Ala
        115                 120
```

<210> SEQ ID NO 11
<211> LENGTH: 312
<212> TYPE: DNA
<213> ORGANISM: Artificial Sequence
<220> FEATURE:
<223> OTHER INFORMATION: Immunoglobulin VL(K) region

<400> SEQUENCE: 11

```
ctctccctgc ctgtcagtct tggagatcaa gcctccatct cttgcagatc tagtcagacc      60
attgtacata gtaatggaaa cacctattta gaatggtacc tgcagaaacc aggccagtct     120
ccaaagctcc tgatctacaa gtttccaac cgattttctg ggtcccaga caggttcagt       180
ggcagtggat cagggacaga tttcacactc aagatcagca gagtggaggc tgaggatctg     240
ggagtttatt actgctttca aggttcacat gttccgtgga cgttcggtgg aggcaccaag     300
ctggaaatca aa                                                         312
```

<210> SEQ ID NO 12
<211> LENGTH: 104
<212> TYPE: PRT
<213> ORGANISM: Artificial Sequence
<220> FEATURE:
<223> OTHER INFORMATION: Immunoglobulin VL(K) region

<400> SEQUENCE: 12

```
Leu Ser Leu Pro Val Ser Leu Gly Asp Gln Ala Ser Ile Ser Cys Arg
1               5                   10                  15

Ser Ser Gln Thr Ile Val His Ser Asn Gly Asn Thr Tyr Leu Glu Trp
            20                  25                  30

Tyr Leu Gln Lys Pro Gly Gln Ser Pro Lys Leu Leu Ile Tyr Lys Val
        35                  40                  45

Ser Asn Arg Phe Ser Gly Val Pro Asp Arg Phe Ser Gly Ser Gly Ser
    50                  55                  60

Gly Thr Asp Phe Thr Leu Lys Ile Ser Arg Val Glu Ala Glu Asp Leu
65                  70                  75                  80

Gly Val Tyr Tyr Cys Phe Gln Gly Ser His Val Pro Trp Thr Phe Gly
                85                  90                  95

Gly Gly Thr Lys Leu Glu Ile Lys
```

<210> SEQ ID NO 13
<211> LENGTH: 360
<212> TYPE: DNA
<213> ORGANISM: Artificial Sequence
<220> FEATURE:
<223> OTHER INFORMATION: Immunoglobulin VH Region

<400> SEQUENCE: 13

```
gaagttaagc tggaggagtc tggggctgag cttgtgatgc ctggggcttc agtgaagctg    60
tcctgcaagg cttctggcta caccttcacc agctactgga tgcactgggt gaagcagagg   120
cctggacaag gccttgagtg gtcgcagag attgatcctt ctgatagtta tactaactac    180
aatcaaaagt tcaagggcaa ggccacattg actgtagaca atcctccag cacagcctac    240
atgcagctca gcagcctgac atctgaggac tctgcggtct attactgtgc aagagatggg   300
gatatattaa ctacggtagt agctaagggg tttgtttact ggggccaagg gactctggtc    360
```

<210> SEQ ID NO 14
<211> LENGTH: 120
<212> TYPE: PRT
<213> ORGANISM: Artificial Sequence
<220> FEATURE:
<223> OTHER INFORMATION: Immunoglobulin VH Region

<400> SEQUENCE: 14

Glu Val Lys Leu Glu Glu Ser Gly Ala Glu Leu Val Met Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Val
        35                  40                  45

Ala Glu Ile Asp Pro Ser Asp Ser Tyr Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Asp Ile Leu Thr Thr Val Val Ala Lys Gly Phe Val
            100                 105                 110

Tyr Trp Gly Gln Gly Thr Leu Val
        115                 120

<210> SEQ ID NO 15
<211> LENGTH: 312
<212> TYPE: DNA
<213> ORGANISM: Artificial Sequence
<220> FEATURE:
<223> OTHER INFORMATION: Immunoglobulin VL(K) region

<400> SEQUENCE: 15

```
ctctccctgc ctgtcagtct tggagatcaa gcctccatct cttgcagatc tagtcagacc    60
attgtacata gtaatggaaa cacctattta gaatggtacc tgcagaaacc aggccagtct   120
ccaaagctcc tgatctacaa agtttccaac cgattttctg ggtcccaga caggttcagt    180
ggcagtggat caggacaga tttcacactc aagatcagca gagtggaggc tgaggatctg    240
ggagtttatt actgctttca aggttcacat gttccgtgga cgttcggtgg aggcaccaag   300
ctggaaatca aa                                                       312
```

```
<210> SEQ ID NO 16
<211> LENGTH: 104
<212> TYPE: PRT
<213> ORGANISM: Artificial Sequence
<220> FEATURE:
<223> OTHER INFORMATION: Immunoglobulin VL(K) region

<400> SEQUENCE: 16

Leu Ser Leu Pro Val Ser Leu Gly Asp Gln Ala Ser Ile Ser Cys Arg
1               5                   10                  15

Ser Ser Gln Thr Ile Val His Ser Asn Gly Asn Thr Tyr Leu Glu Trp
                20                  25                  30

Tyr Leu Gln Lys Pro Gly Gln Ser Pro Lys Leu Leu Ile Tyr Lys Val
            35                  40                  45

Ser Asn Arg Phe Ser Gly Val Pro Asp Arg Phe Ser Gly Ser Gly Ser
        50                  55                  60

Gly Thr Asp Phe Thr Leu Lys Ile Ser Arg Val Glu Ala Glu Asp Leu
65                  70                  75                  80

Gly Val Tyr Tyr Cys Phe Gln Gly Ser His Val Pro Trp Thr Phe Gly
                85                  90                  95

Gly Gly Thr Lys Leu Glu Ile Lys
            100
```